United States Patent
Gwaltney et al.

(10) Patent No.: US 8,133,898 B2
(45) Date of Patent: Mar. 13, 2012

(54) RENIN INHIBITORS

(75) Inventors: Stephen L. Gwaltney, San Diego, CA (US); Zhiyuan Zhang, San Deigo, CA (US); Betty Lam, Spring Valley, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 212 days.

(21) Appl. No.: 12/529,167

(22) PCT Filed: Mar. 11, 2008

(86) PCT No.: PCT/US2008/056509
§ 371 (c)(1), (2), (4) Date: Sep. 22, 2009

(87) PCT Pub. No.: WO2008/121506
PCT Pub. Date: Oct. 9, 2008

(65) Prior Publication Data
US 2010/0137310 A1   Jun. 3, 2010

(51) Int. Cl.
*A01N 43/90* (2006.01)
*A61K 31/519* (2006.01)
*C07D 491/00* (2006.01)
*C07D 495/00* (2006.01)
*C07D 471/00* (2006.01)

(52) U.S. Cl. ............. 514/264.1; 544/278; 544/279
(58) Field of Classification Search ............ 544/278, 544/279; 514/264.1
See application file for complete search history.

(56) References Cited

U.S. PATENT DOCUMENTS
2006/0014764 A1   1/2006   Feng

FOREIGN PATENT DOCUMENTS
WO   WO/2006/019965   2/2006
WO   WO/2008/121506   10/2008

*Primary Examiner* — Paul V. Ward
(74) *Attorney, Agent, or Firm* — Matthew J. Russo; C. Amy Smith

(57) ABSTRACT

The invention provides compounds, pharmaceutical compositions, kits, method of preparing, and method of using the compounds which exhibit renin and other S9 proteases activities and consist of the formula:—wherein the variables are as defined herein.

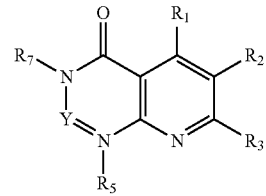

21 Claims, 1 Drawing Sheet

DNA Sequence Encoding First PCR Primer [SEQ ID NO: 1]

1.  AAGCTTATGG ATGGATGGAG A

DNA Sequence Encoding Second PCR Primer [SEQ ID NO: 2]

1.  GGATCCTCAG CGGGCCAAGG C

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Primers

<400> SEQUENCE: 1
aagcttatgg atggatggag a                                           21

<210> SEQ ID NO 2
<211> LENGTH: 21
<212> TYPE: DNA
<213> ORGANISM: Artificial Sequence
<220> FEATURE:
<223> OTHER INFORMATION: Synthetic Primers

<400> SEQUENCE: 2
ggatcctcag cgggccaagg c                                           21

RENIN INHIBITORS

FIELD OF THE INVENTION

The present invention relates to compounds that may be used to inhibit renin, as well as compositions of matter and kits comprising these compounds. The invention also relates to methods for inhibiting renin and treatment methods using compounds according to the present invention.

BACKGROUND OF THE INVENTION

The renin-angiotensin-aldosterone system ("RAAS") is one of the hormonal mechanisms involved in regulating pressure/volume homeostasis and also in the development of hypertension, a condition that can progress to more serious cardiovascular diseases such as congestive heart failure. Activation of RAAS begins with secretion of the enzyme renin from juxtaglomerular cells in the kidney.

Renin, a member of the aspartyl protease family, passes from the kidneys into the blood where it cleaves angiotensinogen to generate the decapeptide angiotensin I. Angiotensin I is then cleaved in the lungs, the kidneys and other organs by the angiotensin-converting enzyme (ACE) to form the octapeptide angiotensin II. Angiotensin II, which is known to work at least on two receptor subtypes ($AT_1$ and $AT_2$), increases blood pressure both directly by arterial vasoconstriction and indirectly by liberating from the adrenal glands the sodium-ion-retaining hormone aldosterone. Angiotensin II also produces other physiological effects such as promoting sodium and fluid retention, inhibiting renin secretion, increasing sympathetic nervous system activity, stimulating vasopressin secretion, causing a positive cardiac inotropic effect and modulating other hormonal systems.

Modulation of the RAAS represents a major advance in the treatment of cardiovascular diseases. In particular, the rationale to develop renin inhibitors lies in its specificity (Kleinert H. D., *Cardiovasc. Drugs*, 1995, 9, 645). The only substrate known for renin is angiotensinogen, which can only be processed (under physiological conditions) by renin. Inhibitors of the enzymatic activity of renin are therefore expected to bring about a reduction in the formation of angiotensin I and angiotensin II.

In view of the foregoing, renin is an especially attractive target for the discovery of new therapeutics for cardiovascular disease, hypertension, congestive heart failure, myocardial infarction, renal protection, inflammation, neurological diseases, cancer, and other diseases. Accordingly, there is a need to find new renin inhibitors for use as therapeutic agents to treat human diseases. In particular, there is a continued need for metabolically stable, orally bioavailable renin inhibitors that can be prepared on a large scale.

Modeling of the active site of renin has now revealed that certain classes of known compounds, including those described in US 2005/072765 A1 US 2006/014764 A1, WO 2005/118555 and WO 2006/020017, may also possess renin activity. Those compounds were previously reported to be DPP-IV inhibitors, but they have now proven to be useful leads in the search for renin inhibitors.

SUMMARY OF THE INVENTION

The present invention relates to compounds that have activity for inhibiting renin. The present invention provides compounds, pharmaceutical compositions, articles of manufacture and kits comprising these compounds, and also methods of using and method of preparing these compounds.

In one aspect, the invention is directed to compounds, tautomers, stereoisomers, and pharmaceutically acceptable salts thereof, having the formula:

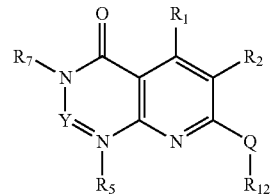

wherein
Q is selected from the group consisting of —O—, —S—, and —$NR_{13}$—;
Y is selected from the group consisting of —C(O)—, —C(S)—, —S(O)—, —$S(O)_2$—, —$C(R_6)(R_{6'})$—, and —$C(NR_6R_{6'})$—;
$R_1$ is selected from the group consisting of hydrogen, ($C_{1-10}$)alkyl, ($C_{3-12}$)cycloalkyl, ($C_{3-12}$)heterocycloalkyl, aryl($C_{1-10}$)alkyl, ($C_{1-5}$)heteroarylalkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;
$R_2$ is selected from the group consisting of amino($C_{1-6}$)alkyl, ($C_{3-12}$)heterocycloalkyl, ($C_{4-12}$)heterobicycloaryl, heteroaryl, and cyano, each substituted or unsubstituted;
$R_5$ and $R_7$ are each independently selected from the group consisting of hydrogen, amino, sulfonamido, ($C_{1-10}$)alkyl, ($C_{1-10}$)haloalkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{4-12}$)heterobicycloaryl, ($C_{3-12}$)cycloalkyl($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted; or $R_5$ is absent when the nitrogen atom on which $R_5$ is drawn forms part of a double bond;
$R_6$ and $R_{6'}$ are each independently selected from the group consisting of hydrogen, nitro, sulfonamido, ($C_{1-10}$)alkyl, ($C_{1-10}$)azaalkyl, ($C_{1-10}$)oxaalkyl, ($C_{1-10}$)oxoalkyl, hydroxy ($C_{1-10}$)alkyl, ($C_{3-12}$)cycloalkyl, ($C_{1-12}$)heterocycloalkyl, aryl ($C_{1-10}$)alkyl, ($C_{1-5}$)heteroarylalkyl, ($C_{9-12}$)bicycloaryl, ($C_{4-12}$)heterobicycloaryl, ($C_{3-12}$)cycloalkyl($C_{1-10}$)alkyl, ($C_{3-12}$)heterocycloalkyl($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, oxy group, carbonyl group, amino group, imino group, thio group, sulfonyl group and sulfinyl group, each substituted or unsubstituted; or $R_{6'}$ is absent when the atom on which $R_{6'}$ is drawn forms part of a double bond, or when Y is $CR_6R_{6'}$, $R_6$ and $R_{6'}$ is taken together to form an oxo or a thioxo group;
$R_{12}$ is selected from the group consisting of ($C_{3-10}$)alkyl, phenyl, phenylalkyl, naphthylalkyl, substituted or unsubstituted; and
$R_{13}$ is selected from the group consisting of hydrogen, ($C_{1-10}$)haloalkyl, amino, thio, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, and imino group, each substituted or unsubstituted.

In another aspect, the invention relates to pharmaceutical compositions that comprise a renin inhibitor according to the present invention as an active ingredient and a pharmaceutical acceptable excipient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention provides kits that comprise a composition comprising at least on renin inhibitor of the present invention for treating disease states associated with renin.

In another aspect, the invention provides an article of manufacture that comprises a composition comprising at least one renin inhibitor of the present invention. The article of manufacture may comprise the composition in single or multiple dose forms and may also optionally comprise additional components, such as syringes for administration of the composition.

In another aspect, the invention is related to methods for preparing the compounds, compositions and kits according to the present invention. For example, several synthetic schemes are provided herein for synthesizing compounds according to the present invention.

In another aspect, the invention is related to reagents that may be used in the preparation of the compounds according to the invention.

In another aspect, the invention is related to methods for using compounds, compositions, kits and articles of manufacture according to the present invention. Particularly, the compounds, compositions, kits and articles of manufacture are used to inhibit renin.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound of or having the formula" is intended to encompass the compound and all pharmaceutically acceptable ionized forms and solvates, all possible stereoisomers, all possible resonance forms and tautomers, all pharmaceutically acceptable salts and their polymorphs, unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit renin and thus may themselves be prodrugs for another compound. Such prodrugs of another compound may or may not themselves independently have renin inhibitory activity.

BRIEF DESCRIPTION OF THE FIGURES

FIG. 1 illustrates SEQ ID NO: 1 and SEQ ID NO: 2 referred to in this application.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $5^{TH}$ ED." Vols. A (2007) and B (2007), Springer Science+Business Media, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $(C_{3-8})$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a $(C_{2-20})$alkenyl, a $(C_{2-15})$alkenyl, a $(C_{2-10})$alkenyl, a $(C_{2-5})$alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$alkenylene, a $(C_{2-15})$alkenylene, a $(C_{2-10})$alkenylene, a $(C_{2-5})$alkenylene or a $(C_{2-3})$alkenylene. Alternatively, "alkenylene," either alone or represented along with another radical, can be a ($C_2$)alkenylene, a ($C_3$)alkenylene or a ($C_4$)alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tent-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., ($C_{6-10}$)aryl($C_{1-3}$)alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a ($C_{1-20}$)alkyl, a ($C_{1-15}$)alkyl, a ($C_{1-10}$)alkyl, a ($C_{1-5}$)alkyl or a ($C_{1-3}$)alkyl. Alternatively, "alkyl," either alone or represented along with another radical, can be a ($C_1$)alkyl, a ($C_2$)alkyl or a ($C_3$)alkyl.

"Alkylene", unless indicated otherwise, means a straight or branched, saturated or unsaturated, aliphatic, divalent radical. ($C_X$)alkylene and ($C_{X-Y}$)alkylene are typically used where X and Y indicate the number of carbon atoms in the chain. For example, ($C_{1-6}$)alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like. In particular embodiments, "alkylene," either alone or represented along with another radical, can be a ($C_{1-20}$)alkylene, a ($C_{1-15}$)alkylene, a ($C_{1-10}$)alkylene, a ($C_{1-5}$)alkylene or a ($C_{1-3}$)alkylene. Alternatively, "alkylene," either alone or represented along with another radical, can be a ($C_1$)alkylene, a ($C_2$)alkylene or a ($C_3$)alkylene.

"Alkylidene" means a straight or branched, saturated or unsaturated, aliphatic radical connected to the parent molecule by a double bond. ($C_X$)alkylidene and ($C_{X-Y}$)alkylidene are typically used where X and Y indicate the number of carbon atoms in the chain. For example, ($C_{1-6}$)alkylidene includes methylene (=$CH_2$), ethylidene (=$CHCH_3$), isopropylidene (=$C(CH_3)_2$), propylidene (=$CHCH_2CH_3$), allylidene (=CH—CH=$CH_2$), and the like. In particular embodiments, "alkylidene," either alone or represented along with another radical, can be a ($C_{1-20}$)alkylidene, a ($C_{1-15}$)alkylidene, a ($C_{1-10}$)alkylidene, a ($C_{1-5}$)alkylidene or a ($C_{1-3}$)alkylidene. Alternatively, "alkylidene," either alone or represented along with another radical, can be a ($C_1$)alkylidene, a ($C_2$)alkylidene or a ($C_3$)alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a ($C_{2-20}$)alkynyl, a ($C_{2-15}$)alkynyl, a ($C_{2-10}$)alkynyl, a ($C_{2-5}$)alkynyl or a ($C_{2-3}$)alkynyl. Alternatively, "alkynyl," either alone or represented along with another radical, can be a ($C_2$)alkynyl, a ($C_3$)alkynyl or a ($C_4$)alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a ($C_{2-20}$)alkynylene, a ($C_{2-15}$)alkynylene, a ($C_{2-10}$)alkynylene, a ($C_{2-5}$)alkynylene or a ($C_{2-3}$)alkynylene. Alternatively, "alkynylene," either alone or represented along with another radical, can be a ($C_2$)alkynylene, a ($C_3$) alkynylene or a ($C_4$)alkynylene.

"Amido" means the radical —C(=O)—NR—, —C(=O)—NRR', —NR—C(=O)— and/or —NR—C(=O)R', wherein each R and R' are independently hydrogen or a further substituent.

"Amino" means a nitrogen moiety having two further substituents where, for example, a hydrogen or carbon atom is attached to the nitrogen. For example, representative amino groups include —$NH_2$, —$NHCH_3$, —N($CH_3$)$_2$, —NH(($C_{1-10}$)alkyl), —N(($C_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. ($C_X$)aryl and ($C_{X-Y}$)aryl are typically used where X and Y indicate the number of carbon atoms in the ring. In particular embodiments, "aryl," either alone or represented along with another radical, can be a ($C_{3-14}$)aryl, a ($C_{3-10}$)aryl, a ($C_{3-7}$)aryl, a ($C_{8-10}$)aryl or a ($C_{5-7}$)aryl. Alternatively, "aryl," either alone or represented along with another radical, can be a ($C_5$)aryl, a ($C_6$)aryl, a ($C_7$)aryl, a ($C_8$)aryl., a ($C_9$)aryl or a ($C_{10}$)aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a ($C_{1-10}$)azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a ($C_{4-15}$)bicycloalkyl, a ($C_{4-10}$)bicycloalkyl, a ($C_{6-10}$)bicycloalkyl or a ($C_{8-10}$)bicycloalkyl. Alternatively, "bicycloalkyl," either alone or represented along with another radical, can be a ($C_8$)bicycloalkyl, a ($C_9$)bicycloalkyl or a ($C_{10}$)bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tent-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl., a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene., a $(C_9)$cycloalkylene or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"$EC_{50}$" means the molar concentration of an agonist that produces 50% of the maximal possible effect of that agonist. The action of the agonist may be stimulatory or inhibitory.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-15})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-c]pyrimidine, pyrrolo[3,2-c]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Iminoketone derivative" means a derivative comprising the moiety —C(NR)—, wherein R is hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 5th edition, March, Jerry, John Wiley & Sons, New York, 2001).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in P. G. M. Wuts and T. W. Greene, "Greene's Protecting Groups in Organic Synthesis, 4th edition, John Wiley & Sons, Inc. 2007.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

preventing the disease from occurring in an animal which may be predisposed to the disease but does not yet experience or display the pathology or symptomatology of the disease, inhibiting the disease in an animal that is experiencing or displaying the pathology or symptomatology of the diseased (i.e., arresting further development of the pathology and/or symptomatology), or ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

represents

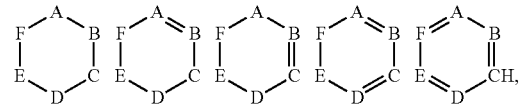

etc.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

DETAILED DESCRIPTION OF THE INVENTION

The present invention relates to compounds, compositions, kits and articles of manufacture that may be used to inhibit renin. The present invention also relates to methods for inhibiting renin and treatment methods using compounds according to the present invention.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members. In addition, the compounds of the present invention may be useful as inhibitors of plasmepsins to treat malaria and as inhibitors of *Candida albicans* secreted aspartyl proteases to treat fungal infections.

It further noted that the compounds of the present invention also possess inhibitory activity for dipeptidyl peptidase IV (DPPIV).

In one aspect, the invention is directed to compounds which may be use for renin. These compounds may also be use for DPPIV. In one embodiment, the compound is of the formula:

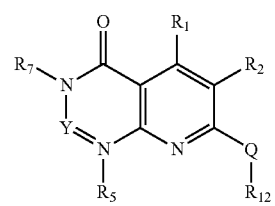

wherein
Q is selected from the group consisting of —O—, —S—, and —NR$_{13}$—;
Y is selected from the group consisting of —C(O)—, —C(S), —S(O), —S(O)$_2$—, —C(R$_6$)(R$_{6'}$)— and —C(NR$_6$R$_{6'}$)—;
R$_1$ is selected from the group consisting of hydrogen, (C$_{1-10}$)alkyl, (C$_{3-12}$)cycloalkyl, (C$_{3-12}$)heterocycloalkyl, aryl (C$_{1-10}$)alkyl, (C$_{1-5}$)heteroarylalkyl, (C$_{9-12}$)bicycloaryl, (C$_{4-12}$)heterobicycloaryl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, imino (C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;
R$_2$ is selected from the group consisting of amino(C$_{1-6}$) alkyl, (C$_{3-12}$)heterocycloalkyl, (C$_{4-12}$)heterobicycloaryl, heteroaryl, and cyano, each substituted or unsubstituted;

$R_5$ and $R_7$ are each independently selected from the group consisting of hydrogen, amino, sulfonamido, $(C_{1-10})$alkyl, $(C_{1-10})$haloalkyl, $(C_{3-12})$cycloalkyl, $(C_{3-12})$heterocycloalkyl, aryl$(C_{1-10})$alkyl, heteroaryl$(C_{1-5})$alkyl, $(C_{9-12})$bicycloaryl, $(C_{4-12})$heterobicycloaryl, $(C_{3-12})$cycloalkyl$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted; or $R_5$ is absent when the nitrogen atom on which $R_5$ is drawn forms part of a double bond;

$R_6$ and $R_{6'}$ are each independently selected from the group consisting of hydrogen, nitro, sulfonamido, $(C_{1-10})$alkyl, $(C_{1-10})$azaalkyl, $(C_{1-10})$oxaalkyl, $(C_{1-10})$oxoalkyl, hydroxy $(C_{1-10})$alkyl, $(C_{3-12})$cycloalkyl, $(C_{1-12})$heterocycloalkyl, aryl $(C_{1-10})$alkyl, $(C_{1-5})$heteroarylalkyl, $(C_{9-12})$bicycloaryl, $(C_{4-12})$heterobicycloaryl, $(C_{3-12})$cycloalkyl$(C_{1-10})$alkyl, $(C_{3-12})$heterocycloalkyl$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, oxy group, carbonyl group, amino group, imino group, thio group, sulfonyl group and sulfinyl group, each substituted or unsubstituted; or $R_{6'}$ is absent when the atom on which $R_{6'}$ is drawn forms part of a double bond, or when Y is $CR_6R_{6'}$, $R_6$ and $R_{6'}$ is taken together to form an oxo or a thioxo group;

$R_{12}$ is selected from the group consisting of $(C_{3-10})$alkyl, phenyl, phenylalkyl, naphthylalkyl, substituted or unsubstituted; and $R_{13}$ is selected from the group consisting of hydrogen, $(C_{1-10})$haloalkyl, amino, thio, $(C_{1-10})$alkyl, $(C_{3-12})$cycloalkyl, $(C_{3-12})$heterocycloalkyl, aryl$(C_{1-10})$alkyl, heteroaryl$(C_{1-5})$alkyl, $(C_{9-12})$bicycloaryl, $(C_{4-12})$heterobicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, and imino group, each substituted or unsubstituted.

In another embodiment, the compound of the invention is of the formula

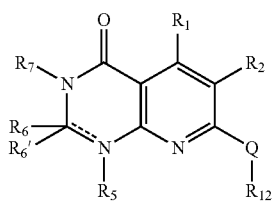

wherein

Q is selected from the group consisting of —O—, —S—, and —$NR_{13}$—;

$R_1$ is selected from the group consisting of hydrogen, $(C_{1-10})$alkyl, $(C_{3-12})$cycloalkyl, $(C_{3-12})$heterocycloalkyl, aryl $(C_{1-10})$alkyl, $(C_{1-5})$heteroarylalkyl, $(C_{9-12})$bicycloaryl, $(C_{4-12})$heterobicycloaryl, carbonyl$(C_{1-3})$alkyl, thiocarbonyl $(C_{1-3})$alkyl, sulfonyl$(C_{1-3})$alkyl, sulfinyl$(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;

$R_2$ is selected from the group consisting of amino$(C_{1-6})$alkyl, $(C_{3-12})$heterocycloalkyl, $(C_{4-12})$heterobicycloaryl, heteroaryl, and cyano, each substituted or unsubstituted;

$R_5$ and $R_7$ are each independently selected from the group consisting of hydrogen, amino, sulfonamido, $(C_{1-10})$alkyl, $(C_{1-10})$haloalkyl, $(C_{3-12})$cycloalkyl, $(C_{3-12})$heterocycloalkyl, aryl$(C_{1-10})$alkyl, heteroaryl$(C_{1-5})$alkyl, $(C_{9-12})$bicycloaryl, $(C_{4-12})$heterobicycloaryl, $(C_{3-12})$cycloalkyl$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted; or $R_5$ is absent when the nitrogen atom on which $R_5$ is drawn forms part of a double bond;

$R_6$ and $R_{6'}$ are each independently selected from the group consisting of hydrogen, nitro, sulfonamido, $(C_{1-10})$alkyl, $(C_{1-10})$azaalkyl, $(C_{1-10})$oxaalkyl, $(C_{1-10})$oxo alkyl, hydroxy $(C_{1-10})$alkyl, $(C_{3-12})$cycloalkyl, $(C_{1-12})$heterocycloalkyl, aryl $(C_{1-10})$alkyl, $(C_{1-5})$heteroarylalkyl, $(C_{9-12})$bicycloaryl, $(C_{4-12})$heterobicycloaryl, $(C_{3-12})$cycloalkyl$(C_{1-10})$alkyl, $(C_{3-12})$heterocycloalkyl$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, oxy group, carbonyl group, amino group, imino group, thio group, sulfonyl group and sulfinyl group, each substituted or unsubstituted; or $R_6$ and $R_{6'}$ is taken together to form an oxo or a thioxo group; or $R_{6'}$ is absent when the carbon on which $R_{6'}$ is drawn forms part of a double bond;

$R_{12}$ is selected from the group consisting of $(C_{3-10})$alkyl, phenyl, phenylalkyl, naphthylalkyl, substituted or unsubstituted; and $R_{13}$ is selected from the group consisting of hydrogen, $(C_{1-10})$haloalkyl, amino, thio, $(C_{1-10})$alkyl, $(C_{3-12})$cycloalkyl, $(C_{3-12})$heterocycloalkyl, aryl$(C_{1-10})$alkyl, heteroaryl$(C_{1-5})$alkyl, $(C_{9-12})$bicycloaryl, $(C_{4-12})$heterobicycloaryl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, hydroxy, alkoxy, aryloxy, heteroaryloxy, and imino group, each substituted or unsubstituted.

In yet another embodiment, the compound of the invention is of the formula

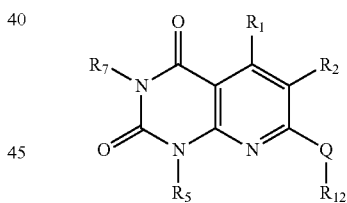

wherein

Q is selected from the group consisting of —O—, —S—, and —$NR_{13}$—;

$R_1$ is selected from the group consisting of hydrogen, $(C_{1-10})$alkyl, $(C_{3-12})$cycloalkyl, $(C_{3-12})$heterocycloalkyl, aryl $(C_{1-10})$alkyl, $(C_{1-5})$heteroarylalkyl, $(C_{9-12})$bicycloaryl, $(C_{4-12})$heterobicycloaryl, carbonyl$(C_{1-3})$alkyl, thiocarbonyl $(C_{1-3})$alkyl, sulfonyl$(C_{1-3})$alkyl, sulfinyl$(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;

$R_2$ is selected from the group consisting of amino$(C_{1-6})$alkyl, $(C_{3-12})$heterocycloalkyl, $(C_{4-12})$heterobicycloaryl, heteroaryl, and cyano, each substituted or unsubstituted;

$R_5$ and $R_7$ are each independently selected from the group consisting of hydrogen, amino, sulfonamido, $(C_{1-10})$alkyl, $(C_{1-10})$haloalkyl, $(C_{3-12})$cycloalkyl, $(C_{3-12})$heterocycloalkyl, aryl$(C_{1-10})$alkyl, heteroaryl$(C_{1-5})$alkyl, $(C_{9-12})$bicycloaryl, ($C_{4-12}$)heterobicycloaryl, ($C_{3-12}$)cycloalkyl($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted; or $R_5$ is absent when the nitrogen atom on which $R_5$ is bound forms part of a double bond;

$R_{12}$ is selected from the group consisting of ($C_{3-10}$)alkyl, phenyl, phenylalkyl, naphthylalkyl, substituted or unsubstituted; and $R_{13}$ is selected from the group consisting of hydrogen, ($C_{1-10}$)haloalkyl, amino, thio, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, and imino group, each substituted or unsubstituted.

$R_6$

In some variations of the above embodiments, $R_6$ and $R_{6'}$, when present, are each independently selected from the group consisting of hydrogen, hydroxy, alkoxy, aryloxy, ($C_{1-10}$)alkyl, ($C_{1-10}$)azaalkyl, ($C_{1-10}$)oxaalkyl, ($C_{1-10}$)oxoalkyl, hydroxy($C_{1-10}$)alkyl, aryl, heteroaryl, ($C_{3-7}$)cycloalkyl, hetero($C_{1-6}$)cycloalkyl, aryl($C_{1-5}$)alkyl, heteroaryl($C_{1-5}$)alkyl, ($C_{3-7}$)cycloalkyl($C_{1-5}$)alkyl, hetero($C_{1-6}$)cycloalkyl($C_{1-5}$)alkyl, oxy group, carbonyl group, amino group, thio group, sulfonyl group and sulfinyl group, each substituted or unsubstituted; or $R_{6'}$ is absent when the atom on which $R_{6'}$ is bound forms part of a double bond, or when Y is $CR_6R_{6'}$, $R_6$ and $R_{6'}$ is taken together to form an oxo or a thioxo group.

In some other variations of the above embodiments, $R_6$ is $-L-(CH_2)_n-R_{22}$ and $R_{6'}$ is hydrogen or is absent where n is 0, 1, 2 or 3;

L is absent or is selected from the group consisting of $-CR_{23}R_{23'}-$, $-O-$, $-S-$, and $-NR_{23}-$, where $R_{23}$ and $R_{23'}$ are each independently selected from the group consisting of hydrogen, alkoxy, alkyl, aryl, ($C_{1-6}$)heteroaryl, ($C_{3-6}$)cycloalkyl, and ($C_{1-6}$)heterocycloalkyl, each unsubstituted or substituted; and $R_{22}$ is selected from the group consisting of aryl, heteroaryl, ($C_{3-7}$)cycloalkyl and ($C_{1-6}$)heterocycloalkyl, each unsubstituted or substituted.

In some particular variations of the above embodiment, $R_{22}$ is phenyl.

$R_5$ and $R_7$

In some variations of the above embodiments and variations, $R_5$ and $R_7$ are each independently from the group consisting of hydrogen, ($C_{1-10}$)haloalkyl, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, and ($C_{3-12}$)cycloalkyl($C_{1-10}$)alkyl, each substituted or unsubstituted.

In some variations of the above embodiments and variations, $R_5$ and $R_7$ are each independently selected from the group consisting of hydrogen, ($C_{1-10}$)haloalkyl and ($C_{1-10}$)alkyl, each substituted or unsubstituted.

In other variations, $R_5$ and $R_7$ are each independently selected from the group consisting of hydrogen and ($C_{1-6}$)alkyl.

In yet other variations, $R_5$ is hydrogen or methyl. In yet other variations, $R_7$ is hydrogen or methyl.

In still other variations, $R_5$ and $R_7$ are both methyl.

$R_2$

In some variations of the above embodiments and variations, $R_2$ is $-(CR_8R_9)_q-NR_{10}R_{11}$, where q is 1, 2 or 3;

$R_8$ and $R_9$ are each independently selected from the group consisting of hydrogen, halogen, ($C_{1-10}$)haloalkyl, cyano, nitro, alkyl, cycloalkyl, alkene, alkyne, aryl, and heteroaryl, each substituted or unsubstituted, or where $R_8$ and $R_9$ are taken together to form a substituted or unsubstituted ring; and $R_{10}$ and $R_{11}$ are each independently selected from the group consisting of hydrogen, ($C_{1-10}$)haloalkyl, amino, thio, ($C_{1-10}$)alkyl, ($C_{3-12}$)cycloalkyl, hetero($C_{1-12}$)cycloalkyl, hydroxyalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, and imino group, each substituted or unsubstituted.

It is noted that in some variations, q is 3. In other variations, q is 2. In still other variations, q is 1.

It is also noted that in some variations, $R_8$ and $R_9$ are each independently selected from the group consisting of hydrogen, ($C_{1-10}$)haloalkyl, cyano, alkyl, each substituted or unsubstituted. In other variations $R_8$ is selected from the group consisting of hydrogen and alkyl. In yet other variations, $R_9$ is selected from the group consisting of hydrogen and alkyl. In yet other variations, $R_8$ and $R_9$ are both hydrogen.

In some other variations, $R_{10}$ and $R_{11}$ are each independently selected from the group consisting of hydrogen, ($C_{1-6}$)alkyl, ($C_{3-6}$)cycloalkyl($C_{1-3}$)alkyl, ($C_{1-5}$)heterocycloalkyl($C_{1-3}$)alkyl, hydroxyalkyl, ($C_6$)aryl($C_{1-3}$)alkyl, ($C_{1-5}$)heteroaryl($C_{1-3}$)alkyl, ($C_{3-6}$)cycloalkyl, ($C_{1-5}$)heterocycloalkyl, ($C_6$)aryl, ($C_{1-5}$)heteroaryl, each substituted or unsubstituted. In other variations, $R_{10}$ and $R_{11}$ are each independently selected from the group consisting of hydrogen, and substituted or unsubstituted ($C_{1-6}$)alkyl. In still other variations, $R_{10}$ and $R_{11}$ are each independently selected from the group consisting of hydrogen and ($C_{1-6}$)alkyl, each unsubstituted or substituted with one or more substituents each independently selected from the group consisting of alkyl, alkyoxy, hydroxyl, cyano and halo. In still other variations, $R_{10}$ and $R_{11}$ are each independently selected from the group consisting of hydrogen, methyl and hydroxylethyl. In still other variations, $R_{10}$ and $R_{11}$ is hydroxyl substituted ethyl. In still other variations, $R_{10}$ and $R_{11}$ are both methyl. In still other variations, one of $R_{10}$ and $R_{11}$ is hydrogen. In still other variations, $R_{10}$ and $R_{11}$ are both hydrogen.

In some variations of the above embodiments and variations, $R_2$ is $-CH_2NH_2$.

Q

In some variations of the above embodiments and variations, Q is $-S-$. In other variations, Q is $-NR_{13}-$.

In some variations of the above embodiments and variations, $R_{13}$, when present, is selected from the group consisting of hydrogen, ($C_{1-10}$)alkyl, ($C_{1-10}$)haloalkyl, hydroxyl($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{3-12}$)cycloalkyl($C_{1-5}$)alkyl, ($C_{3-12}$)heterocycloalkyl($C_{1-10}$)alkyl, ($C_{1-10}$)aryl($C_{1-5}$)alkyl, ($C_{1-10}$)heteroaryl($C_{1-5}$)alkyl, ($C_{1-10}$)heteroalkyl, each substituted or unsubstituted. In other variations, $R_{13}$ is selected from the group consisting of hydrogen and ($C_{1-4}$)alkyl. In other variations, $R_{13}$ is hydrogen.

$R_{12}$

In some variations of the above embodiments and variations, $R_{12}$ is selected from the group consisting of phenyl, phenylalkyl or naphthylalkyl, each unsubstituted or substituted. Further, when the alkyl, the phenyl and the naphthyl are substituted, the substituents are independently selected from the group consisting of halo, nitro, cyano, thio, oxy, hydroxy, carbonyloxy, (C_{1-10})alkoxy, (C_{4-12})aryloxy, (C_{1-10})heteroaryl oxy, carbonyl, oxycarbonyl, aminocarbonyl, amino, (C_{1-10})alkylamino, sulfonamido, imino, sulfonyl, sulfinyl, (C_{1-10})alkyl, (C_{1-10})haloalkyl, hydroxy(C_{1-10})alkyl, carbonyl (C_{1-10})alkyl, thiocarbonyl(C_{1-10})alkyl, sulfonyl(C_{1-10})alkyl, sulfinyl(C_{1-10})alkyl, (C_{1-10})azaalkyl, (C_{1-10})oxaalkyl, (C_{1-10})oxoalkyl, imino(C_{1-10})alkyl, (C_{3-12})cycloalkyl(C_{1-5})alkyl, (C_{3-12})heterocycloalkyl(C_{1-10})alkyl, aryl(C_{1-10})alkyl, (C_{1-10})heteroaryl(C_{1-5})alkyl, (C_{9-12})bicycloaryl(C_{1-5})alkyl, (C_{8-12})heterobicycloaryl(C_{1-5})alkyl, (C_{1-10})heteroalkyl, (C_{3-12})cycloalkyl, (C_{3-12})heterocycloalkyl, (C_{9-12})bicycloalkyl, (C_{3-12})heterobicycloalkyl, (C_{4-12})aryl, (C_{1-10})heteroaryl, (C_{9-12})bicycloaryl and (C_{4-12})heterobicycloaryl, each unsubstituted or further substituted. In other variations, the one or more substituents are elected from the group consisting of —CF_3, —OCH_3, —OCH_2CH(CH_3)_2, —NH—CH_2CH_3, —NHC(O)CH_3, —OCH_2CH_2CH_3, —C(O)NCH_2CH_3, benzyloxy,

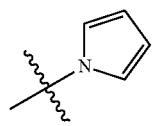

and

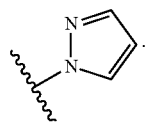

In other variations, the substituents are independently selected from either —OCH_2CH_2CH_3 or —C(O)NCH_2CH_2CH_3.

In the variations where $R_{12}$ is selected from the group consisting of phenyl, phenylalkyl or naphthylalkyl, the alkyl of the phenylalkyl or naphthylalkyl is a $C_1$alkyl, each unsubstituted or substituted. In some variations, the alkyl of the phenylalkyl or naphthylalkyl is a $C_2$alkyl, each unsubstituted or substituted. In some other variations, the alkyl of the phenylalkyl or naphthylalkyl is a $C_3$alkyl, each unsubstituted or substituted. In some variations, the alkyl of the phenylalkyl or naphthylalkyl is unsubstituted. In other variations, the alkyl of the phenylalkyl or naphthylalkyl is substituted and the substituents are each independently selected from the group consisting of hydrogen, hydroxyl, (C_{1-10})alkoxy, (C_{4-12})aryloxy, amino, (C_{1-10})alkyl, hydroxy(C_{1-10})alkyl, (C_{1-10})azaalkyl, (C_{1-10})oxaalkyl, (C_{4-12})aryl, (C_{1-10})heteroaryl, (C_{3-12})cycloalkyl, (C_{3-12})heterocycloalkyl, (C_{3-12})cycloalkyl(C_{1-5})alkyl, (C_{3-12})heterocycloalkyl(C_{1-10})alkyl, aryl(C_{1-10})alkyl and (C_{1-10})heteroaryl(C_{1-5})alkyl, each further substituted or unsubstituted. In still other variations, the alkyl of the phenylalkyl or naphthylalkyl is substituted with a phenyl.

In some variations of the above embodiments and variations, $R_{12}$ is (C_{3-6})alkyl, unsubstituted or substituted with one or more substituents independently selected from the group consisting of hydroxyl, alkoxy, alkyl, alkyoxy, haloalkyl, cyano and halo.

In other variations, $R_{12}$ is —CH(CH_2CH_3)_2.

In still other variations, $R_{12}$ is selected from the group consisting of —CH(CH_2CH_3)_2,

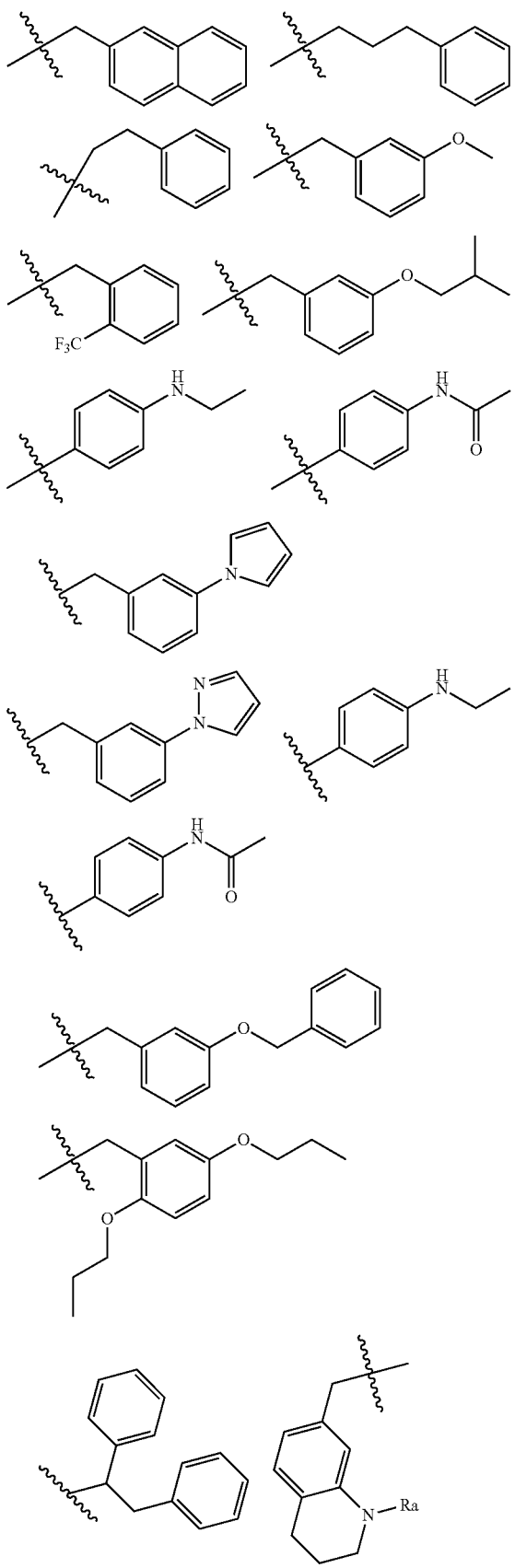

-continued

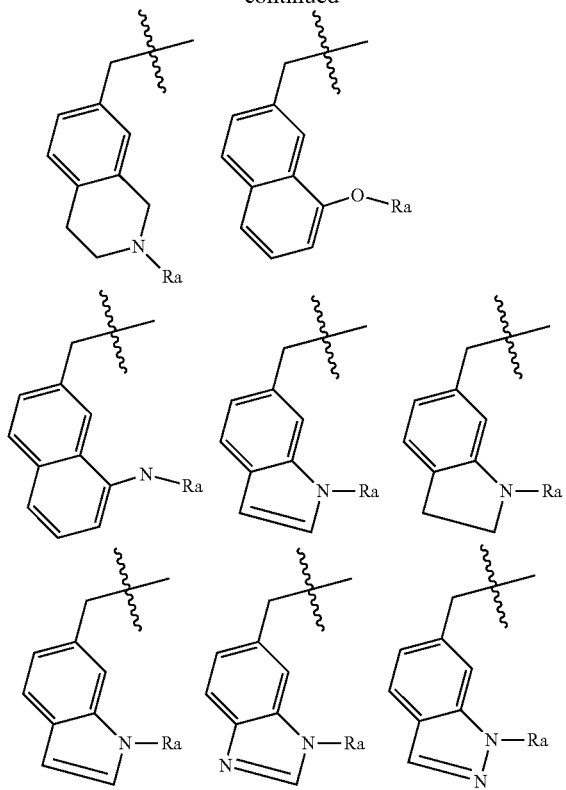

$R_a$ is selected from the group consisting of —(CH$_2$)$_2$OCH$_3$, —(CH$_2$)$_3$OCH$_3$, —(CH$_2$)$_2$NHC(O)CH$_3$, —(CH$_2$)$_3$NHC(O)CH$_3$,

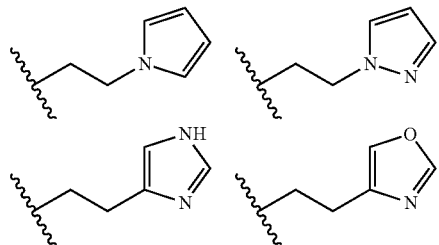

$R_{12}$

In some variations of the above embodiments and variations, $R_1$ is a substituted or unsubstituted ($C_{3-7}$)cycloalkyl. In other variations, $R_1$ is a substituted or unsubstituted ($C_{3-7}$)heterocycloalkyl. In other variations, $R_1$ is a substituted or unsubstituted aryl. In still other variations, $R_1$ is a substituted or unsubstituted phenyl. In yet still other variations, $R_1$ is a substituted or unsubstituted heteroaryl. In yet still other variations, $R_1$ is

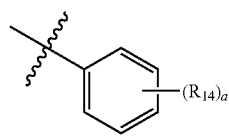

where
a is 0, 1, 2, 3, 4, or 5; and $R_{14}$ is selected from the group consisting of hydrogen, halo, ($C_{1-10}$)perhaloalkyl, amino, nitro, cyano, thio, sulfonamido, ($C_{1-10}$)alkyl, ($C_{3-12}$)cycloalkyl, ($C_{3-12}$)heterocycloalkyl, aryl($C_{1-5}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted.

In some particular variations, $R_1$ is a cyclic moiety and is substituted with a non-hydrogen substituent at a 2 or 3 position of the cycle. In some variation, the non-hydrogen substituent is selected from the group consisting of ($C_{1-10}$)alkyl, ($C_{3-12}$)cycloalkyl, ($C_{3-12}$)heterocycloalkyl, aryl($C_{1-5}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, amino, aryl, heteroaryl, hydroxy, alkoxy, aryloxy, heteroaryloxy, carbonyl group, cyano, nitro, halo, imino group, sulfonyl group and sulfinyl group, each substituted or unsubstituted.

In some other variations, $R_1$ is selected from the group consisting of:

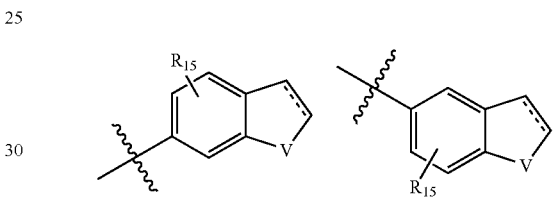

where
V is selected from the group consisting of S, O, and NR$_{16}$;
$R_{15}$ is selected from the group consisting of hydrogen, halo, ($C_{1-10}$)perhaloalkyl, amino, nitro, cyano, thio, sulfonamido, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, carbonyl group, imino group, sulfonyl group and sulfinyl group, each substituted or unsubstituted; and $R_{16}$ is selected from the group consisting of hydrogen, ($C_{1-10}$)perhaloalkyl, amino, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{8-12}$)heterobicycloaryl, carbonyl($C_{1-3}$)alkyl, thiocarbonyl($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In other variations, $R_1$ is selected from the group consisting of unsubstituted aryl, unsubstituted heteroaryl, haloaryl, haloheteroaryl, dihaloaryl and dihaloheteroaryl.

In other variations, $R_1$ is selected from the group consisting of unsubstituted phenyl, halophenyl and dihalophenyl.

In other variations, $R_1$ is selected from the group consisting of (2-cyano)phenyl; (3-cyano)phenyl; (2-hydroxy)phenyl; (3-hydroxy)phenyl; (2-alkenyl)phenyl; (3-alkenyl)phenyl; (2-alkynyl)phenyl; (3-alkynyl)phenyl; (2-methoxy)phenyl; (3-methoxy)phenyl; (2-nitro)phenyl; (3-nitro)phenyl; (2-carboxy)phenyl; (3-carboxy)phenyl; —(CH$_2$)-(2-carboxamido)phenyl; (3-carboxamido)phenyl; (2-sulfonamido)phenyl; (3-sulfonamido)phenyl; (2-tetrazolyl)phenyl; (3-tetrazolyl)

phenyl; (2-aminomethyl)phenyl; (3-aminomethyl)phenyl; (2-hydroxymethyl)phenyl; (3-hydroxymethyl)phenyl; (2-phenyl)phenyl; (3-phenyl)phenyl; (2-halo)phenyl; (3-halo)phenyl; (2-CONH$_2$)phenyl; (3-CONH$_2$)phenyl; (2-CONH(C$_{1-7}$)alkyl)phenyl; (3-CONH(C$_{1-7}$)alkyl)phenyl; (2-CO$_2$(C$_{1-7}$)alkyl)phenyl; (3-CO$_2$(C$_{1-7}$)alkyl)phenyl; (2-NH$_2$)phenyl; (3-NH$_2$)phenyl; (2-(C$_{3-7}$)alkyl)phenyl; (3-(C$_{3-7}$)alkyl)phenyl; (2-(C$_{3-7}$)cycloalkyl)phenyl; (3-(C$_{3-7}$)cycloalkyl)phenyl; (2-aryl)phenyl; (3-aryl)phenyl; (2-heteroaryl)phenyl; (3-heteroaryl)phenyl; 2-bromo-5-fluoro phenyl; 2-chloro-5-fluoro phenyl; 2-cyano-5-fluoro phenyl; 2,5-dichloro phenyl; 2,5-difluoro phenyl; 2,5-dibromo phenyl; 2-bromo-3,5-difluoro phenyl; 2-chloro-3,5-difluoro phenyl; 2,3,5-trifluoro phenyl; 2,3,5,6-tetrafluorophenyl; 2-bromo-3,5,6-trifluoro phenyl; 2-chloro-3,5,6-trifluoro phenyl; 2-cyano-3,5-difluoro phenyl; 2-cyano-3,5,6-trifluoro phenyl; (2-heterocycloalkyl)phenyl; and (3-heterocycloalkyl)phenyl, each substituted or unsubstituted.

In other variations, R$_1$ is selected from the group consisting of:

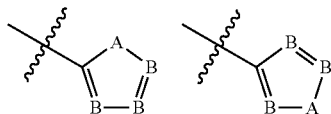

wherein:

A is S, O or NR$_{17}$;

B is CR$_{18}$ or N;

R$_{17}$ is selected from the group consisting of hydrogen, (C$_{1-10}$)perhaloalkyl, amino, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{8-12}$)heterobicycloaryl, carbonyl(C$_{1-3}$)alkyl, thiocarbonyl(C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and each R$_{18}$ is independently selected from the group consisting of hydrogen, halo, (C$_{1-10}$)perhaloalkyl, amino, thio, cyano, CF$_3$, nitro, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{8-12}$)heterobicycloaryl, carbonyl(C$_{1-3}$)alkyl, thiocarbonyl(C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted, or R$_{17}$ and R$_{18}$, or two R$_{18}$ are taken together to form an unsubstituted or substituted ring.

In other variations, R$_1$ is selected from the group consisting of:

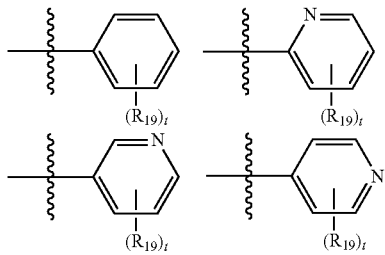

wherein t is 0, 1, 2, 3, 4 or 5; and each R$_{19}$ is independently selected from the group consisting of halo, (C$_{1-10}$)perhaloalkyl, CF$_3$, (C$_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted, or two R$_{19}$ are taken together to form an unsubstituted or substituted ring.

In other variations, R$_1$ is selected from the group consisting of:

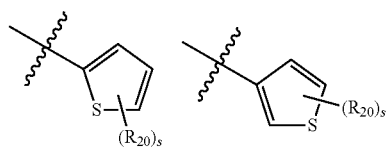

wherein:

s is 0, 1, 2, or 3; and each R$_{20}$ is independently selected from the group consisting of halo, (C$_{1-10}$)perhaloalkyl, CF$_3$, (C$_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted, or two R$_{20}$ are taken together to an unsubstituted or substituted form a ring.

In still other variations, wherein R$_1$ is an aryl substituted with one or more substituents independently selected from the group consisting of halo, hydroxy(C$_{1-6}$)alkyl, amino(C$_{1-6}$)alkyl, and (C$_{1-6}$)alkoxy, provided that any two substituents on adjacent ring atoms of said aryl may be taken together to form a five or six membered ring.

In still other variations, R$_1$ is a phenyl substituted with one or more substituents each independently selected from the group consisting of hydroxyl, halo, cyano, (C$_{1-10}$)alkyl, (C$_{1-6}$)alkoxy, aryloxy, hydroxyl(C$_{1-6}$)alkyl, amido, and amino(C$_{1-6}$)alkyl, each substituted or unsubstituted, provided that any two substituents on adjacent ring atoms of said phenyl may be taken together to form a five- or six-membered ring.

In still other variations, R$_1$ is selected from the group consisting of

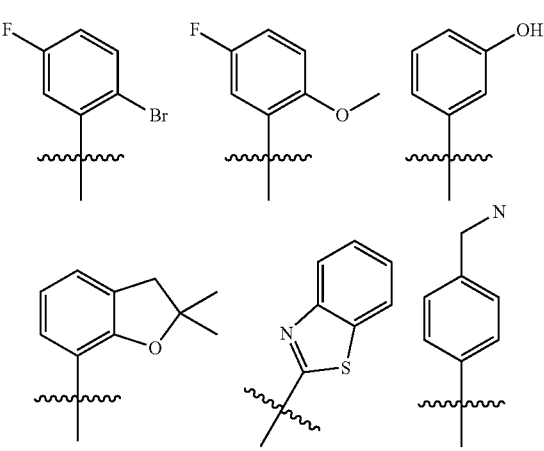

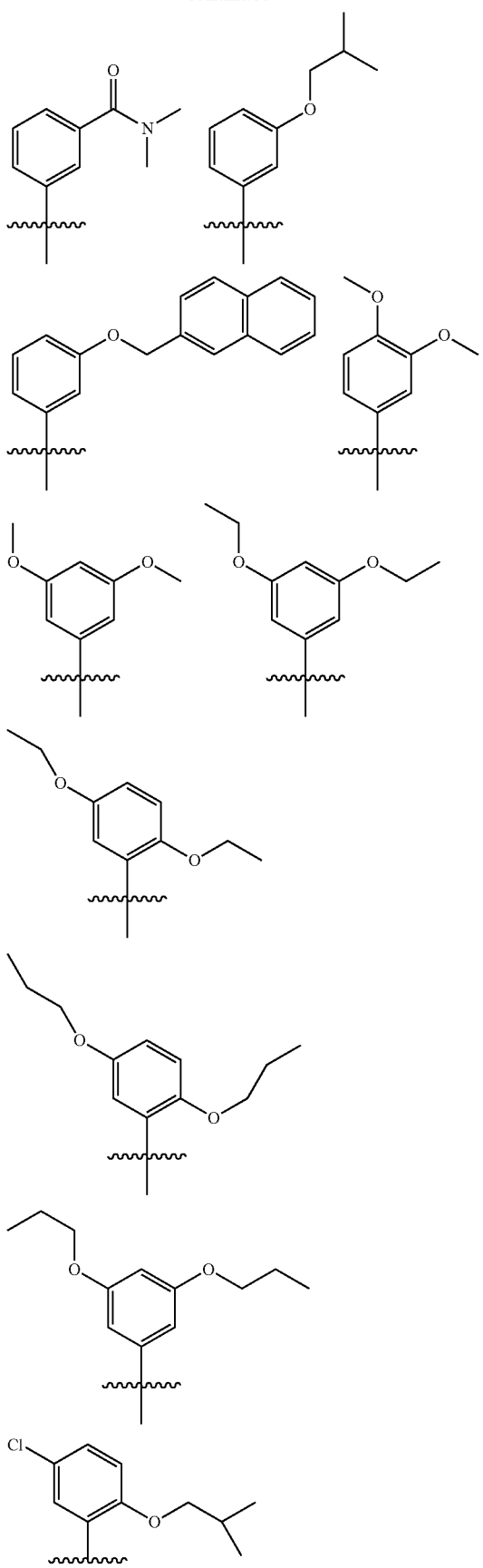

Particular examples of renin inhibitors according to the present invention include, but are not limited to:

6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(3-hydroxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;

7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;

6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;

6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;

6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;

7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;

6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;

6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;

3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;

6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;

6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;

6-(Aminomethyl)-1,3-dimethyl-7-(naphthalen-2-ylmethylamino)-5-(2-phenoxyphenyl)pyrido[2,3-d]pyrimidine-2,4(1H,3H)-dione;

6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(Aminomethyl)-5-(3-fluorophenyl)-1,3-dimethyl-7-(naphthalen-2-ylmethylamino)pyrido[2,3-d]pyrimidine-2,4(1H,3H)-dione;

6-(Aminomethyl)-5-(3-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(3-phenylpropylamino)pyrido[2,3-d]pyrimidine-2,4(1H,3H)-dione;

6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(2-bromo-5-fluorophenyl)-7-(1,2-diphenylethylamino)-1,3-dimethylpyrido[2,3-d]pyrimidine-2,4(1H,3H)-dione;

6-(Aminomethyl)-5-(5-fluoro-2-methoxyphenyl)-7-(3-methoxybenzylamino)-1,3-dimethylpyrido[2,3-d]pyrimidine-2,4(1H,3H)-dione;

6-(Aminomethyl)-5-(5-fluoro-2-methoxyphenyl)-7-(3-isobutoxybenzylamino)-1,3-dimethylpyrido[2,3-d]pyrimidine-2,4(1H,3H)-dione;

5-(3,5-Dimethoxyphenyl)-6-((methylamino)methyl)-1,3-dimethyl-7-(naphthalen-2-ylmethylamino)pyrido[2,3-d]pyrimidine-2,4(1H,3H)-dione;

6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione;

6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(phenethylamino)pyrido[2,3-d]pyrimidine-2,4(1H,3H)-dione;

6-(Aminomethyl)-5-(2-bromo-5-fluorophenyl)-7-(4-(ethylamino)phenylthio)-1,3-dimethylpyrido[2,3-d]pyrimidine-2,4(1H,3H)-dione;

N-(4-(6-(Aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide;

6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione;

5-(3,5-Dimethoxyphenyl)-6-((ethylamino)methyl)-1,3-dimethyl-7-(naphthalen-2-ylmethylamino)pyrido[2,3-d]pyrimidine-2,4(1H,3H)-dione;

6-(Aminomethyl)-5-(2,4-dichlorophenyl)-7-(2,5-dipropoxybenzylamino)-1-methylpyrido[2,3-d]pyrimidine-2,4(1H,3H)-dione;

6-(Aminomethyl)-5-(benzo[d]thiazol-2-yl)-1,3-dimethyl-7-(naphthalen-2-ylmethylamino)pyrido[2,3-d]pyrimidine-2,4(1H,3H)-dione;

6-(aminomethyl)-7-(1,2-diphenylethylamino)-5-(5-fluoro-2-methoxyphenyl)-1,3-dimethylpyrido[2,3-d]pyrimidine-2,4(1H,3H)-dione;

6-(aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione; and 6-(aminomethyl)-7-(bis(naphthalen-2-ylmethyl)amino)-5-(3-hydroxyphenyl)-1,3-dimethylpyrido[2,3-d]pyrimidine-2,4(1H,3H)-dione.

It is noted that the compounds of the present invention may be in the form of a pharmaceutically acceptable salt. It is further note that the compounds of the present invention may be in a mixture of stereoisomers, or the compound may comprise a single stereoisomer.

In another aspect, the present invention is related to a pharmaceutical composition comprising as an active ingredient a compound according to any one of the above embodiments and variations. In one embodiment, the composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In another embodiment, the pharmaceutical composition comprises a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the invention is related to a kit which comprises a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another aspect, the invention is related to an article of manufacture comprising a compound of any one of the above embodiments and variations and packaging materials. In one embodiment, the packaging material comprises a container for housing the compound. In another embodiment, the container comprises a label indicating one or more members of the group consisting of a disease state for which the compound is to be administered, storage information, dosing information and/or instructions regarding how to administer the compound. In another embodiment, the article of manufacture comprises the compound in a multiple dose form.

Another aspect of the invention relates to therapeutic methods using the compounds of the invention to inhibit renin or to prevent or treat conditions mediate by renin.

In one embodiment, the method comprises causing a compound of any one of the above embodiments and variations to be present in a subject in order to inhibit renin in vivo.

In another embodiment, the method comprises administering a first compound to a subject that is converted in vivo to a second compound wherein the second compound inhibits renin in vivo, the second compound being a compound according to any one of the above embodiments and variations.

Another embodiment is a method of treating a disease state for which renin possesses activity contributes to the pathology and/or symptomology of the disease state. In one variation, the method comprises causing a compound of any one of the above embodiments and variations to be present in a subject in a therapeutically effective amount for the disease state. In another variation, the method comprises administering a compound of any one of the above embodiments and variations to a subject, wherein the compound is present in the subject in a therapeutically effective amount for the disease state. In a further variation, the method comprises administering a first compound to a subject that is converted in vivo to a second compound wherein the second compound inhibits renin in vivo, the second compound being a compound according to any one of the above embodiments and variations.

In one variation of the above embodiments and variations, the disease state is selected from the group consisting of cardiovascular disease, hypertension, congestive heart failure, myocardial infarction, renal protection, inflammation, neurological disease and cancer.

In one particular embodiment, the method is for treating hypertension.

In one embodiment, the compounds, compositions, kits and articles of manufacture are used to treat a disease state for which renin possess activity that contributes to the pathology and/or symptomology of the disease state. In another embodiment, a compound is administered to a subject wherein renin activity within the subject is altered, preferably reduced.

In another embodiment, a prodrug of a compound is administered to a subject that is converted to the compound in vivo where it inhibits renin.

In another aspect, the invention is related to therapeutic methods using the compounds of the invention to inhibit both renin and DPP-IV to prevent or treat conditions mediate by renin and DPPIV.

In one particular embodiment, the method is a combination therapy for preventing and/or treating diabetes related hypertension.

In all the above embodiments and variations of the therapy methods of the invention, the first compounds or the second compounds are of the formula:

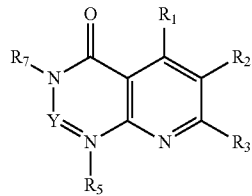

In some variations of the above embodiments and variations of the therapy methods of the invention, the first compounds or the second compounds are of the formula:

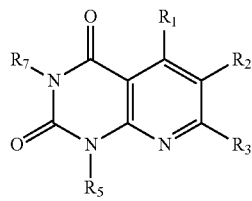

In other variations of the above embodiments and variations of the therapy methods of the invention, the first compounds or the second compounds are of the formula:

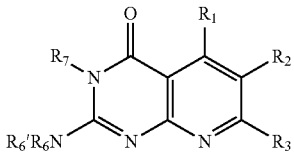

In still other variations of the above embodiments and variations of the therapy methods of the invention, the first compounds or the second compounds are of the formula:

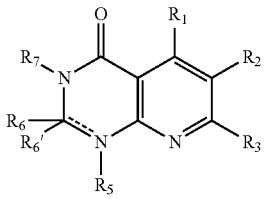

In all the above variations of the first and second compounds for the therapy methods of the invention:

Y is selected from the group consisting of —C(O)—, —C(S)—, —S(O)—, —S(O)$_2$—, —C(R$_6$)(R$_{6'}$)—, and —C(NR$_6$R$_{6'}$)—;

R$_1$ is selected from the group consisting of (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;

R$_2$ is selected from the group consisting of amino(C$_{1-6}$)alkyl, (C$_{3-12}$)heterocycloalkyl, (C$_{4-12}$)heterobicycloaryl, heteroaryl, and cyano, each substituted or unsubstituted;

R$_3$ is selected from the group consisting of hydrogen, hydroxyl, halo, (C$_{1-10}$)perhaloalkyl, amino, nitro, cyano, thio, oxy, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, (C$_{1-10}$)alkylamino, amino(C$_{1-10}$)alkyl, aryl, heteroaryl, hydroxy, alkoxy, aryloxy, heteroaryloxy, carbonyl group, imino group, sulfonyl group and sulfinyl group, each substituted or unsubstituted; or R$_2$ and R$_3$ are taken together to form a ring;

R$_5$ and R$_7$ are each independently selected from the group consisting of hydrogen, (C$_{1-10}$)haloalkyl, amino, nitro, thio, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, (C$_{3-12}$)cycloalkyl(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or R$_5$ is absent when the nitrogen atom to which R$_5$ is drawn forms part of a double bond; and R$_6$ and R$_{6'}$ are each independently selected from the group consisting of hydrogen, nitro, sulfonamido, (C$_{1-10}$)alkyl, (C$_{1-10}$)azaalkyl, (C$_{1-10}$)oxaalkyl, (C$_{1-10}$)oxo alkyl, hydroxy (C$_{1-10}$)alkyl, (C$_{3-12}$)cycloalkyl, (C$_{1-12}$)heterocycloalkyl, aryl (C$_{1-10}$)alkyl, (C$_{1-5}$)heteroarylalkyl, (C$_{9-12}$)bicycloaryl, (C$_{4-12}$)heterobicycloaryl, (C$_{3-12}$)cycloalkyl(C$_{1-10}$)alkyl, (C$_{3-12}$)heterocycloalkyl(C$_{1-10}$)alkyl, carbonyl(C$_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, oxy group, carbonyl group, amino group, imino group, thio group, sulfonyl group and sulfinyl group, each substituted or unsubstituted, or $R_5$ and $R_6$ are taken together to form a ring, or $R_{6'}$ is absent when the carbon or nitrogen atom on which $R_{6'}$ is drawn forms part of a double bond, or when Y is $CR_6R_{6'}$, $R_6$ and $R_{6'}$ is taken together to form an oxo or a thioxo group.

$R_6$ and $R_{6'}$

The some variations of the compounds or second compounds of the therapy method, $R_6$ and $R_{6'}$, when present, are each independently selected from the group consisting of hydrogen, hydroxy, alkoxy, aryloxy, ($C_{1-10}$)alkyl, ($C_{1-10}$)azaalkyl, ($C_{1-10}$)oxaalkyl, ($C_{1-10}$)oxoalkyl, hydroxy($C_{1-10}$)alkyl, aryl, heteroaryl, ($C_{3-7}$)cycloalkyl, hetero($C_{1-6}$)cycloalkyl, aryl($C_{1-5}$)alkyl, heteroaryl($C_{1-5}$)alkyl, ($C_{3-7}$)cycloalkyl($C_{1-5}$)alkyl, hetero($C_{1-6}$)cycloalkyl($C_{1-5}$)alkyl, oxy group, carbonyl group, amino group, thio group, sulfonyl group and sulfinyl group, each substituted or unsubstituted; or $R_5$ and $R_6$ are taken together to form a ring, or $R_{6'}$ is absent when the atom on which $R_{6'}$ is bound forms part of a double bond, or when Y is $CR_6R_{6'}$, $R_6$ and $R_{6'}$ is taken together to form an oxo or a thioxo group.

In some particular variations of the compounds or second compounds of the therapy method, $R_6$ is -L-$(CH_2)_n$—$R_{22}$ and $R_{6'}$ is hydrogen or is absent,
where
n is 0, 1, 2 or 3;
L is absent or is selected from the group consisting of —$CR_{23}R_{23'}$—, —O—, —S—, and —$NR_{23}$, where $R_{23}$ and $R_{23'}$ are each independently selected from the group consisting of hydrogen, alkoxy, alkyl, aryl, ($C_{1-6}$)heteroaryl, ($C_{3-6}$)cycloalkyl, and ($C_{1-6}$)heterocycloalkyl, each unsubstituted or substituted; and
$R_{22}$ is selected from the group consisting of aryl, heteroaryl, ($C_{3-7}$)cycloalkyl and ($C_{1-6}$)heterocycloalkyl, each unsubstituted or substituted.

In the preceding variations of the compounds or second compounds, $R_{22}$ is phenyl.

In some variations of the compounds or second compounds of the therapy method, $R_5$ and $R_7$ are each independently selected from the group consisting of hydrogen, ($C_{1-10}$)haloalkyl and ($C_{1-10}$)alkyl, each substituted or unsubstituted. In other variations, $R_5$ and $R_7$ are each independently selected from the group consisting of hydrogen and ($C_{1-6}$)alkyl. In still other variations, $R_5$ is hydrogen or methyl. In still other variations, $R_7$ is hydrogen or methyl. In still other variations, $R_5$ and $R_7$ are both methyl.

$R_2$

In all the above variations of the first compounds or second compound of the invention, $R_2$ is —$CH_2NH_2$. In other variations, $R_2$ is —$(CR_8R_9)_qNR_{10}R_{11}$;
where
q is 1, 2 or 3;
$R_8$ and $R_9$ are each independently selected from the group consisting of hydrogen, halogen, ($C_{1-10}$)perhaloalkyl, cyano, nitro, alkyl, cycloalkyl, alkene, alkyne, aryl, and heteroaryl, each substituted or unsubstituted, or where $R_8$ and $R_9$ are taken together to form a substituted or unsubstituted ring; and
$R_{10}$ and $R_{11}$ are each independently selected from the group consisting of hydrogen, ($C_{1-10}$)haloalkyl, amino, thio, ($C_{1-10}$)alkyl, ($C_{3-12}$)cycloalkyl, ($C_{3-12}$)heterocycloalkyl, hydroxylalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, and imino group, each substituted or unsubstituted, or $R_{10}$ and $R_{11}$ are taken together to form a ring.

In some variations of the preceding variations, q is 3. In other variations, q is 2. In still other variations, q is 1.

In some variations of the variations where $R_2$ is —$(CR_8R_9)_q NR_{10}R_{11}$, $R_8$ and $R_9$ are each independently selected from the group consisting of hydrogen, ($C_{1-10}$)haloalkyl, cyano, alkyl, each substituted or unsubstituted. In other variations, $R_8$ is selected from the group consisting of hydrogen and alkyl. In other variations, $R_9$ is selected from the group consisting of hydrogen and alkyl. In other variations, $R_8$ and $R_9$ are both hydrogen. In other variations, $R_{10}$ and $R_{11}$ are each independently selected from the group consisting of hydrogen, ($C_{1-6}$)alkyl, ($C_{3-6}$)cycloalkyl($C_{1-3}$)alkyl, ($C_{1-5}$)heterocycloalkyl($C_{1-3}$)alkyl, hydroxyalkyl, ($C_6$)aryl($C_{1-3}$)alkyl, ($C_{1-5}$)heteroaryl($C_{1-3}$)alkyl, ($C_{3-6}$)cycloalkyl, ($C_{1-5}$)heterocycloalkyl, ($C_6$)aryl, ($C_{1-5}$)heteroaryl, each substituted or unsubstituted. In still other variations, $R_{10}$ and $R_{11}$ are each independently selected from the group consisting of hydrogen and substituted or unsubstituted ($C_{1-6}$)alkyl. In still other variations, $R_{10}$ and $R_{11}$ are each independently selected from the group consisting of hydrogen and ($C_{1-6}$)alkyl, each unsubstituted or substituted with one or more substituents each independently selected from the group consisting of alkyl, alkyoxy, hydroxyl, cyano and halo. In some variations of the variations where $R_2$ is —$(CR_8R_9)_9NR_{10}R_{11}$, $R_{10}$ and $R_{11}$ are each independently selected from the group consisting of hydrogen, methyl and hydroxylethyl. In other variations, one of $R_{10}$ and $R_{11}$ is hydroxyl substituted ethyl. In other variations, $R_{10}$ and $R_{11}$ are both methyl. In other variations, one of $R_{10}$ and $R_{11}$ is hydrogen. In other variations, $R_{10}$ and $R_{11}$ are both hydrogen.

$R_3$

In some variations of the first compounds or second compounds of the therapy method, $R_3$ is —S—$R_{12}$, where $R_{12}$ is selected from the group consisting of alkyl, phenyl, phenylalkyl, naphthylalkyl, each substituted or unsubstituted.

In other variations, $R_3$ is —N($R_{13}$)—$R_{12}$, where $R_{12}$ and $R_{13}$ are independently selected from the group consisting of hydrogen, ($C_{1-10}$)haloalkyl, amino, thio, ($C_{1-10}$)alkyl, ($C_{3-12}$)cycloalkyl, ($C_{3-12}$)heterocycloalkyl, aryl($C_{1-10}$)alkyl, heteroaryl($C_{1-5}$)alkyl, ($C_{9-12}$)bicycloaryl, ($C_{4-12}$)heterobicycloaryl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, hydroxy, alkoxy, aryloxy, heteroaryloxy, and imino group, each substituted or unsubstituted.

In the variation where $R_3$ is —N($R_{13}$)—$R_{12}$, in some variations, $R_{13}$ is selected from the group consisting of hydrogen, ($C_{1-10}$)alkyl, ($C_{1-10}$)haloalkyl, hydroxyl($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{3-12}$)cycloalkyl($C_{1-5}$)alkyl, ($C_{3-12}$)heterocycloalkyl($C_{1-10}$)alkyl, aryl($C_{1-10}$)alkyl, ($C_{1-10}$)heteroaryl($C_{1-5}$)alkyl, ($C_{1-10}$)heteroalkyl, each substituted or unsubstituted. In other variations, $R_{13}$ is selected from the group consisting of hydrogen and ($C_{1-4}$)alkyl. In still other variations, $R_{13}$ is hydrogen.

In the variation where $R_3$ is —N($R_{13}$)—$R_{12}$, in some variations, $R_{12}$ is selected from the group consisting of phenyl, phenylalkyl or naphthylalkyl, each unsubstituted or substituted. In some variations, the phenyl rings and the naphthyl rings are each independently unsubstituted or substituted with one or more substituents independently selected from the group consisting of halo, nitro, cyano, thio, oxy, hydroxy, carbonyloxy, ($C_{1-10}$)alkoxy, ($C_{4-12}$)aryloxy, ($C_{1-10}$)heteroaryl oxy, carbonyl, oxycarbonyl, aminocarbonyl, amino, ($C_{1-10}$)alkylamino, sulfonamido, imino, sulfonyl, sulfinyl, ($C_{1-10}$)alkyl, ($C_{1-10}$)haloalkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, ($C_{3-12}$)heterocycloalkyl($C_{1-10}$)alkyl, aryl($C_{1-10}$)alkyl, ($C_{1-10}$)heteroaryl($C_{1-5}$)alkyl, ($C_{9-12}$)bicycloaryl($C_{1-5}$)alkyl, ($C_{8-12}$)heterobicycloaryl($C_{1-5}$)alkyl, ($C_{1-10}$)heteroalkyl, ($C_{3-12}$)cycloalkyl, ($C_{3-12}$)heterocycloalkyl, ($C_{9-12}$)bicycloalkyl, ($C_{3-12}$)heterobicycloalkyl, ($C_{4-12}$)aryl, ($C_{1-10}$)heteroaryl, ($C_{9-12}$)bicycloaryl and ($C_{4-12}$)heterobicycloaryl, each unsubstituted or further substituted. In still other variations, the phenyl rings and the naphthyl ring are independently unsubstituted or substituted with one or more substituents selected from the group consisting of —$CF_3$, —$OCH3$, —$OCH_2CH(CH_3)_2$, —$NH$—$CH_2CH_3$, —$NHC(O)CH_3$, —$OCH_2CH_2CH_3$, —$C(O)NCH_2CH_2CH_3$, benzyloxy,

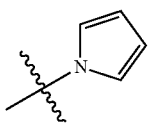

and

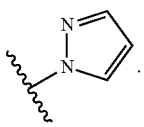

In still other variations, the phenyl rings and naphthyl ring are independently substituted with —$OCH_2CH_2CH_3$ or —$C(O)NCH_2CH_2CH_3$.

In other variations, where $R_{12}$ is selected from the group consisting of phenyl, phenylalkyl or naphthylalkyl, the alkyl of the phenylalkyl or the naphthylalkyl is a $C_1$alkyl. In other variations, the alkyl of the phenylalkyl or the naphthylalkyl is a $C_2$alkyl. In other variations, the alkyl of the phenylalkyl or the naphthylalkyl is a $C_3$alkyl. In still other variations, the alkyl of the phenylalkyl or the naphthylalkyl is unsubstituted or is substituted with one or more substituents each independently selected from the group consisting of hydroxyl, ($C_{1-10}$)alkoxy, ($C_{4-12}$)aryloxy, amino, ($C_{1-10}$)alkyl, hydroxy($C_{1-10}$)alkyl, ($C_{1-10}$)azaalkyl, ($C_{1-10}$)oxaalkyl, ($C_{4-12}$)aryl, ($C_{1-10}$)heteroaryl, ($C_{3-12}$)cycloalkyl, ($C_{3-12}$)heterocycloalkyl, ($C_{3-12}$)cycloalkyl($C_{1-5}$)alkyl, ($C_{3-12}$)heterocycloalkyl($C_{1-10}$)alkyl, aryl($C_{1-10}$)alkyl and ($C_{1-10}$)heteroaryl($C_{1-5}$)alkyl, each substituted or unsubstituted. In still other variations, the alkyl of the phenylalkyl or naphthylalkyl is unsubstituted or is substituted with a phenyl. In yet still other variations, the alkyl of the phenylalkyl or naphthylalkyl is unsubstituted.

In still other variations, $R_{12}$ is ($C_{3-6}$)alkyl, unsubstituted or substituted with one or more substituents independently selected from the group consisting of hydroxyl, alkoxy, alkyl, alkyoxy, haloalkyl, cyano and halo. In other variations, $R_{12}$ is —$CH(CH_2CH_3)_2$. In still other variations, $R_{12}$ is selected from the group consisting of —$CH(CH_2CH_3)_2$,

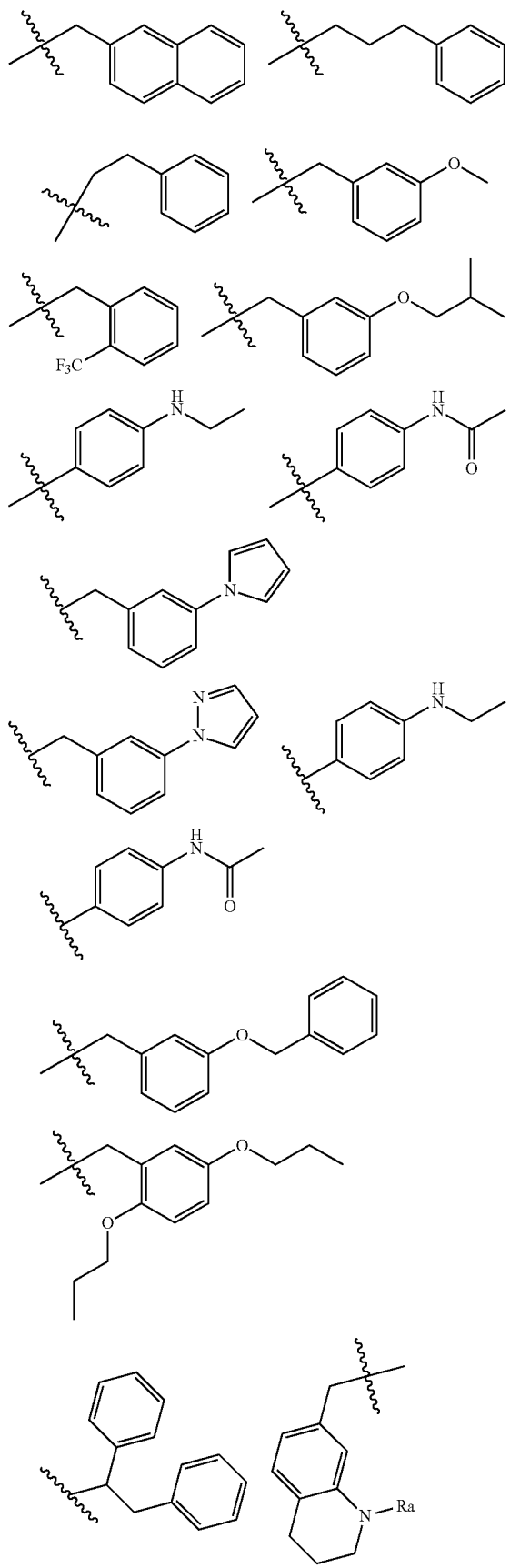

-continued

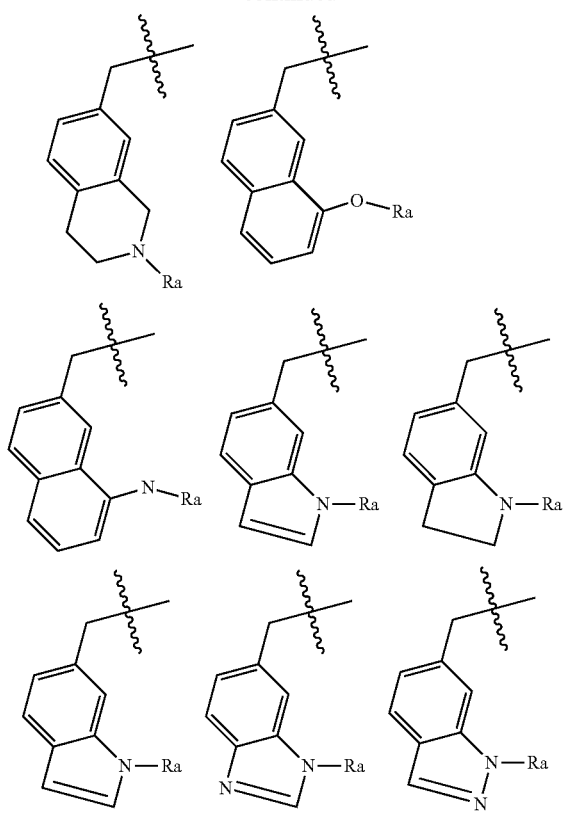

$R_a$ is selected from the group consisting of —(CH$_2$)$_2$OCH$_3$, —(CH$_2$)$_3$OCH$_3$, —(CH$_2$)$_2$NHC(O)CH$_3$, —(CH$_2$)$_3$NHC(O)CH$_3$,

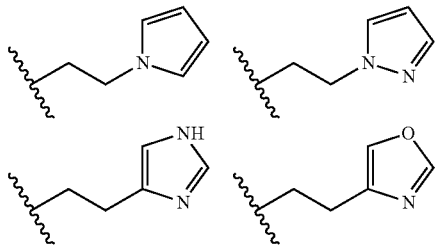

In still some other variations where $R_3$ is —N(R$_{13}$)—R$_{12}$, $R_{12}$ and $R_{13}$ are taken together to form a ring. In other variations, the ring formed by taking $R_{12}$ and $R_{13}$ together is a substituted or unsubstituted 3, 4, 5 or 6 membered ring. In still other variations, the ring formed by taking $R_{12}$ and $R_{13}$ together is a substituted or unsubstituted heterocycloalkyl, heterobicycloalkyl, aryl, heteroaryl, or (C$_{8-12}$)heterobicycloaryl.

$R_1$

In some variations of the compounds or second compounds of the therapy method, $R_1$ is a substituted or unsubstituted (C$_{3-7}$)cycloalkyl. In other variations, $R_1$ is a substituted or unsubstituted (C$_{3-7}$)heterocycloalkyl. In other variations, $R_1$ is a substituted or unsubstituted aryl. In still other variations, $R_1$ is a substituted or unsubstituted phenyl. In still other variations, $R_1$ is a substituted or unsubstituted heteroaryl.

In some further variations, $R_1$ is

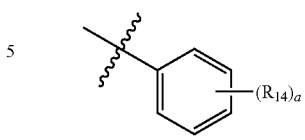

where
a is 0, 1, 2, 3, 4, or 5; and
$R_{14}$ is selected from the group consisting of hydrogen, halo, (C$_{1-10}$)perhaloalkyl, amino, nitro, cyano, thio, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted.

In other further variations, $R_1$ is a cyclic moiety and is substituted with a non-hydrogen substituent at a 2 or 3 position of the cycle, wherein the non-hydrogen substituent is selected from the group consisting of (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, amino, aryl, heteroaryl, hydroxy, alkoxy, aryloxy, heteroaryloxy, carbonyl group, cyano, nitro, halo, imino group, sulfonyl group and sulfinyl group, each substituted or unsubstituted.

In some particular variations, $R_1$ is selected from the group consisting of:

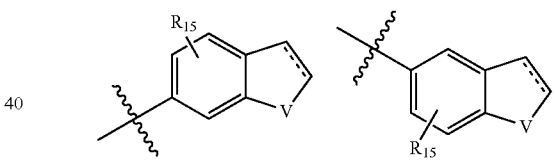

where
V is selected from the group consisting of S, O, and NR$_{16}$;
$R_{15}$ is selected from the group consisting of hydrogen, halo, (C$_{1-10}$)perhaloalkyl, amino, nitro, cyano, thio, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted; and $R_{16}$ is selected from the group consisting of hydrogen, (C$_{1-10}$)perhaloalkyl, amino, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{8-12}$)heterobicycloaryl, carbonyl (C$_{1-3}$)alkyl, thiocarbonyl(C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In some particular variations, $R_1$ is selected from the group consisting of unsubstituted aryl, unsubstituted heteroaryl, haloaryl, haloheteroaryl, dihaloaryl and dihaloheteroaryl. In other particular variations, $R_1$ is selected from the group consisting of an unsubstituted phenyl, halophenyl and dihalophenyl. In still other particular variations, $R_1$ is selected from the group consisting of (2-cyano)phenyl; (3-cyano)phenyl; (2-hydroxy)phenyl; (3-hydroxy)phenyl; (2-alkenyl)phenyl; (3-alkenyl)phenyl; (2-alkynyl)phenyl; (3-alkynyl)phenyl; (2-methoxy)phenyl; (3-methoxy)phenyl; (2-nitro)phenyl; (3-nitro)phenyl; (2-carboxy)phenyl; (3-carboxy)phenyl; —(CH$_2$)-(2-carboxamido)phenyl; (3-carboxamido)phenyl; (2-sulfonamido)phenyl; (3-sulfonamido)phenyl; (2-tetrazolyl)phenyl; (3-tetrazolyl)phenyl; (2-aminomethyl)phenyl; (3-aminomethyl)phenyl; (2-hydroxymethyl)phenyl; (3-hydroxymethyl)phenyl; (2-phenyl)phenyl; (3-phenyl)phenyl; (2-halo)phenyl; (3-halo)phenyl; (2-CONH$_2$)phenyl; (3-CONH$_2$)phenyl; (2-CONH(C$_{1-7}$)alkyl)phenyl; (3-CONH(C$_{1-7}$)alkyl)phenyl; (2-CO$_2$(C$_{1-7}$)alkyl)phenyl; (3-CO$_2$(C$_{1-7}$)alkyl)phenyl; (2-NH$_2$)phenyl; (3-NH$_2$)phenyl (2-(C$_{3-7}$)alkyl)phenyl; (3-(C$_{3-7}$)alkyl)phenyl; (2-(C$_{3-7}$)cycloalkyl)phenyl; (3-(C$_{3-7}$)cycloalkyl)phenyl; (2-aryl)phenyl; (3-aryl)phenyl; (2-heteroaryl)phenyl; (3-heteroaryl)phenyl; 2-bromo-5-fluorophenyl; 2-chloro-5-fluorophenyl; 2-cyano-5-fluorophenyl; 2,5-dichlorophenyl; 2,5-difluorophenyl; 2,5-dibromophenyl; 2-bromo-3,5-difluorophenyl; 2-chloro-3,5-difluorophenyl; 2,3,5-trifluorophenyl; 2,3,5,6-tetrafluorophenyl; 2-bromo-3,5,6-trifluorophenyl; 2-chloro-3,5,6-trifluorophenyl; 2-cyano-3,5-difluorophenyl; 2-cyano-3,5,6-trifluorophenyl; (2-heterocycloalkyl)phenyl; and (3-heterocycloalkyl)phenyl, each substituted or unsubstituted.

In some further variations, $R_1$ is selected from the group consisting of:

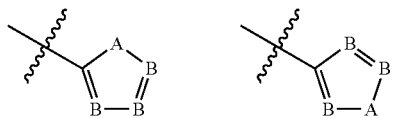

wherein:

A is S, O or NR$_{17}$;

B is CR$_{18}$ or N;

$R_{17}$ is independently selected from the group consisting of hydrogen, (C$_{1-10}$)perhaloalkyl, amino, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{8-12}$)heterobicycloaryl, carbonyl(C$_{1-3}$)alkyl, thiocarbonyl(C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and each $R_{18}$ is independently selected from the group consisting of hydrogen, halo, (C$_{1-10}$)perhaloalkyl, amino, thio, cyano, CF$_3$, nitro, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{8-12}$)heterobicycloaryl, carbonyl(C$_{1-3}$)alkyl, thiocarbonyl(C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted, or $R_{17}$ and $R_{18}$, or two $R_{18}$ are taken together to form an unsubstituted or substituted ring.

In other further variations, $R_1$ is selected from the group consisting of:

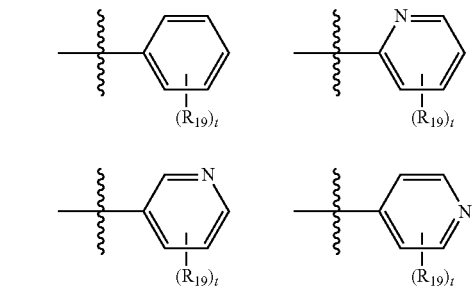

wherein t is 0, 1, 2, 3, 4 or 5; and each $R_{19}$ is independently selected from the group consisting of halo, (C$_{1-10}$)perhaloalkyl, CF$_3$, (C$_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted, or two $R_{19}$ are taken together to form an unsubstituted or substituted ring.

In other further variations, $R_1$ is selected from the group consisting of:

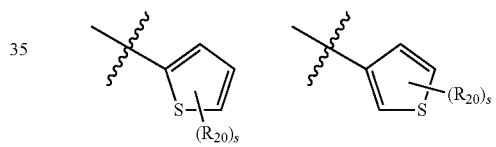

wherein:

s is 0, 1, 2, or 3; and each $R_{20}$ is independently selected from the group consisting of halo, (C$_{1-10}$)perhaloalkyl, CF$_3$, (C$_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted, or two $R_{20}$ are taken together to an unsubstituted or substituted form a ring.

In still other further variations, $R_1$ is an aryl substituted with one or more substituents independently selected from the group consisting of halo, hydroxy(C$_{1-6}$)alkyl, amino (C$_{1-6}$)alkyl, and (C$_{1-6}$)alkoxy, provided that any two substituents on adjacent ring atoms of said aryl may be taken together to form a five or six membered ring.

In still other variations, $R_1$ is a phenyl substituted with one or more substituents each independently selected from the group consisting of hydroxyl, halo, cyano, (C$_{1-10}$)alkyl, (C$_{1-6}$)alkoxy, aryloxy, hydroxyl(C$_{1-6}$)alkyl, amido, and amino(C$_{1-6}$)alkyl, each substituted or unsubstituted, provided that any two substituents on adjacent ring atoms of said phenyl may be taken together to form a five- or six-membered ring.

In still other further variations, $R_1$ is selected from the group consisting of

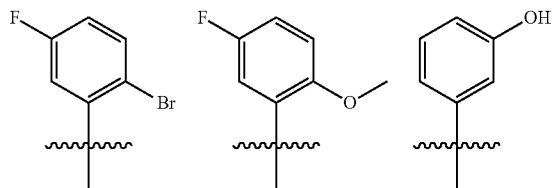
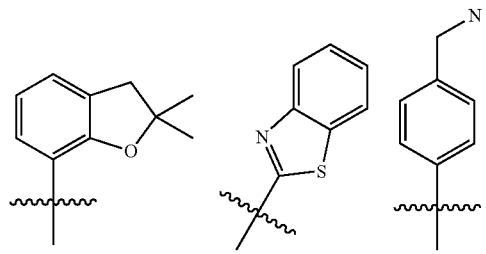
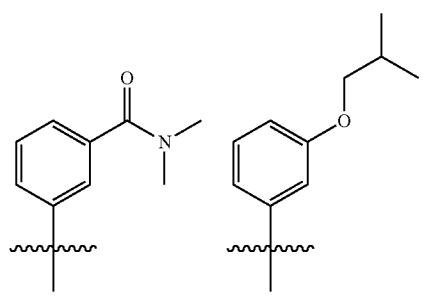
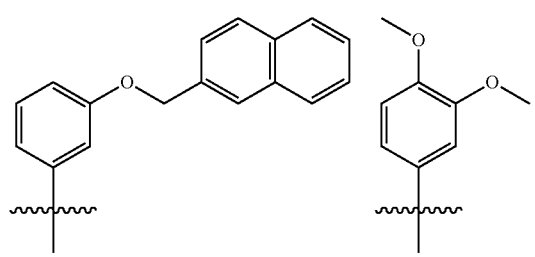
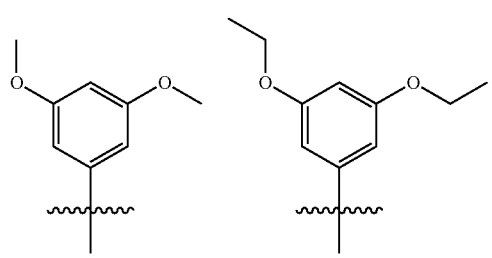
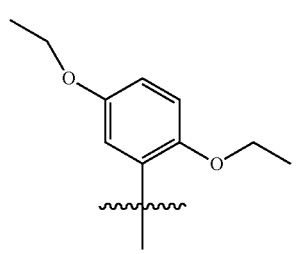

-continued

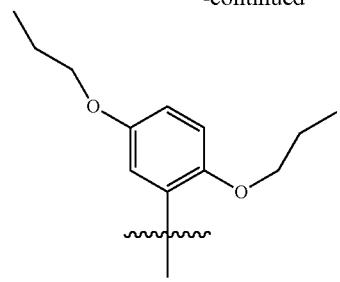
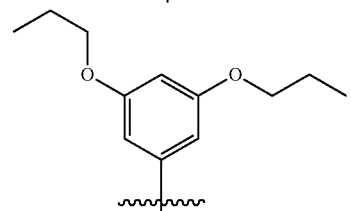
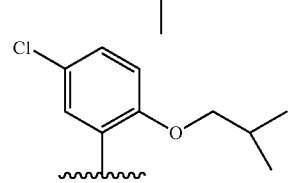
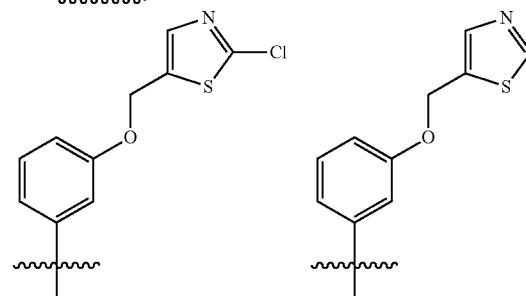
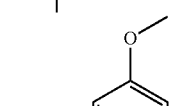
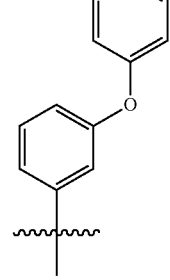
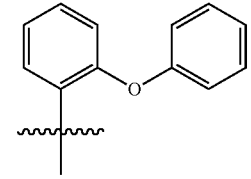

Examples of the compounds or the second compounds according to the present invention include, but are not limited to:

7-Amino-6-aminomethyl-5-(2,4-dichloro-phenyl)-1,3-dimethyl-1H-pyrido[2,3-d]pyrimidine-2,4-dione;
7-Amino-6-aminomethyl-5-(2-bromo-4-fluoro-phenyl)-1,3-dimethyl-1H-pyrido[2,3-d]pyrimidine-2,4-dione;
7-Amino-6-aminomethyl-5-(2-bromo-phenyl)-1,3-dimethyl-1H-pyrido[2,3-d]pyrimidine-2,4-dione;
6-Aminomethyl-5-(2,4-dichloro-phenyl)-7-ethylamino-1,3-dimethyl-1H-pyrido[2,3-d]pyrimidine-2,4-dione;
6-Aminomethyl-5-(2,4-dichloro-phenyl)-1,3-dimethyl-7-methylamino-1H-pyrido[2,3-d]pyrimidine-2,4-dione;
6-Aminomethyl-5-(2,4-dichloro-phenyl)-7-dimethylamino-1,3-dimethyl-1H-pyrido[2,3-d]pyrimidine-2,4-dione;

7-Hydroxy-5-(2-bromo-5-fluoro-phenyl)-1,3-dimethyl-2,4-dioxo-1,2,3,4-tetrahydropyrido[2,3-d]pyrimidine-6-carbonitrile;
6-Aminomethyl-5-(2-bromo-5-fluoro-phenyl)-7-hydroxy-1,3-dimethyl-1H-pyrido[2,3-d]pyrimidine-2,4-dione;
7-Amino-5-(2,5-dichloro-phenyl)-1,3-dimethyl-2,4-dioxo-1,2,3,4-tetrahydropyrido[2,3-d]pyrimidine-6-carbonitrile;
7-Amino-6-aminomethyl-5-(2,5-dichloro-phenyl)-1,3-dimethyl-1H-pyrido[2,3-d]pyrimidine-2,4-dione;
7-Amino-6-aminomethyl-5-(2-bromo-5-fluoro-phenyl)-1,3-dimethyl-1H-pyrido[2,3-d]pyrimidine-2,4-dione;
7-Amino-6-aminomethyl-1,3-dimethyl-5-(3-methyl-thiophen-2-yl)-1H-pyrido[2,3-d]pyrimidine-2,4-dione;
7-Amino-6-aminomethyl-5-(2-chloro-phenyl)-1,3-dimethyl-1H-pyrido[2,3-d]pyrimidine-2,4-dione;
7-Amino-6-aminomethyl-5-(4-fluoro-phenyl)-1,3-dimethyl-1H-pyrido[2,3-d]pyrimidine-2,4-dione;
7-Amino-6-aminomethyl-5-(5-chloro-thiophen-2-yl)-1,3-dimethyl-1H-pyrido[2,3-d]pyrimidine-2,4-dione;
7-Amino-6-aminomethyl-5-(4-bromo-phenyl)-1,3-dimethyl-1H-pyrido[2,3-d]pyrimidine-2,4-dione;
7-Amino-6-aminomethyl-5-(2,3-dichloro-phenyl)-1,3-dimethyl-1H-pyrido[2,3-d]pyrimidine-2,4-dione;
7-Amino-6-aminomethyl-5-(2-chloro-6-fluoro-phenyl)-1,3-dimethyl-1H-pyrido[2,3-d]pyrimidine-2,4-dione;
7-Amino-6-aminomethyl-5-(3-methoxy-phenyl)-1,3-dimethyl-1H-pyrido[2,3-d]pyrimidine-2,4-dione;
7-Amino-6-aminomethyl-5-(2-methoxy-phenyl)-1,3-dimethyl-1H-pyrido[2,3-d]pyrimidine-2,4-dione;
7-Amino-6-aminomethyl-5-(2-chloro-3,6-difluoro-phenyl)-1,3-dimethyl-1H-pyrido[2,3-d]pyrimidine-2,4-dione;
7-Amino-6-aminomethyl-5-phenyl-1,3-dimethyl-1H-pyrido[2,3-d]pyrimidine-2,4-dione;
7-Amino-6-aminomethyl-5-(3-bromo-thiophen-2-yl)-1,3-dimethyl-1H-pyrido[2,3-d]pyrimidine-2,4-dione;
7-Amino-6-aminomethyl-5-(2-chloro-5-fluoro-phenyl)-1,3-dimethyl-1H-pyrido[2,3-d]pyrimidine-2,4-dione;
7-Amino-6-aminomethyl-5-(2-bromo-5-fluoro-phenyl)-1,3-dimethyl-1H-pyrido[2,3-d]pyrimidine-2,4-dione;
7-Amino-6-aminomethyl-5-(2-chloro-4-fluoro-phenyl)-1,3-dimethyl-1H-pyrido[2,3-d]pyrimidine-2,4-dione;
7-Amino-6-aminomethyl-5-cyclopentyl-1,3-dimethyl-1H-pyrido[2,3-d]pyrimidine-2,4-dione;
7-Amino-6-aminomethyl-1,3-dimethyl-5-pyridin-3-yl-1H-pyrido[2,3-d]pyrimidine-2,4-dione;
7-Amino-6-aminomethyl-5-(4,5-dimethyl-thiophen-2-yl)-1,3-dimethyl-1H-pyrido[2,3-d]pyrimidine-2,4-dione;
7-Amino-6-aminomethyl-5-(5-fluoro-2-nitro-phenyl)-1,3-dimethyl-1H-pyrido[2,3-d]pyrimidine-2,4-dione;
7-Amino-6-aminomethyl-1,3-dimethyl-5-(3-methyl-3H-imidazol-4-yl)-1H-pyrido[2,3-d]pyrimidine-2,4-dione;
7-Amino-6-aminomethyl-5-benzo[b]thiophen-2-yl-1,3-dimethyl-1H-pyrido[2,3-d]pyrimidine-2,4-dione;
7-Amino-6-aminomethyl-1,3-dimethyl-5-(3-methyl-benzo[b]thiophen-2-yl)-1H-pyrido[2,3-d]pyrimidine-2,4-dione;
6-(Aminomethyl)-5-(2,4-dichlorophenyl)-7-hydroxy-1,3-dimethylpyrido[2,3-d]pyrimidine-2,4(1H,3H)-dione;
6-(Aminomethyl)-7-chloro-5-(2,4-dichlorophenyl)-1,3-dimethylpyrido[2,3-d]pyrimidine-2,4(1H,3H)-dione;
7-Amino-6-(aminomethyl)-5-(2-chloro-5-fluorophenyl)-3-methylpyrido[2,3-d]pyrimidine-2,4(1H,3H)-dione;
7-Amino-6-(aminomethyl)-5-(2-(aminomethyl)phenyl)-1,3-dimethylpyrido[2,3-d]pyrimidine-2,4(1H,3H)-dione;
2-(7-Amino-6-(aminomethyl)-1,3-dimethyl-2,4-dioxo-1,2,3,4-tetrahydropyrido[2,3-d]pyrimidin-5-yl)benzonitrile;
7-Amino-5-(2-(aminomethyl)phenyl)-1,3-dimethyl-2,4-dioxo-1,2,3,4-tetrahydropyrido[2,3-d]pyrimidine-6-carbonitrile;
6-(Aminomethyl)-7-(cyclopropylmethylamino)-5-(2,4-dichlorophenyl)-1,3-dimethylpyrido[2,3-d]pyrimidine-2,4(1H,3H)-dione;
2-(7-Amino-6-(aminomethyl)-1-isobutyl-3-methyl-2,4-dioxo-1,2,3,4-tetrahydropyrido[2,3-d]pyrimidin-5-yl)benzonitrile;
6-(Aminomethyl)-5-(2,4-dichlorophenyl)-1,3-dimethylpyrido[2,3-d]pyrimidine-2,4(1H,3H)-dione;
7-Amino-6-(aminomethyl)-5-(2-chloro-5-(trifluoromethyl)phenyl)-1,3-dimethylpyrido[2,3-d]pyrimidine-2,4(1H,3H)-dione;
7-Amino-6-(aminomethyl)-5-(2-chloro-5-fluorophenyl)-1-methylpyrido[2,3-d]pyrimidine-2,4(1H, 3H)-dione;
7-Amino-6-(aminomethyl)-5-(2-bromo-5-fluorophenyl)-1-methylpyrido[2,3-d]pyrimidine-2,4(1H,3H)-dione;
2-(7-Amino-6-(aminomethyl)-1,3-dimethyl-2,4-dioxo-1,2,3,4-tetrahydropyrido[2,3-d]pyrimidin-5-yl)-4-fluorobenzonitrile;
2-(6-(Aminomethyl)-7-chloro-1,3-dimethyl-2,4-dioxo-1,2,3,4-tetrahydropyrido[2,3-d]pyrimidin-5-yl)-4-fluorobenzonitrile;
2-(6-(Aminomethyl)-1,3,7-trimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7-(trifluoromethyl)-1,2,3,4-tetrahydropyrido[2,3-d]pyrimidin-5-yl)-4-fluorobenzonitrile;
2-(6-(Aminomethyl)-1,3-dimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7-(2,2,2-trifluoroethylamino)-1,2,3,4-tetrahydropyrido[2,3-d]pyrimidin-5-yl)-4-fluorobenzonitrile;
2-(6-(Aminomethyl)-1,3-dimethyl-7-(methyl(2,2,2-trifluoroethyl)amino)-2,4-dioxo-1,2,3,4-tetrahydropyrido[2,3-d]pyrimidin-5-yl)-4-fluorobenzonitrile;
2-(6-(Aminomethyl)-7-(bis(trifluoromethyl)amino)-1,3-dimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7,8-imidazo[1,2-a]-1,2,3,4,7,8-hexahydropyrido[2,3-d]pyrimidin-5-yl)-5-chlorobenzonitrile;
2-(6-(Aminomethyl)-3-(cyclopropylmethyl)-1,7-dimethyl-2,4-dioxo-1,2,3,4-tetrahydropyrido[2,3-d]pyrimidin-5-yl)-5-chlorobenzonitrile;
6-(Aminomethyl)-5-(4-chloro-2-methoxyphenyl)-1,3,7-trimethylpyrido[2,3-d]pyrimidine-2,4(1H,3H)-dione;
2-(6-(Aminomethyl)-7-methoxy-1,3-dimethyl-2,4-dioxo-1,2,3,4-tetrahydropyrido[2,3-d]pyrimidin-5-yl)-5-chlorobenzonitrile;
2-(6-(Aminomethyl)-1,3-dimethyl-2,4-dioxo-7-(pyrrolidin-1-yl)-1,2,3,4-tetrahydropyrido[2,3-d]pyrimidin-5-yl)-5-chlorobenzonitrile;
6-(Aminomethyl)-5-(5-fluoro-2-methoxyphenyl)-1,3-dimethyl-7-morpholinopyrido[2,3-d]pyrimidine-2,4(1H,3H)-dione;
N-(6-(Aminomethyl)-5-(4-chloro-2-methoxyphenyl)-1,3-dimethyl-2,4-dioxo-1,2,3,4-tetrahydropyrido[2,3-d]pyrimidin-7-yl)methanesulfonamido;
2-(6-(Aminomethyl)-3-benzyl-7-methoxy-1-methyl-2,4-dioxo-1,2,3,4-tetrahydropyrido[2,3-d]pyrimidin-5-yl)-5-chlorobenzonitrile;

6-(Aminomethyl)-3-benzyl-5-(4-chloro-2-methoxyphenyl)-1-methyl-7-(trifluoromethyl)pyrido[2,3-d]pyrimidine-2,4(1H,3H)-dione;

6-(Aminomethyl)-5-(3,5-difluoro-2-methoxyphenyl)-1,3-dimethyl-7-(trifluoromethyl)pyrido[2,3-d]pyrimidine-2,4(1H,3H)-dione;

6-(Aminomethyl)-3-benzyl-5-(2-chloro-3,5-difluorophenyl)-1-methyl-7-(trifluoromethyl)pyrido[2,3-d]pyrimidine-2,4(1H,3H)-dione;

6-(Aminomethyl)-5-(2-bromo-3,5-difluorophenyl)-1,3-dimethyl-7-(trifluoromethyl)pyrido[2,3-d]pyrimidine-2,4(1H,3H)-dione;

6-(Aminomethyl)-5-(3,5-difluoro-2-methoxyphenyl)-1,2-imidazo-[1,2-a]-3-methyl-7-(trifluoromethyl)-2,3-dihydropyrido[2,3-d]pyrimidin-4(1H)-one;

6-(Aminomethyl)-5-(3,5-difluoro-2-methoxyphenyl)-3-methyl-2-(methylamino)-7-(trifluoromethyl)pyrido[2,3-d]pyrimidin-4(3H)-one;

2-Amino-6-(aminomethyl)-5-(2-chloro-3,5-difluorophenyl)-3-methyl-7-(trifluoromethyl)pyrido[2,3-d]pyrimidin-4(3H)-one;

2,7-Diamino-6-(1-aminoethyl)-5-(2-chloro-5-fluorophenyl)-3-methylpyrido[2,3-d]pyrimidin-4(3H)-one;

2-(6-(Aminomethyl)-7-ethoxy-1,3-dimethyl-2,4-dioxo-1,2,3,4-tetrahydropyrido[2,3-d]pyrimidin-5-yl)-5-chlorobenzonitrile;

6-(Aminomethyl)-5-(3,5-difluoro-2-methoxyphenyl)-2-(dimethylamino)-3-methyl-7-(trifluoromethyl)pyrido[2,3-d]pyrimidin-4(3H)-one;

6-(Aminomethyl)-7-(bis (2,2-difluoroethyl)amino)-5-(2-bromo-5-fluorophenyl)-1,3-dimethylpyrido[2,3-d]pyrimidine-2,4(1H, 3H)-dione;

6-(Aminomethyl)-5-(2-bromo-5-fluorophenyl)-7-(2,2-difluoroethylamino)-1,3-dimethylpyrido[2,3-d]pyrimidine-2,4(1H,3H)-dione;

5-(2-Bromo-5-fluorophenyl)-7-chloro-1,3-dimethyl-2,4-dioxo-1,2,3,4-tetrahydropyrido[2,3-d]pyrimidine-6-carbonitrile;

5-(2-Bromo-5-fluoro-phenyl)-1,3-dimethyl-7-morpholin-4-yl-2,4-dioxo-1,2,3,4-tetrahydro-pyrido[2,3-d]pyrimidine-6-carbonitrile;

6-(Aminomethyl)-5-(2-bromo-5-fluorophenyl)-1,3-dimethyl-7-morpholinopyrido[2,3-d]pyrimidine-2,4(1H, 3H)-dione;

6-(Aminomethyl)-5-(2-bromo-5-fluorophenyl)-1,3-dimethyl-7-(4-methylpiperazin-1-yl)pyrido[2,3-d]pyrimidine-2,4(1H, 3H)-dione;

6-(Aminomethyl)-5-(2-bromo-5-fluorophenyl)-1,3-dimethyl-7-(pyridine-4-ylmethylamino)pyrido[2,3-d]pyrimidine-2,4(1H, 3H)-dione;

6-(Aminomethyl)-5-(2-bromo-5-fluorophenyl)-1,3-dimethyl-7-(cyclopropylamino)-1,3-dimethylpyrido[2,3-d]pyrimidine-2,4(1H, 3H)-dione;

6-(Aminomethyl)-5-(2,5-dichloro)-1,3-dimethyl-7-morpholinopyrido[2,3-d]pyrimidine-2,4(1H, 3H)-dione;

7-Amino-6-(aminomethyl)-5-(2,4-dichlorophenyl)-1-methylpyrido[2,3-d]pyrimidine-2,4(1H,3H)-dione;

6-(Aminomethyl)-5-(2-bromo-5-fluorophenyl)-7-(diethylamino)-1,3-dimethylpyrido[2,3-d]pyrimidine-2,4(1H, 3H)-dione;

6-(Aminomethyl)-5-(2-bromo-5-fluorophenyl)-7-(ethylamino)-1,3-dimethylpyrido[2,3-d]pyrimidine-2,4(1H, 3H)-dione;

6-(Aminomethyl)-5-(2-bromo-5-fluorophenyl)-1,3-dimethyl-7-(methylamino)pyrido[2,3-d]pyrimidine-2,4(1H, 3H)-dione;

6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(3-hydroxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;

7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;

6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;

6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;

6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;

7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;

6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;

6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;

3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;

6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;

6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;

6-(Aminomethyl)-1,3-dimethyl-7-(naphthalen-2-ylmethylamino)-5-(2-phenoxyphenyl)pyrido[2,3-d]pyrimidine-2,4(1H,3H)-dione;

6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(Aminomethyl)-5-(3-fluorophenyl)-1,3-dimethyl-7-(naphthalen-2-ylmethylamino)pyrido[2,3-d]pyrimidine-2,4(1H,3H)-dione;

6-(Aminomethyl)-5-(3-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(3-phenylpropylamino)pyrido[2,3-d]pyrimidine-2,4(1H,3H)-dione;

6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(2-bromo-5-fluorophenyl)-7-(1,2-diphenylethylamino)-1,3-dimethylpyrido[2,3-d]pyrimidine-2,4(1H,3H)-dione;

6-(Aminomethyl)-5-(5-fluoro-2-methoxyphenyl)-7-(3-methoxybenzylamino)-1,3-dimethylpyrido[2,3-d]pyrimidine-2,4(1H,3H)-dione;

6-(Aminomethyl)-5-(5-fluoro-2-methoxyphenyl)-7-(3-isobutoxybenzylamino)-1,3-dimethylpyrido[2,3-d]pyrimidine-2,4(1H,3H)-dione;
5-(3,5-Dimethoxyphenyl)-6-((methylamino)methyl)-1,3-dimethyl-7-(naphthalen-2-ylmethylamino)pyrido[2,3-d]pyrimidine-2,4(1H,3H)-dione;
6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione;
6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(phenethylamino)pyrido[2,3-d]pyrimidine-2,4(1H,3H)-dione;
6-(Aminomethyl)-5-(2-bromo-5-fluorophenyl)-7-(4-(ethylamino)phenylthio)-1,3-dimethylpyrido[2,3-d]pyrimidine-2,4(1H,3H)-dione;
N-(4-(6-(Aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide;
6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione;
5-(3,5-Dimethoxyphenyl)-6-((ethylamino)methyl)-1,3-dimethyl-7-(naphthalen-2-ylmethylamino)pyrido[2,3-d]pyrimidine-2,4(1H,3H)-dione;
6-(Aminomethyl)-5-(2,4-dichlorophenyl)-7-(2,5-dipropoxybenzylamino)-1-methylpyrido[2,3-d]pyrimidine-2,4(1H,3H)-dione;
7-Amino-6-(aminomethyl)-5-(3-isobutoxyphenyl)-1,3-dimethylpyrido[2,3-d]pyrimidine-2,4(1H,3H)-dione;
7-Amino-6-(aminomethyl)-1,3-dimethylpyrido[2,3-d]pyrimidine-2,4(1H,3H)-dione;
7-Amino-6-(Aminomethyl)-5-(4-(aminomethyl)phenyl)-1,3-dimethylpyrido[2,3-d]pyrimidine-2,4(1H,3H)-dione;
6-(Aminomethyl)-5-(benzo[d]thiazol-2-yl)-1,3-dimethyl-7-(naphthalen-2-ylmethylamino)pyrido[2,3-d]pyrimidine-2,4(1H,3H)-dione;
6-(Aminomethyl)-7-(1,2-diphenylethylamino)-5-(5-fluoro-2-methoxyphenyl)-1,3-dimethylpyrido[2,3-d]pyrimidine-2,4(1H,3H)-dione;
6-(Aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione; and
6-(Aminomethyl)-7-(bis(naphthalen-2-ylmethyl)amino)-5-(3-hydroxyphenyl)-1,3-dimethylpyrido[2,3-d]pyrimidine-2,4(1H,3H)-dione.

Particular examples of compounds or the second compounds according to the present invention include, but are not limited to:
6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;
6-(Aminomethyl)-5-(3-hydroxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;
7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;
6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;
6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;
6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;
7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;
6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;
6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;
3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;
6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;
6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;
6-(Aminomethyl)-1,3-dimethyl-7-(naphthalen-2-ylmethylamino)-5-(2-phenoxyphenyl)pyrido[2,3-d]pyrimidine-2,4(1H,3H)-dione;
6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;
6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;
6-(Aminomethyl)-5-(3-fluorophenyl)-1,3-dimethyl-7-(naphthalen-2-ylmethylamino)pyrido[2,3-d]pyrimidine-2,4(1H,3H)-dione;
6-(Aminomethyl)-5-(3-isobutoxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(3-phenylpropylamino)pyrido[2,3-d]pyrimidine-2,4(1H,3H)-dione;
6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione;
6-(Aminomethyl)-5-(2-bromo-5-fluorophenyl)-7-(1,2-diphenylethylamino)-1,3-dimethylpyrido[2,3-d]pyrimidine-2,4(1H,3H)-dione;
6-(Aminomethyl)-5-(5-fluoro-2-methoxyphenyl)-7-(3-methoxybenzylamino)-1,3-dimethylpyrido[2,3-d]pyrimidine-2,4(1H,3H)-dione;
6-(Aminomethyl)-5-(5-fluoro-2-methoxyphenyl)-7-(3-isobutoxybenzylamino)-1,3-dimethylpyrido[2,3-d]pyrimidine-2,4(1H,3H)-dione;
5-(3,5-Dimethoxyphenyl)-6-((methylamino)methyl)-1,3-dimethyl-7-(naphthalen-2-ylmethylamino)pyrido[2,3-d]pyrimidine-2,4(1H,3H)-dione;
6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione;
6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(phenethylamino)pyrido[2,3-d]pyrimidine-2,4(1H,3H)-dione;

6-(Aminomethyl)-5-(2-bromo-5-fluorophenyl)-7-(4-(ethylamino)phenylthio)-1,3-dimethylpyrido[2,3-d]pyrimidine-2,4(1H,3H)-dione;

N-(4-(6-(Aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide;

6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione;

5-(3,5-Dimethoxyphenyl)-6-((ethylamino)methyl)-1,3-dimethyl-7-(naphthalen-2-ylmethylamino)pyrido[2,3-d]pyrimidine-2,4(1H,3H)-dione;

6-(Aminomethyl)-5-(2,4-dichlorophenyl)-7-(2,5-dipropoxybenzylamino)-1-methylpyrido[2,3-d]pyrimidine-2,4(1H,3H)-dione;

6-(Aminomethyl)-5-(benzo[d]thiazol-2-yl)-1,3-dimethyl-7-(naphthalen-2-ylmethylamino)pyrido[2,3-d]pyrimidine-2,4(1H,3H)-dione;

6-(Aminomethyl)-7-(1,2-diphenylethylamino)-5-(5-fluoro-2-methoxyphenyl)-1,3-dimethylpyrido[2,3-d]pyrimidine-2,4(1H,3H)-dione;

6-(Aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione; and 6-(Aminomethyl)-7-(bis(naphthalen-2-ylmethyl)amino)-5-(3-hydroxyphenyl)-1,3-dimethylpyrido[2,3-d]pyrimidine-2,4(1H,3H)-dione.

More particular examples of compounds or the second compounds according to the present invention include, but are not limited to:

6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(3-hydroxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;

7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;

6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;

6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;

6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;

7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;

6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;

6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;

3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;

6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;

6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;

6-(Aminomethyl)-1,3-dimethyl-7-(naphthalen-2-ylmethylamino)-5-(2-phenoxyphenyl)pyrido[2,3-d]pyrimidine-2,4(1H,3H)-dione;

6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(Aminomethyl)-5-(3-fluorophenyl)-1,3-dimethyl-7-(naphthalen-2-ylmethylamino)pyrido[2,3-d]pyrimidine-2,4(1H,3H)-dione;

6-(Aminomethyl)-5-(3-isobutoxyphenyl)-1,3-dimethyl-7-(naphthalen-2-ylmethylamino)pyrido[2,3-d]pyrimidine-2,4(1H,3H)-dione;

6-(Aminomethyl)-7-(1,2-diphenylethylamino)-5-(5-fluoro-2-methoxyphenyl)-1,3-dimethylpyrido[2,3-d]pyrimidine-2,4(1H,3H)-dione;

6-(Aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione; and 6-(Aminomethyl)-7-(bis(naphthalen-2-ylmethyl)amino)-5-(3-hydroxyphenyl)-1,3-dimethylpyrido[2,3-d]pyrimidine-2,4(1H,3H)-dione.

Salts, Hydrates, and Prodrugs of Renin Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

The present invention also encompasses quaternally ammonium salts for the compounds of the present invention comprising basic nitrogen containing groups. The quaternally ammonium salts include, but are not limited to, those that be quaternized with such agents as $(C_{1-4})$alkyl halides, e.g., methyl, ethyl, iso-propyl and tert-butyl chlorides, bromides and iodides; di $(C_{1-4})$alkyl sulfates, e.g., dimethyl, diethyl and diamyl sulfates; $(C_{10-18})$alkyl halides, e.g., decyl, dodecyl, lauryl, myristyl and stearyl chlorides, bromides and iodides; and aryl$(C_{1-4})$alkyl halides, e.g., benzyl chloride and phenethyl bromide. Such salts permit the preparation of both water-soluble and oil-soluble compounds of the present invention.

The present invention also encompasses N-oxides of compounds according to the present invention. The N-oxides can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds of the invention further include prodrug derivatives of the compounds. It is noted that in many instances, the prodrugs themselves also fall within the scope of the range of compounds according to the present invention. Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, sulfonate esters, and other Prodrug forms that are well known in the art. For examples of such prodrug derivatives, see, e.g., a) DESIGN OF PRODRUGS, Bundgaard, A. Ed., 1985, Elsevier;
b) Bundgaard, H. *Design and Application of Prodrugs* in A TEXTBOOK OF DRUG DESIGN AND DEVELOPMENT, Krosgaard-Larsen and H. Bundgaard, Ed., 1991, Chapter 5, p. 113-191;
c) Bundgaard, H., *Advanced Drug Delivery Review,* 1992, 8, 1-38; and
d) Saulnier et al. *Bioorganic and Medicinal Chemistry Letters,* 1994, Vol. 4, p. 1985; and
e) METHOD IN ENZYMOLOGY, Widder, K. et al., Ed.; 1985, Academic, vol. 42, p. 309-396, each of which is incorporated herein by reference.

The invention further includes solvates and hydrates of the compounds of the invention. The solvates and hydrates may be formed during the process of the preparation or may be conveniently prepared by recrystallization from an aqueous/organic solvent mixture, using organic solvents such as dioxin, tetrahydrofuran or methanol.

Uses of the Renin Inhibitors

Renin inhibitors of the present invention may be used to treat and/or prevent high blood pressure, cardiovascular diseases, congestive heart failure, myocardial infarction, renal protection, inflammation, neurological disease and cancer.

Renin is a proteolytic enzyme synthesized and stored principally in the juxtaglomerular apparatus. When renin is released into the blood from the kidney, the renin-angiotensin-aldosterone system ("RAAS") is activated. Renin acts on the alpha-2 globulin angiotensinogen (synthesized in the liver) to generate angiotensin I. This non-pressor decapeptide is converted to angiotensin II by angiotensin-converting enzyme (ACE). The major pharmacological effects of angiotensin II are vasoconstriction and stimulation of the adrenal cortex to release aldosterone, a hormone which causes sodium retention. Vasoconstriction and conservation of sodium both contribute to increased blood pressure. Angiotensin II also produces other physiological effects such as inhibiting renin secretion, increasing sympathetic nervous system activity, stimulating vasopressin secretion, causing a positive cardiac inotropic effect and modulating other hormonal systems. Thus, the renin-angiotensin system plays an important role in normal cardiovascular homeostasis and in some forms of elevated blood pressure (hypertension).

The reduction of the activity of renin in a subject through inhibition may therefore be used to therapeutically address the diseases and conditions caused by the overactivation of RAAS.

Thus, renin inhibiting compounds of the present invention may be used as agents for control of hypertension, may also be used to treat and/or prevent congestive heart failure and hyperaldosteronism, vascular diseases related to diabetes, and renal diseases such as acute or chronic renal failure. In addition, the renin inhibiting compounds may also be used as diagnostic agents for identification of cases of hypertension due to renin excess.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members.

In addition, the compounds of the present invention may be useful as inhibitors of plasmepsins to treat malaria and as inhibitors of *Candida albicans* secreted aspartyl proteases to treat fungal infections.

It is further noted that additional diseases beyond those disclosed herein may also be identified as the biological roles that renin and the RAAS system play in various pathways become more fully understood.

It is further noted that the compounds of the present invention may be useful as inhibitors of dipeptidyl peptidase IV (DPP-IV) to treat diseases and conditions associate with type II diabetes.

Combination Therapy

A wide variety of therapeutic agents may have a therapeutic additive or synergistic effect when used in combination with renin inhibitors according to the present invention. Such therapeutic agents may additively or synergistically combine with the renin inhibitors to reduce or alleviate the effects and symptoms of cardiovascular disease.

The compounds according to the present invention may be used in combination with other therapeutic agents, wherein the cells are treated with a compound according to the present invention before, at the same time, and/or after the cells are treated with the one or more additional cardiovascular therapeutics; these treatments are referred to herein as combination therapy. It is noted that administration of one agent before another is referred to herein as sequential therapy, even if the agents are also administered together. It is noted that combination therapy is intended to cover methods where agents are administered before or after each other (sequential therapy) as well as when the agents are administered at the same time.

Representative classes of cardiovascular agents that may be used with the renin inhibitors of the present invention include, but are not limited to, diuretics, adrenergic blocking agents, vasodilators, calcium channel blockers, angiotensin converting enzyme (ACE) inhibitors, potassium channel activators, antiserotoninergic agents, thromboxane synthetase inhibitors, angiotensin II antagonists, angiotensin II receptor blockers, and other agents useful for treating (in a human or other mammal) hypertension, congestive heart failure, or vascular diseases related to diabetes, or for treating renal diseases such as acute or chronic renal failure.

Representative diuretics include hydrochlorothiazide, polythiazide, piretanide, torasemide, bumetanide, amiloride, chlorothiazide, indapamide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof Representative adrenergic blocking agents include phentolamine, phenoxybenzamine, prazosin, terazosin, tolazine, atenolol, metoprolol, albuterol, nadolol, propranolol, timolol, carteolol and the like or a pharmaceutically acceptable salt thereof.

Representative vasodilators include hydralazine, minoxidil, diazoxide, nitroprusside, flos equinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include ramipril, aptopril, enalapril, lisinopril, fosinopril, captopril and the like or a pharmaceutically acceptable salt thereof Representative potassium channel activators include pinacidil, glibenclamide, glimepiride, diaoxide, cromocalim, and the like or a pharmaceutically acceptable salt thereof.

Representative antiserotoninergic agents include ketanserin and the like or a pharmaceutically acceptable salt thereof.

Representative angiotensin II antagonists include DUP527 and the like or a pharmaceutically acceptable salt thereof.

Representative angiotensin II receptor blockers (angiotensin II receptor antagonists (ARBs)) include losartan, irbesartan, valsartan, omapatrilat, gemopatrilat and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

Dosage, Host and Safety

The compounds of the present invention are stable and can be used safely. In particular, the compounds of the present invention are useful as renin inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Compositions Comprising Renin Inhibitors

A wide variety of compositions and administration methods may be used in conjunction with the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The renin inhibitors and compositions comprising them may be administered or coadministered in any conventional dosage form. Co-administration in the context of this invention is intended to mean the administration of more than one therapeutic agent, one of which includes a renin inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds for use with the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds for use with the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce renin activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more renin inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds for use with the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds for use with the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the renin inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The renin inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a renin inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Formation for Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The renin inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the renin inhibitor alone or in combination with other pharmaceutically acceptable excipients can also be administered.

E. Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---:|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
| --- | --- |
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
| --- | --- |
| Compound of the Present Invention | 1% |
| Microcrystalline Cellulose | 73% |
| Stearic Acid | 25% |
| Colloidal Silica | 1%. |

Kits and Articles of Manufacture Comprising Renin Inhibitors

The invention is also directed to kits and other articles of manufacture for treating diseases associated with renin. It is noted that diseases are intended to cover all conditions for which the renin possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Preparation and Assaying of Compounds of the Invention

Various methods may be developed for synthesizing compounds for use with the present invention. Representative methods for preparing the compounds of the invention are provided in the reaction schemes shown below. Specific procedures for synthesizing these compounds are provided in the Example section. It should also be appreciated, that the compounds of the present invention may also be synthesized by other synthetic routes that others may devise.

Synthetic Schemes for Compounds of the Present Invention

A general synthetic route for producing compounds of the present invention is shown in Scheme 1. Condensation of Compound A with an aldehyde provides Compound B, which is then treated with Compound C to give Compound D. Finally, reduction gives the compound of the present invention.

Scheme 1:

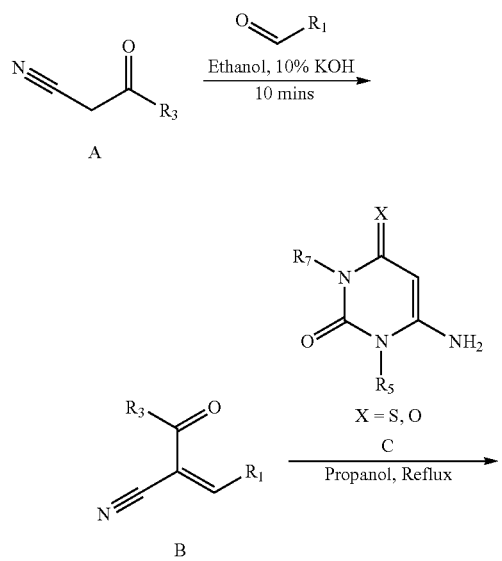

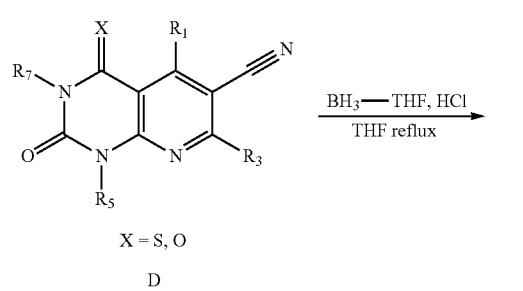

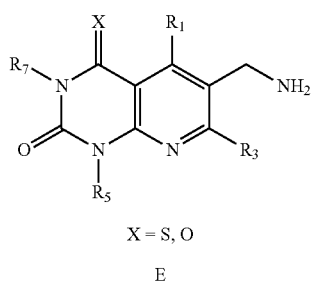

A synthetic route for producing other compounds of the present invention is shown in Scheme 2. Condensation of Compound F with an aldehyde provides Compound G, which is then treated with Compound H to give Compound I. Reductive amination gives the compound of the present invention.

Scheme 2:

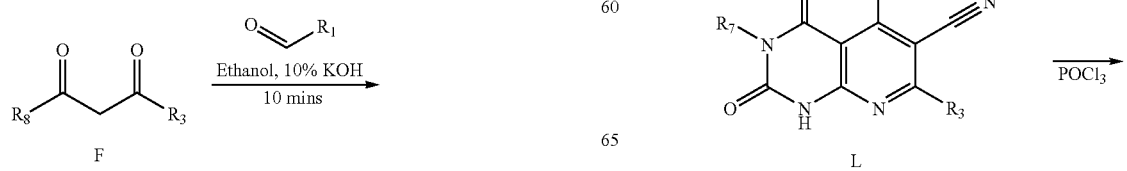

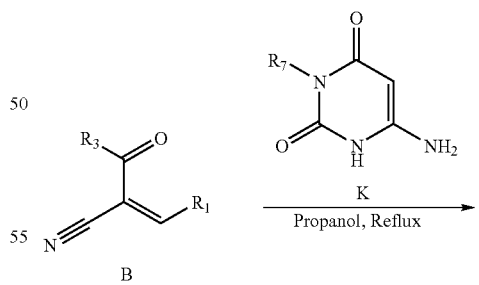

A synthetic route for producing other compounds of the present invention is shown in Scheme 3. Treatment of Compound B with Compound K provides Compound L, which is then halogenated to give Compound M. Amination followed by reduction gives the compound of the present invention.

Scheme 3:

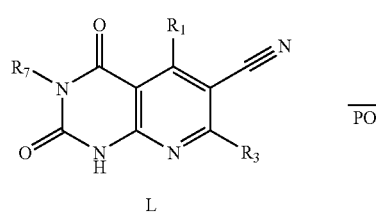

65

-continued

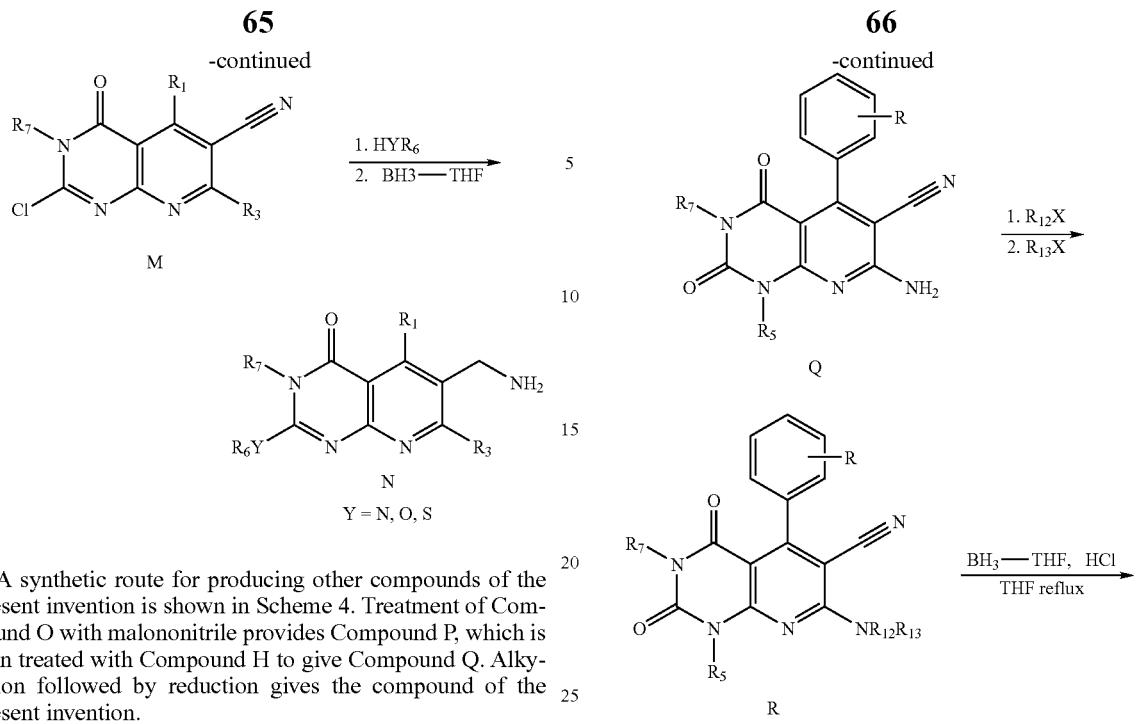

A synthetic route for producing other compounds of the present invention is shown in Scheme 4. Treatment of Compound O with malononitrile provides Compound P, which is then treated with Compound H to give Compound Q. Alkylation followed by reduction gives the compound of the present invention.

Scheme 4:

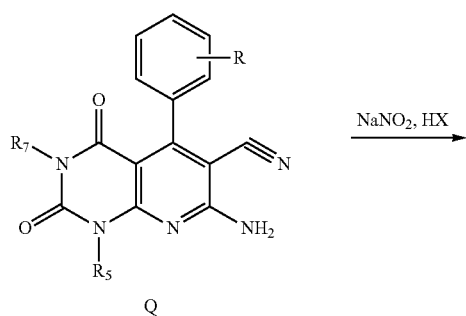

66

-continued

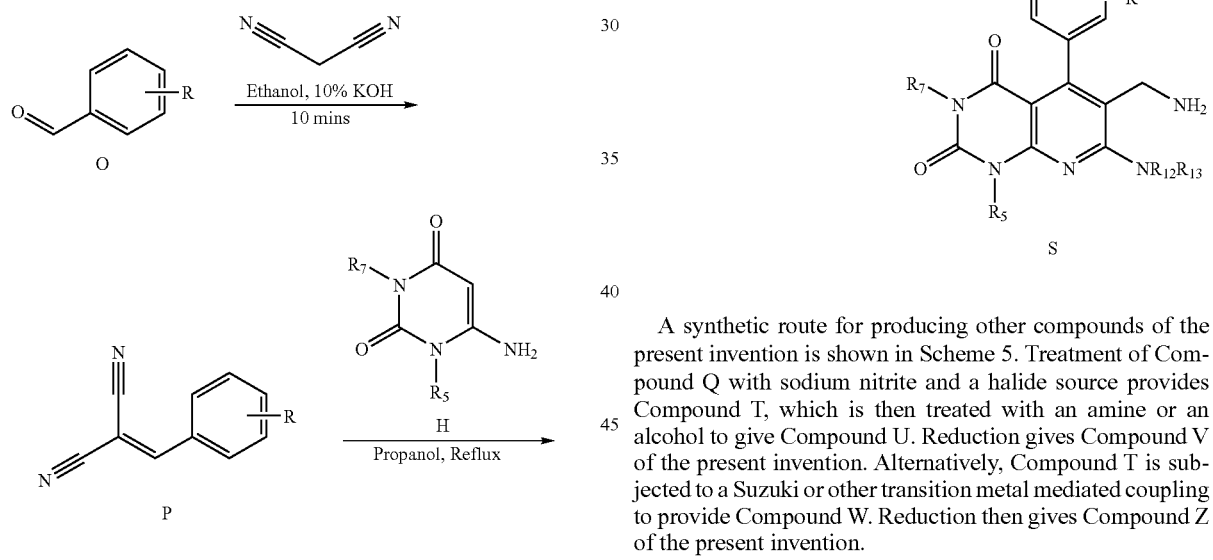

A synthetic route for producing other compounds of the present invention is shown in Scheme 5. Treatment of Compound Q with sodium nitrite and a halide source provides Compound T, which is then treated with an amine or an alcohol to give Compound U. Reduction gives Compound V of the present invention. Alternatively, Compound T is subjected to a Suzuki or other transition metal mediated coupling to provide Compound W. Reduction then gives Compound Z of the present invention.

Scheme 5:

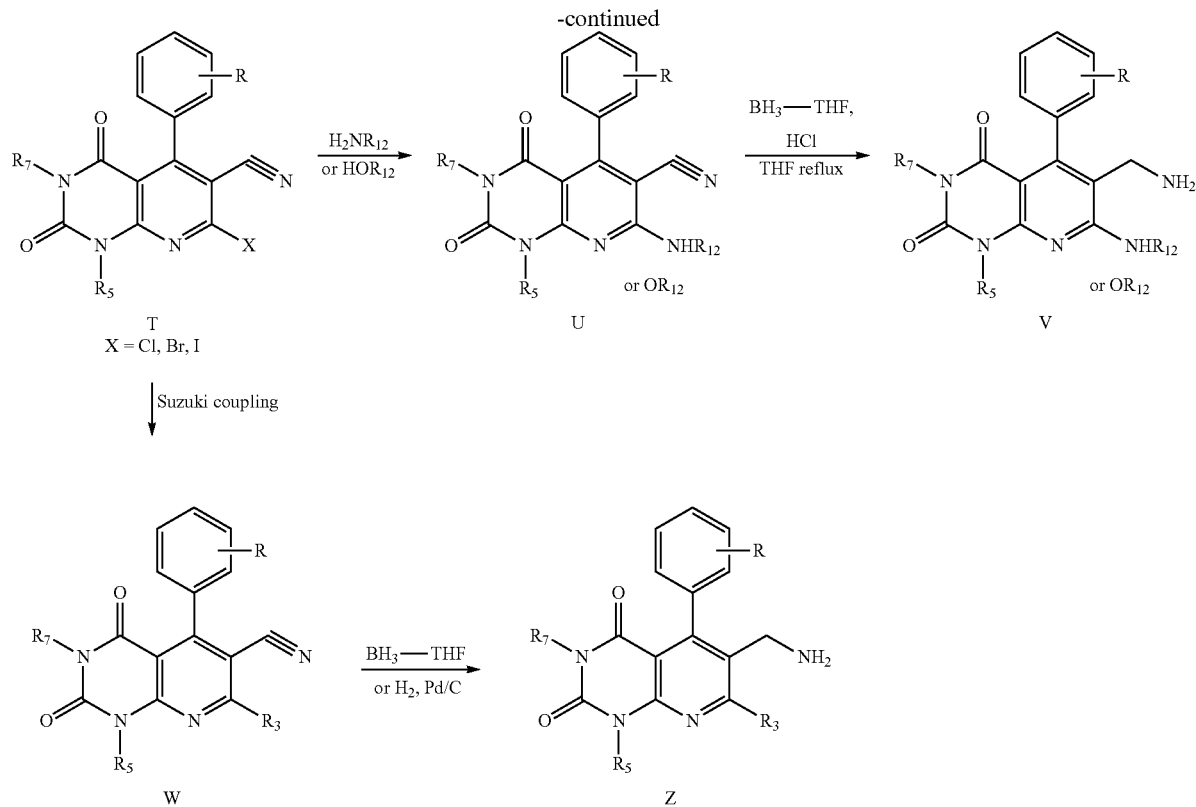

Another synthetic route for producing other compounds of the present invention is shown in Scheme 6. Treatment of Compound AA with malononitrile provides Compound AB, which is then treated with Compound AC to give Compound AD which is reduced to give Compound AE.

Scheme 6:

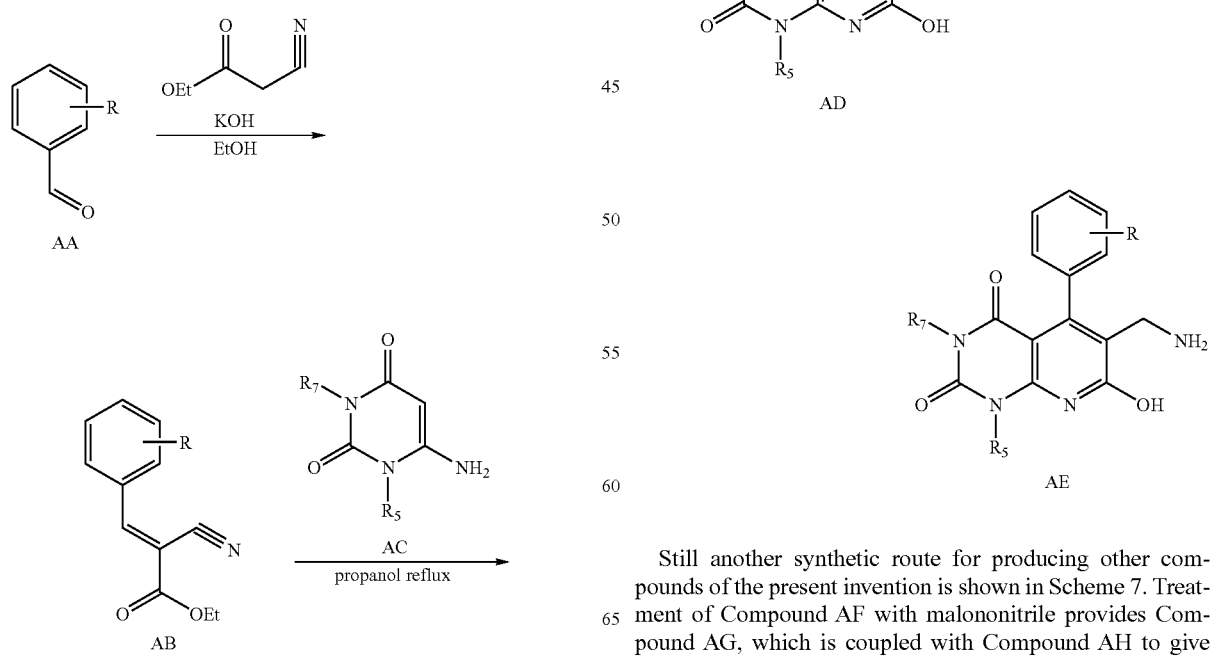

Still another synthetic route for producing other compounds of the present invention is shown in Scheme 7. Treatment of Compound AF with malononitrile provides Compound AG, which is coupled with Compound AH to give Compound AI. Reduction of AI gives AJ.

Scheme 7:

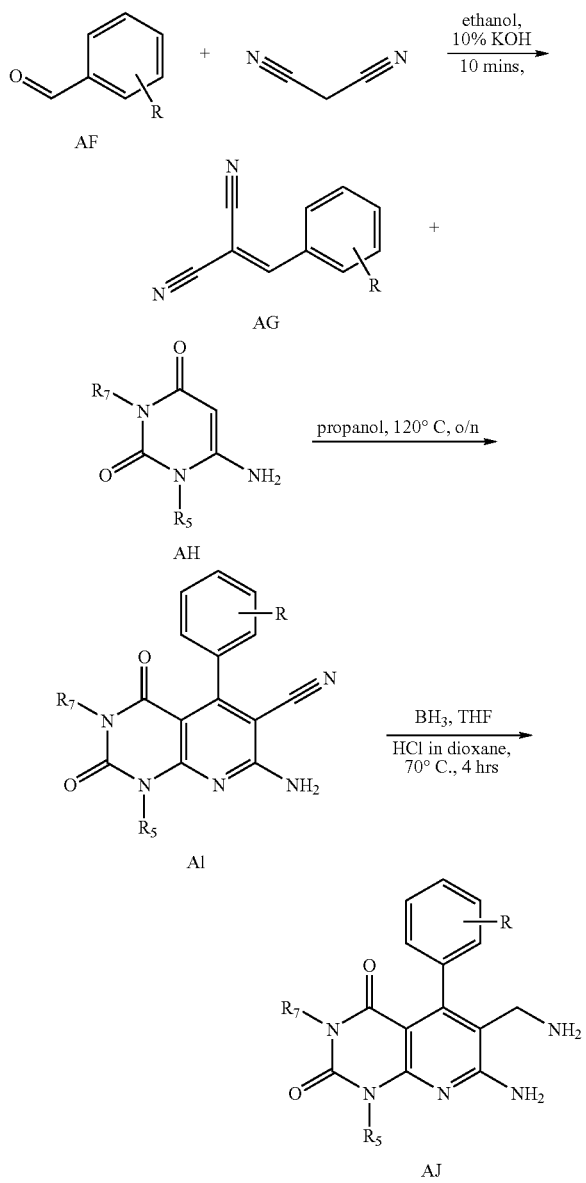

It should be noted that in each of the reaction schemes, the various substituents may be selected from among the various substituents otherwise taught herein. It should be appreciated that by varying the V, W, X, Y, Z, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ groups, a wide variety of different renin inhibitors according to the present invention may be synthesized.

General Procedures

It will be readily recognized that certain compounds for use with the present invention have atoms with linkages to other atoms that confer a particular stereochemistry to the compound (e.g., chiral centers). It is recognized that synthesis of compounds for use with the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds for use with the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds for use with the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in P. G. M. Wuts and T. W. Greene, *"Greene's Protecting Groups in Organic Synthesis"*, 4th edition, John Wiley & Sons, Inc. 2007.

Compounds for use with the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl)
atm (atmosphere)
ATP (Adenosine Triphophatase)
Boc (tert-butyloxycarbonyl)
BOP (bis(2-oxo-3-oxazolidinyl)phosphinic chloride)
Brij35 (polyoxyethyleneglycol dodecyl ether)
BSA (Bovine Serum Albumin)
CBZ (benzyloxycarbonyl)
CDI (1,1-carbonyldiimidazole)
DCC (dicyclohexylcarbodiimide)
DCE (dichloroethane)
DCM (dichloromethane)
DIEA (di-isopropylethylamine)
DMAP (4-dimethylaminopyridine)
DME (1,2-dimethoxyethane)
DMF (N,N-dimethylformamide)
DMPU (N,N'-dimethylpropyleneurea)
DMSO (dimethylsulfoxide)
DTT (dithiothreitol)
EDCI (ethylcarbodiimide hydrochloride)
EDTA (Ethylenediaminetetraacetic acid)
Et (ethyl)
Et$_2$O (diethyl ether)
EtOAc (ethyl acetate)
FMOC (9-fluorenylmethoxycarbonyl)
g (grams)
h (hours)
HOAc or AcOH (acetic acid)
HOBT (1-hydroxybenzotriazole)
HOSu (N-hydroxysuccinimide)
HPLC (high pressure liquid chromatography)
Hz (Hertz)
IBCF (isobutyl chloroformate)
i.v. (intravenous)
i-PrOH (isopropanol)
L (liters)
LAH (lithium aluminium hydride)
M (molar)
mCPBA (meta-chloroperbenzoic acid)
Me (methyl)
MeOH (methanol)
mg (milligrams)
MHz (megahertz)
μL (microliters)
mL (milliliters)
mM (millimolar)
min (minutes)
mmol (millimoles)
mol (moles)
MOMCl (methoxymethyl chloride)

-continued

MOPS (morpholinepropanesulfonic acid)
mp (melting point)
NaOAc (sodium acetate)
NEt$_3$ (triethylamine)
OMe (methoxy)
OTf (O-triflate)
OMs (O-mesylate)
Pd(dppf)Cl$_2$ (bis(diphenyl phosphino)ferrocene dichloro palladium (II)
psi (pounds per square inch)
RP (reverse phase)
RT (ambient temperature)
SPA (Scintillation Proximity Assay)
TBAF (tetra-n-butylammonium fluoride)
TBDMS (tert-butyldimethylsilyl)
TBS (t-butyldimethylsilyl)
tBu (tert-butyl)
TEA (triethylamine)
TFA (trifluoroacetic acid)
TFAA (trifluoroacetic anhydride)
THF (tetrahydrofuran)
TIPS (triisopropylsilyl)
TLC (thin layer chromatography)
TMS (trimethylsilyl)
TMSE (2-(trimethylsilyl)ethyl)
TMSI (trimethylsilyliodide)
Tr (retention time)

All references to ether or Et2O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

1H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-23, John Wiley and Sons, New York, N.Y., 2006; Rodd's Chemistry of Carbon Compounds, vols. 1-5 and supps., Elsevier Science Publishers, 1998; Organic Reactions, vols. 1-68, John Wiley and Sons, New York, N.Y., 2007; March J.: Advanced Organic Chemistry, 5th ed., 2001, John Wiley and Sons, New York, N.Y.; and Larock: Comprehensive Organic Transformations, 2nd edition, John Wiley and Sons, New York, 1999. The entire disclosures of all documents cited throughout this application are incorporated herein by reference.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques, Andre Collet, and Samuel H. Wilen, Enantiomers, Racemates and Resolutions, John Wiley & Sons, Inc. (1981).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, and Samuel H. Wilen, Enantiomers, Racemates and Resolutions, John Wiley & Sons, Inc. (1981).

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5□4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 □L in methanol at 0.1 mg/mL in concentration.

In another variation, preparative chiral separations are performed using a Berger MultiGram II SFC purification system. For example, samples can be loaded onto a ChiralPak AD column (21×250 mm, 10□). In particular variations, the flow rate for separation can be 70 mL/min, the injection volume up to 2 mL, and the inlet pressure set at 130 bar. Stacked injections can be applied to increase the efficiency.

Descriptions of the syntheses of particular compounds according to the present invention based on the above reaction schemes and variations thereof are set forth in the Example section.

Biological Testing

The activity of compounds as renin inhibitors may be assayed in vitro, in vivo or in a cell line. Example D below provides an in vitro enzymatic activity assay for activity against renin.

Test compounds in varying concentrations may be reacted with recombinant human renin in the presence of substrate, e.g., QXL520-γ-Abu-Ile-His-Pro-Phe-His-Leu-Val-Ile-His-Thr-Lys (HiLyteFluo488)-Arg-OH (Anaspec, San Jose, Calif.). The reaction can be followed kinetically using fluorescence (excitation λ=485 nm; emission λ=538 nm). Inhibition constants ($IC_{50}$) may be calculated by non-linear curve fitting of the compound concentrations and fluorescence intensities to the standard $IC_{50}$ equation.

Similarly, the protease inhibitory activities of the compounds of the invention can be readily determined by methods known to those of ordinary skill in the art since suitable in vitro assays for measuring protease activity and the inhibition thereof by test compounds are known. Examples of assays that may be used for measuring protease inhibitory activity and selectivity are set forth in Examples E-H.

$IC_{50}$ values for selected compounds of the present invention are given in Table 1.

EXAMPLE

The present invention is further exemplified, but not limited by, the following examples that describe the synthesis of particular compounds according to the invention. It is noted, that a variety of different solvents, temperatures and other reaction conditions can be varied to optimize the yields of the reactions.

Example 1

Preparation of 7-Amino-6-aminomethyl-5-(2,4-dichloro-phenyl)-1,3-dimethyl-1H-pyrido[2,3-d]pyrimidine-2,4-dione (Compound 1)

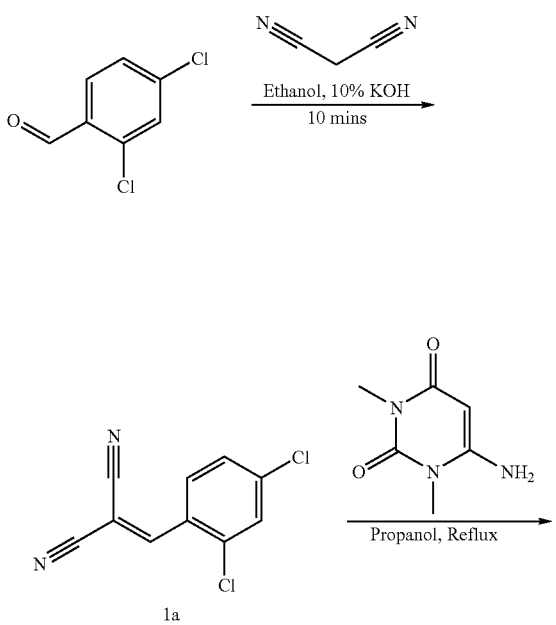

-continued

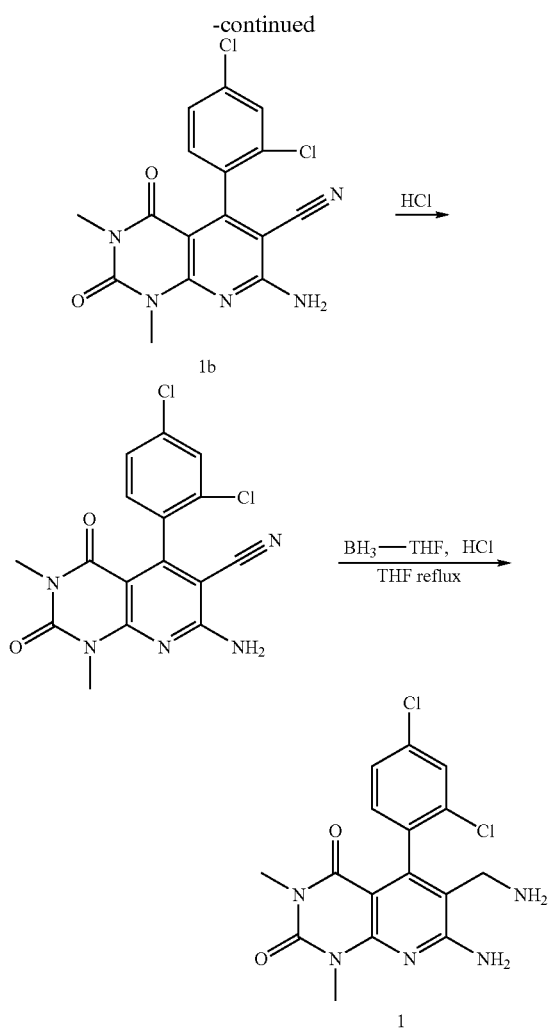

To a solution of 2,4-dichlorobenzaldehyde (1.75 g, 10 mmol) and malononitrile (660 mg, 10 mmol) in ethanol (10 ml) was added 200 μL of 10% aqueous KOH. The mixture was stirred at room temperature for 15 min, allowed to stand for 30 min, cooled with ice-bath and then filtered to give 2-(2,4-dichloro-benzylidene)-malononitrile (1a) as a white solid (1.8 g).

A mixture of 1a (150 mg, 0.6 mmol) and 6-amino-1,3-dimethyl uracil (200 mg, 1.2 mmol) in propanol (5 ml) was refluxed overnight, concentrated, redissolved in DCM, washed with 5% aqueous HCl, water, dried over Na$_2$SO$_4$, and concentrated to give the crude product 7-amino-5-(2,4-dichlorophenyl)-1,3-dimethyl-2,4-dioxo-1,2,3,4-tetrahydro-pyrido[2,3-d]pyrimidine-6-carbonitrile (1b).

To the crude product 1b in a mixture of pyridine and DCM (5:1, 5 mL) was added HCl (0.5 mL). The mixture was heated at 100° C. in a microwave for 10 min, concentrated, redissolved in DCM, washed with 5% aqueous HCl and water.

To the residue in THF (3 mL), a solution of 1M BH$_3$-THF (2.4 mL, 2.4 mmol) and two drops of 4 M HCl in dioxane were added. The mixture was heated under reflux for 4 h, concentrated, co-evaporated with MeOH, redissolved in MeOH and acidified with TFA. The residue was purified by LC-MS to give the title compound as the TFA salt. $^1$H NMR (400 MHz, CDCl$_3$-CD$_3$OD) δ 7.47 (d, J=2.0 Hz, 1H) 7.32 (dd, J=8.1, 2.0 Hz, 1H) 7.03 (d, J=8.1 Hz, 1H) 3.74 and 3.58 (ABq, J=14.9 and 59.4 Hz, 2H) 3.56 (s, 3H) 3.19 (s, 3H). [M-NH$_2$] calc'd for C$_{16}$H$_{13}$Cl$_2$N$_4$O$_2$, 363; found, 363.

Example 2

Preparation of 7-Amino-6-aminomethyl-5-(2-bromo-4-fluoro-phenyl)-1,3-dimethyl-1H-pyrido[2,3-d]pyrimidine-2,4-dione (Compound 2)

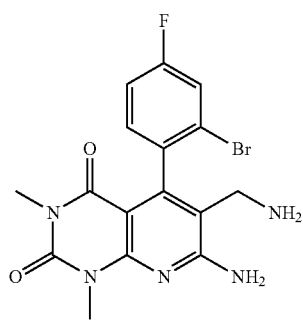

The title compound was synthesized from 2-bromo-4-fluoro-benzaldehyde following the same procedure described in the synthesis of Example 1. $^1$H NMR (400 MHz, CDCl$_3$—CD$_3$OD 10:1) 7.40 (dd, J=8.2, 2.4 Hz, 1H) 7.12 (td, J=8.2, 2.5 Hz, 1H) 7.04-7.09 (dd, J=5.9, 8.6 Hz, 1H), 3.71 (d, J=14.7 Hz 1H) 3.55-3.62 (m, 4H), 3.20 (s, 3H). [M-NH$_2$] calc'd for C$_{16}$H$_{13}$BrFN$_4$O$_2$, 391; found, 391.

Example 3

Preparation of 7-Amino-6-aminomethyl-5-(2-bromo-phenyl)-1,3-dimethyl-1H-pyrido[2,3-d]pyrimidine-2,4-dione (Compound 3)

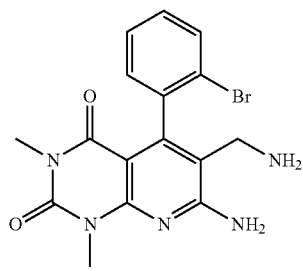

The title compound was synthesized from 2-bromo-benzaldehyde following the same procedure described in the synthesis of Example 1. $^1$H NMR (400 MHz, DMSO-D6) δ 7.68 (dd, J=7.96, 1.1 Hz, 1H) 7.43-7.47 (dd, J=7.5, 1.5 Hz, 1H) 7.34 (td, J=7.7, 1.5 Hz, 1H) 7.27 (dd, J=7.6, 1.5 Hz, 1H)

3.81 (d, J=13.9 Hz, 1H) 3.53 (m, 4H), 3.07 (s, 3H). [M-NH$_2$] calc'd for C$_{16}$H$_{14}$BrN$_4$O$_2$, 373; found, 373.

Example 4

Preparation of 6-Aminomethyl-5-(2,4-dichloro-phenyl)-7-ethylamino-1,3-dimethyl-1H-pyrido[2,3-d]pyrimidine-2,4-dione (Compound 4)

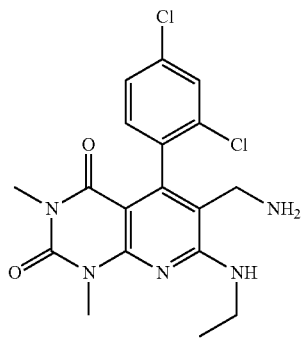

To a solution of 1B (Example 1, 300 mg, 0.8 mmol) in a mixture of pyridine and DCM (5:1, 5 mL) was added AcCl (0.5 mL). The mixture was heated at 100° C. in a microwave for 10 min, concentrated, redissolved in DCM, washed with 5% aqueous HCl and water. The crude product was dissolved in THF (2 mL), treated with BH$_3$-THF (4 mL) and two drops of 4 M HCl in dioxane under reflux overnight. General workup as described in the synthesis of Example 1 and LC-MS purification gave Compound 4 as the TFA salt. $^1$H NMR (400 MHz, CDCl$_3$—CD$_3$OD 10:1) δ 7.46 (d, J=1.8 Hz, 1H) 7.31 (dd, J=8.2, 1.9 Hz, 1H) 7.05 (d, J=8.3 Hz, 1H) 3.74 (d, J=14.7 Hz, 1H) 3.61 (s, 3H) 3.51-3.59 (m, 3H) 3.19 (s, 3H) 1.24 (t, J=7.074 Hz, 3H). [M-NH$_2$] calc'd for C$_{18}$H$_{17}$Cl$_2$N$_4$O$_2$, 391; found, 391.

Example 5

Preparation of 6-Aminomethyl-5-(2,4-dichloro-phenyl)-1,3-dimethyl-7-methylamino-1H-pyrido[2,3-d]pyrimidine-2,4-dione (Compound 5) and 6-Aminomethyl-5-(2,4-dichloro-phenyl)-7-dimethylamino-1,3-dimethyl-1H-pyrido[2,3-d]pyrimidine-2,4-dione (Compound 6)

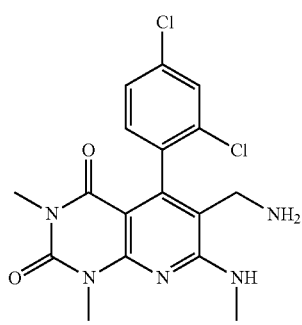

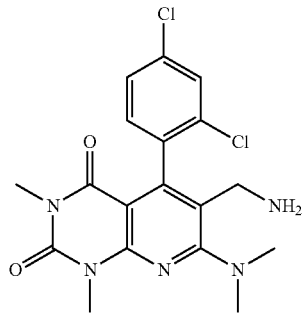

Compound 1B (Example 1, 200 mg, 0.5 mmol) in dry DMF (3 mL) was treated with 60% NaH (22 mg, 0.55 mmol), followed by MeI (105 mg, 0.75 mmol). The mixture was stirred at room temperature for 2 h, and then concentrated to dryness. The crude product was dissolved in DCM and washed with water. The crude mixture was dissolved in THF (2 mL) and then treated with BH$_3$-THF (2 mL) under reflux overnight. General workup as described in the synthesis of Example 1 and LC-MS purification gave Compound 5 and Compound 6.

Compound 5: $^1$H NMR (400 MHz, CDCl$_3$—CD$_3$OD 10:1) δ 7.47 (d, J=2.0 Hz, 1H) 7.32 (dd, J=8.3, 2.0 Hz, 1H) 7.03 (d, J=8.3 Hz, 1H) 3.72, 3.57 (ABq, J=14.9, 57.6 Hz, 2H), 3.63 (s, 3H), 3.20 (s, 3H), 3.03 (s, 3H). [M-NH$_2$] calc'd for C$_{17}$H$_{15}$Cl$_2$N$_4$O$_2$, 377; found, 377.

Compound 6: $^1$H NMR (400 MHz, CDCl$_3$—CD$_3$OD 10:1) δ 7.47 (d, J=2.0 Hz, 1H) 7.31 (dd, J=8.1, 2.0 Hz, 1H) 7.07 (d, J=8.3 Hz, 1H) 3.91, 3.72 (ABq, J=14.9, 78.1 Hz, 2H), 3.63 (s, 3H) 3.22 (s, 3H) 3.02 (s, 6H). [M-NH$_2$] calc'd for C$_{18}$H$_{18}$Cl$_2$N$_4$O$_2$, 392; found, 392.

Example 6

Preparation of 6-aminomethyl-5-(2-bromo-5-fluorophenyl)-7-hydroxy-1,3-dimethyl-1H-pyrido[2,3-d]pyrimidine-2,4-dione (Compound 7)

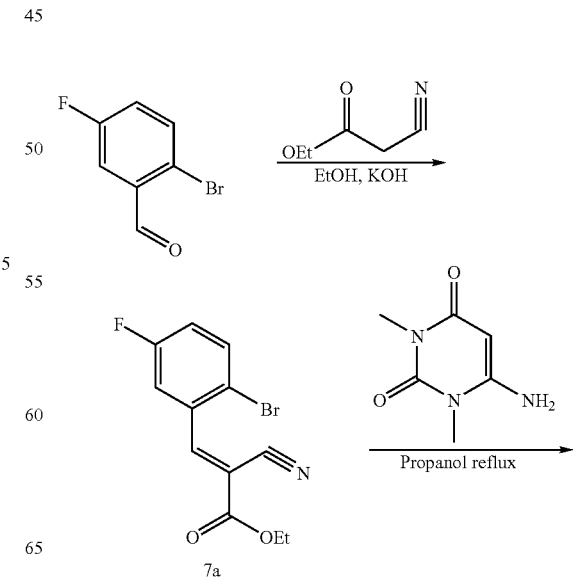

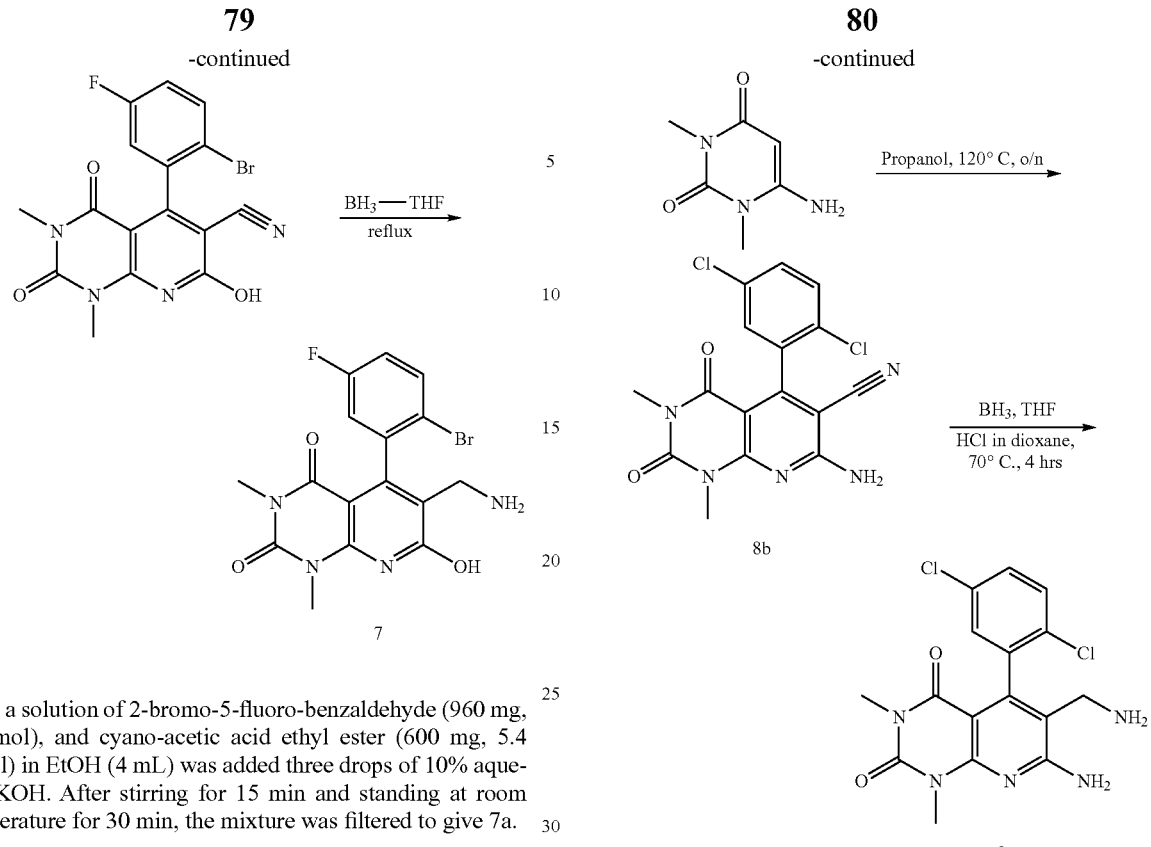

To a solution of 2-bromo-5-fluoro-benzaldehyde (960 mg, 5 mmol), and cyano-acetic acid ethyl ester (600 mg, 5.4 mmol) in EtOH (4 mL) was added three drops of 10% aqueous KOH. After stirring for 15 min and standing at room temperature for 30 min, the mixture was filtered to give 7a.

7a (300 mg) and 6-amino-1,3-dimethyl uracil (500 mg) in propanol (5 mL) was refluxed overnight. After general workup and $BH_3$ reduction as described in the synthesis of Example 1, 6-Aminomethyl-5-(2-bromo-5-fluoro-phenyl)-7-hydroxy-1,3-dimethyl-1H-pyrido[2,3-d]pyrimidine-2,4-dione (Compound 7) was isolated by LC-MS as the TFA salt. $^1$H NMR (400 MHz, $CDCl_3$—$CD_3OD$ 10:1) δ 7.56 (dd, J=8.8, 5.1 Hz, 1H) 6.99 (td, J=8.3, 2.8 Hz, 1H) 6.92 (dd, J=8.3, 3.0 Hz, 1H) 3.79, 3.45 (ABq, J=13.6, 135.9 Hz, 2H) 3.59 (s, 3H), 3.22 (s, 3H). [M-$NH_2$] calc'd for $C_{16}H_{13}BrFN_3O_3$, 393; found, 393.

Example 7

Preparation of 7-Amino-6-aminomethyl-5-(2,5-dichloro-phenyl)-1,3-dimethyl-1H-pyrido[2,3-d]pyrimidine-2,4-dione (Compound 8)

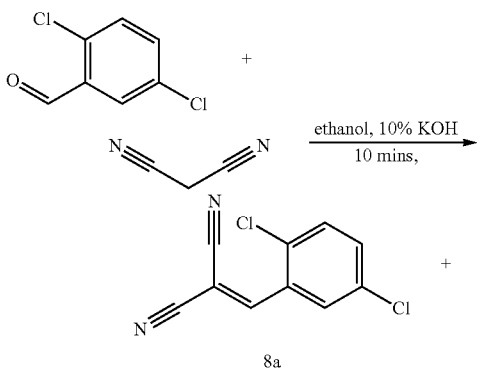

To a solution of 2,5-dichlorbenzaldehyde (4.0 g, 0.0228 mole) in ethanol (6 ml) was added malononitrile (1.52 g, 0.0228 mole), followed by 100 μl, of 10% $KOH/H_2O$. The mixture was stirred at room temperature for 2 hrs and then filtered to give 2-(2,5-Dichloro-benzylidene)-malononitrile (8a, 4.82 g) in 95% yield. $^1$H-NMR (400 MHz, $d_6$-DMSO): δ ppm 8.66 (s, 1H), 8.07 (d, J=2.0 Hz, 1H), 7.74 (s, 1H), 7.74 (s, 1H). MS [m+H] calc'd for $C_{10}H_4Cl_2N_2$, 223.0, 224.8; found 223.0, 224.8.

Compound 8a (4.82 g, 0.0204 mole) and 6-amino-1,3-dimethyluracil (6.34 g, 0.041 mole) were suspended in 6 ml of propanol. The mixture was heated to 120° C. overnight, and then concentrated in vacuo. The residue was dissolved in EtOAc and washed with 10% $HCl/H_2O$ and $H_2O$, dried ($Na_2SO_4$), filtered, then concentrated in vacuo. The crude product was carried onto the next step without further purification. An amount of 3.3 g (43% yield) of 7-amino-5-(2,5-dichloro-phenyl)-1,3-dimethyl-2,4-dioxo-1,2,3,4-tetrahydropyrido[2,3-c]pyrimidine-6-carbonitrile (8b) was collected. $^1$H-NMR (400 MHz, $d_6$-DMSO): δ ppm 8.03 (br s, 1H), 7.58 (d, J=8.4 Hz, 1H), 7.52 (dd, $J_1$=2 Hz, $J_2$=8.4 Hz, 2H), 7.42 (d, J=2.4 Hz, 1H), 3.58 (s, 3H), 3.05 (s, 3H). MS [m+H] calc'd for $C_{16}H_{11}Cl_2N_5O_2$, 375.9, 377.7; found 375.9, 377.7.

To a cold (0° C.-2° C.) solution of Compound 8b (50 mg, 0.1329 mmole) in 500 μL of anhydrous THF, was added a 1M solution of $BH_3$ in THF (531.6 μL, 0.5316 mmole) under nitrogen, followed by 400 μL of 1N HCl in Dioxane. The mixture was stirred at room temp. for about 10 min., then heated to 70° C. for 3 hrs. After cooling, to the reaction was added 1N $HCl/H_2O$ until no more bubbling occurred, followed by MeOH, plus a few drops of TFA. The residue was then dried in vacuo. The product was purified by prep. HPLC and concentrated. The resulting product was washed in EtOAc, and filtered to give 23.0 mg (46%) of 7-amino-6-aminomethyl-5-(2,5-dichloro-phenyl)-1,3-dimethyl-1H-pyrido[2,3-d]pyrimidine-2,4-dione (Compound 8). $^1$H-NMR (400 MHz, d$_6$-DMSO): δ ppm 8.08 (s, 3H), 7.642 (s, 2H), 7.6195 (d, J=8.4 Hz, 1H), 7.564 (dd, J$_1$=2.4 Hz, J$_2$=8.4 Hz, 1H), 7.494 (d, J=2.4 1H), 3.59 (s, 3H), 3.32 (m, 1H), 3.31 (d, J=9.2 1H), 3.23 (s, 3H). MS [m+H] calc'd for C$_{16}$H$_{11}$Cl$_2$N$_5$O$_2$, 379.85, 381.87; found 379.85, 381.87.

Example 8

Preparation of 7-amino-6-aminomethyl-5-(2-bromo-5-fluoro-phenyl)-1,3-dimethyl-1H-pyrido[2,3-d]pyrimidine-2,4-dione (Compound 9)

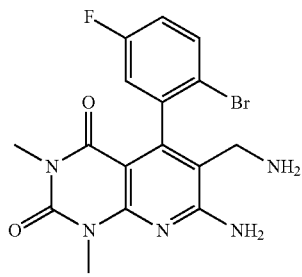

The title compound was prepared using the procedures described in the preparation of Compound 8 (Example 7). $^1$H-NMR (400 MHz, d$_6$-DMSO): δ ppm 7.94 (s, 3H), 7.64 (q, J=4.8 Hz, 1H), 7.50 (s, 2H), 7.16 (m, J=14.8 Hz, 2H), 3.77 (d, J=7.2 Hz, 1H), 3.45 (s, 3H), 3.17 (d, J=6.4 1H), 3.02 (s, 3H). MS [m+H] calc'd for C$_{16}$H$_{15}$BrFN$_5$O$_2$, 407.81, 409.79; found 407.81, 409.79.

Example 9

Preparation of 7-amino-6-aminomethyl-5-(2-bromo-phenyl)-1,3-dimethyl-1H-pyrido[2,3-d]pyrimidine-2,4-dione (Compound 10)

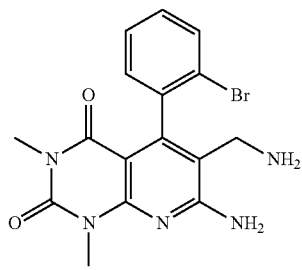

The title compound was prepared using the procedures described in the preparation of Compound 8 (Example 7). $^1$H-NMR (400 MHz, d$_6$-DMSO): δ ppm 7.86 (br s, 3H), 7.81 (d, J=8.0 Hz, 1H), 7.59 (t, J=7.6 Hz, 1H), 7.56 (br s, 2H), 7.48 (td, J$_1$=1.6 Hz, J$_2$=7.6 Hz, 1H), 7.40 (dd, J$_1$=1.6 Hz, J$_2$=7.6 Hz, 1H), 3.94 (d, J=14.8 Hz, 1H), 3.66 (s, 3H), 3.51 (d, J=8.4 Hz, 1H), 3.21 (s, 3H). MS [m+H] calc'd for C$_{16}$H$_{16}$BrN$_5$O$_2$, 391.87, 392.78; found 391.87, 392.78.

Example 10

Preparation of 7-amino-6-aminomethyl-1,3-dimethyl-5-(3-methyl-thiophen-2-yl)-1H-pyrido[2,3-d]pyrimidine-2,4-dione (Compound 11)

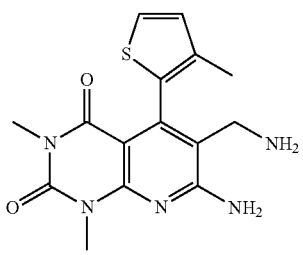

The title compound was prepared using the procedures described in the preparation of Compound 8 (Example 7). The only difference was that after the synthesis of 2-(3-methyl-thiophen-2-ylmethylene)-malononitrile, the reaction was carried onto the next step without further work-up or purification, and propanol was used instead of ethanol. Furthermore, after the hydrogenation using BH$_3$.THF, the reaction mixture was concentrated. An ample amount of MeOH was added until there was no more bubbling. The mixture was dried in vacuo, and purified by prep. HPLC. After washing the product with EtOAc, an amount of 82.4 mg (17.1% yield) of the title compound was collected. $^1$H NMR (400 MHz, d$_6$-DMSO): δ ppm 7.80 (br s, 3H), 7.53 (d, J=4.0 Hz, 1H), 7.36 (br s, 2H), 6.96 (d, J=4.0 Hz, 1H), 3.80 (m, 2H), 3.51 (s, 3H), 3.10 (s, 3H). MS [m+H] calc'd for C$_{15}$H$_{17}$N$_5$O$_2$S, 332.0, 333.2. found 332.0, 333.2.

Example 11

Preparation of 7-amino-6-aminomethyl-5-(2-chloro-phenyl)-1,3-dimethyl-1H-pyrido[2,3-d]pyrimidine-2,4-dione (Compound 12)

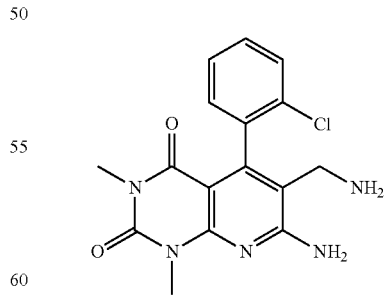

The title compound was prepared using the procedures described in the preparation of Compound 11. $^1$H NMR (400 MHz, d$_6$-DMSO): δ ppm 7.79 (br s, 3H), 7.51 (dd, J$_1$=1.6 Hz, J$_2$=7.6 Hz, 1H), 7.41 (m, 3H), 7.27 (dd, J$_1$=2.0 Hz, J$_2$=7.2 Hz, 1H), 3.83 (d, J=14.4 Hz, 1H), 3.52 (s, 3H), 3.24 (m, 1H), 3.07

Example 12

Preparation of 7-amino-6-aminomethyl-5-(4-fluorophenyl)-1,3-dimethyl-1H-pyrido[2,3-d]pyrimidine-2,4-dione (Compound 13)

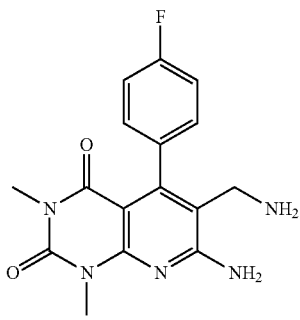

The title compound was prepared using the procedures described in the preparation of Compound 11. $^1$H-NMR (400 MHz, d$_6$-DMSO): δ ppm 7.40 (br s, 3H), 7.16 (m, 6H), 3.51 (s, 3H), 3.23 (s, 2H), 3.06 (s, 3H). MS [m+H] calc'd for C$_{16}$H$_{16}$FN$_5$O$_2$, 329.93, 330.91; found 329.93, 330.91.

Example 13

Preparation of 7-amino-6-aminomethyl-5-(5-chlorothiophen-2-yl)-1,3-dimethyl-1H-pyrido[2,3-d]pyrimidine-2,4-dione (Compound 14)

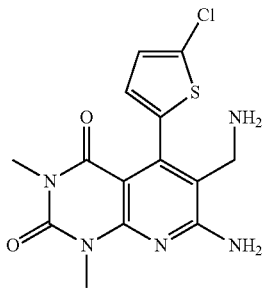

The title compound was prepared using the procedures described in the preparation of Example 11. $^1$H-NMR (400 MHz, d$_6$-DMSO): δ ppm 7.49 (br s, 2H), 7.08 (d, J=3.6 Hz, 1H), 6.77 (d, J=3.6 Hz, 1H), 3.50 (s, 3H), 3.38 (s, 2H), 3.12 (s, 3H). MS [m+H] calc'd for C$_{14}$H$_{14}$ClN$_5$O$_2$S, 351.87, 353.82. found 351.87, 353.82 345.90, 347.91.

Example 14

Preparation of 7-amino-6-aminomethyl-5-(4-bromophenyl)-1,3-dimethyl-1H-pyrido[2,3-d]pyrimidine-2,4-dione (Compound 15)

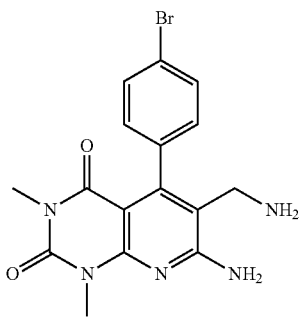

The title compound was prepared using the procedures described in the preparation of Compound 11. $^1$H-NMR (400 MHz, d$_6$-DMSO): δ ppm 7.54 (d, J=8.0 Hz, 2H), 7.41 (br s, 2H), 7.08 (d, J=8.4 Hz, 2H), 3.51 (s, 3H), 3.20 (s, 2H), 3.06 (s, 3H). MS [m+H] calc'd for C$_{16}$H$_{16}$BrN$_5$O$_2$, 391.80, 392.78; found 391.80, 392.78.

Example 15

Preparation of 7-amino-6-aminomethyl-5-(2,3-dichloro-phenyl)-1,3-dimethyl-1H-pyrido[2,3-d]pyrimidine-2,4-dione (Compound 16)

The title compound was prepared using the procedures described in the preparation of Compound 11. $^1$H-NMR (400 MHz, d$_6$-DMSO): δ ppm 7.62 (d, J=8.0 Hz, 1H), 7.52 (b, 2H), 7.37 (t, J=8.0 Hz, 1H), 7.17 (d, J=7.6 Hz, 1H), 3.52 (s, 3H), 3.26 (d, J=14.0 Hz, 1H), 3.15 (d, J=13.6 Hz, 1H), 3.08 (s, 3H). MS [m+H] calc'd for C$_{16}$H$_{15}$Cl$_2$N$_5$O$_2$, 379.79, 381.80; found 379.79, 381.80.

(previous page continuation: (s, 3H). MS [m+H] calc'd for C$_{16}$H$_{16}$ClN$_5$O$_2$, 345.90, 347.91; found 345.90, 347.91.)

Example 16

Preparation of 7-amino-6-aminomethyl-5-(2-chloro-6-fluoro-phenyl)-1,3-dimethyl-1H-pyrido[2,3-d]pyrimidine-2,4-dione (Compound 17)

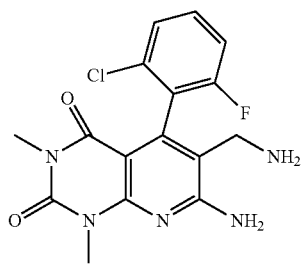

The title compound was prepared using the procedures described in the preparation of Compound 11. $^1$H-NMR (400 MHz, $d_6$-DMSO): δ ppm 7.84 (br s, 3H), 7.56 (br s, 2H), 7.52 (m, 1H), 7.42 (d, J=8.0 Hz, 1H), 7.32 (t, J=8.4 Hz, 1H), 3.72 (d, J=14.4 Hz, 1H), 3.54 (s, 3H), 3.49 (d, J=14.8 Hz, 1H), 3.1 (s, 3H). MS [m+H] calc'd for $C_{16}H_{15}ClFN_5O_2$, 363.88, 365.89, and 366.87. found 363.88, 365.89, and 366.87.

Example 17

Preparation of 7-amino-6-aminomethyl-5-(3-methoxy-phenyl)-1,3-dimethyl-1H-pyrido[2,3-d]pyrimidine-2,4-dione (Compound 18)

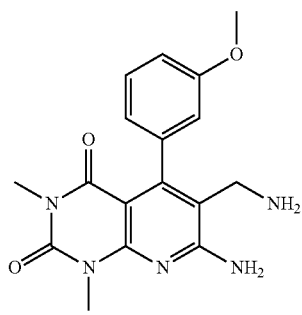

The title compound was prepared using the procedures described in the preparation of Compound 11. $^1$H-NMR (400 MHz, $d_6$-DMSO): δ ppm 7.88 (br s, 3H), 7.50 (br s, 2H), 7.44 (m, J=8.0 Hz, 1H), 7.07 (dd, $J_1$=2.8 Hz, $J_2$=8.4 Hz, 1H), 6.88 (s, 1H), 6.82 (d, J=7.6 Hz, 1H), 3.88 (s, 3H), 3.72 (d, J=14.4 Hz, 1H), 3.65 (d, J=14.4 Hz, 1H), 3.65 (s, 3H). MS [m+H] calc'd for $C_{17}H_{19}N_5O_3$, 342.2, 343.2; found 342.2, 343.2.

Example 18

Preparation of 7-amino-6-aminomethyl-5-(2-methoxy-phenyl)-1,3-dimethyl-1H-pyrido[2,3-d]pyrimidine-2,4-dione (Compound 19)

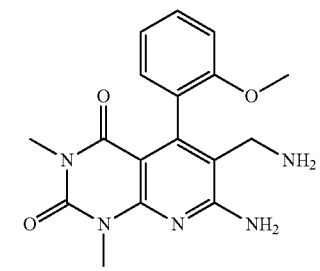

The title compound was prepared using the procedures described in the preparation of Compound 11. $^1$H-NMR (400 MHz, $d_6$-DMSO): δ ppm 7.69 (br s, 3H), 7.38 (td, $J_1$=1.6 Hz, $J_2$=8.8 Hz, 1H), 7.27 (br s, 2H), 7.02 (m, 3H), 3.74 (d, J=16.8 Hz, 1H), 3.63 (s, 3H), 3.40 (d, J=14.4 Hz, 1H), 3.51 (s, 3H). MS [m+H] calc'd for $C_{17}H_{19}N_5O_3$, 342.0, 343.1, and 344.2. found 342.0, 343.1, and 344.2.

Example 19

Preparation of -amino-6-aminomethyl-5-(2-chloro-3,6-difluorophenyl)-1,3-dimethyl-1H-pyrido[2,3-d]pyrimidine-2,4-dione (Compound 20)

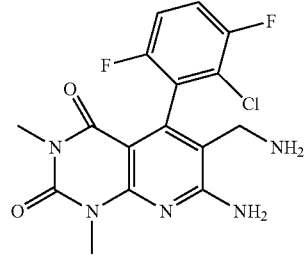

The title compound was prepared using the procedures described in the preparation of Compound 11. $^1$H-NMR (400 MHz, $d_6$-DMSO): δ ppm 7.64 (br s, 3H), 7.51 (td, $J_1$=4.8 Hz, $J_2$=8.8 Hz, 1H), 7.34 (td, $J_1$=4.0 Hz, $J_2$=8.8 Hz, 1H), 3.53 (s, 3H), 3.29 (d, J=8.4 Hz, 2H), 3.10 (s, 3H). MS [m+H] calc'd for $C_{16}H_{14}ClF_2N_5O_2$, 381.80, 383.81 and 384.85. found 381.80, 383.81 and 384.85.

Example 20

Preparation of 7-amino-6-aminomethyl-5-phenyl-1,3-dimethyl-1H-pyrido[2,3-d]pyrimidine-2,4-dione (Compound 21)

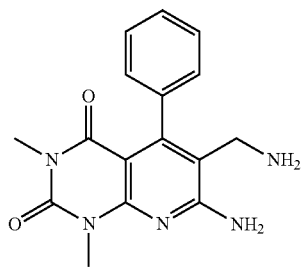

The title compound was prepared using the procedures described in the preparation of Compound 11. $^1$H-NMR (400 MHz, d$_6$-DMSO): δ ppm 7.34 (m, 5H), 7.10 (dd, J$_1$=1.6 Hz, J$_2$=7.2 Hz, 2H), 3.52 (s, 3H), 3.19 (s, 2H), 3.06 (s, 3H). MS [m+H] calc'd for C$_{16}$H$_{17}$N$_5$O$_2$, 311.96, 312.93; found 311.96, 312.93.

Example 21

Preparation of 7-amino-6-aminomethyl-5-(3-bromo-thiophen-2-yl)-1,3-dimethyl-1H-pyrido[2,3-d]pyrimidine-2,4-dione (Compound 22)

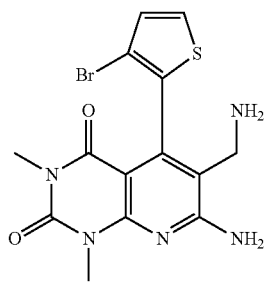

The title compound was prepared using the procedures described in the preparation of Compound 11. $^1$H-NMR (400 MHz, d$_6$-DMSO): δ ppm 7.88 (s, 3H), 7.80 (d, J=5.2 Hz, 1H), 7.48 (s, 2H), 7.17 (d, J=5.2 Hz, 1H), 3.87 (d, J=14.4 Hz, 1H), 3.51 (s, 3H), 3.47 (d, J=14.4 Hz, 1H), 3.06 (s, 3H). MS [m+H] calc'd for C$_{14}$H$_{14}$BrN$_5$O$_2$S, 397.8. found 397.8.

Example 22

Preparation of 7-amino-6-aminomethyl-5-(2-chloro-5-fluoro-phenyl)-1,3-dimethyl-1H-pyrido[2,3-d]pyrimidine-2,4-dione (Compound 23)

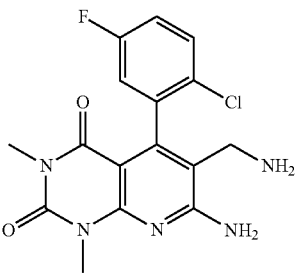

The title compound was prepared using the procedures described in the preparation of Compound 11. $^1$H-NMR (400 MHz, d$_6$-DMSO): δ ppm 7.75 (br s, 3H), 7.58 (dd, J$_1$=5.2 Hz, J$_2$=9.2 Hz, 1H), 7.53 (br s, 2H), 7.33 (td, J$_1$=2.8 Hz, J$_2$=8.4 Hz, 1H), 7.20 (dd, J$_1$=2.8 Hz, J$_2$=8.8 Hz, 1H), 3.84 (d, J=14.4 Hz, 1H), 3.53 (s, 3H), 3.23 (d, J=14.4 Hz, 1H), 3.09 (s, 3H). MS [m+H] calc'd for C$_{16}$H$_{15}$ClFN$_5$O$_2$, 363.88, 365.83, and 366.87. found 363.88, 365.83, and 366.87.

Example 23

Preparation of 7-amino-6-aminomethyl-5-(2-bromo-5-fluoro-phenyl)-1,3-dimethyl-1H-pyrido[2,3-d]pyrimidine-2,4-dione (Compound 24)

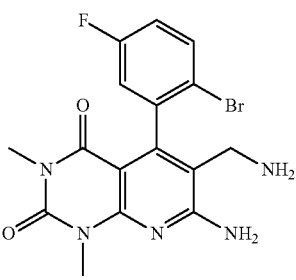

The title compound was prepared using the procedures described in the preparation of Compound 11. $^1$H-NMR (400 MHz, d$_6$-DMSO): δ ppm 8.11 (s, 3H), 7.70 (dd, J$_1$=5.2 Hz, J$_2$=8.4 Hz, 1H), 7.61 (s, 2H), 7.23 (m, 2H), 3.83 (d, J=14.4 Hz, 1H), 3.51 (s, 3H), 3.22 (d, J=14.4 Hz, 1H), 3.08 (s, 3H). MS m+H] calc'd for C$_{16}$H$_{15}$BrFN$_5$O$_2$, 407.81, and 409.79. found 407.81, and 409.79.

Example 24

Preparation of 7-amino-6-aminomethyl-5-(2-chloro-4-fluoro-phenyl)-1,3-dimethyl-1H-pyrido[2,3-d]pyrimidine-2,4-dione (Compound 25)

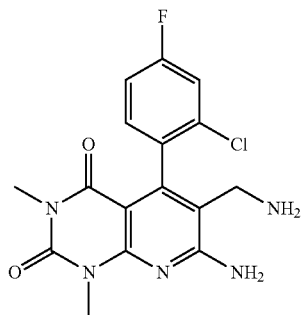

The title compound was prepared using the procedures described in the preparation of Compound 11. $^1$H-NMR (400 MHz, d$_6$-DMSO): δ ppm 7.80 (br s, 2H), 7.74 (d, J=2.0 Hz, 1H), 7.52 (m, 2H), 7.32 (m, 2H), 3.79 (d, J=8.8 Hz, 1H), 3.49 (s, 3H), 3.28 (d, J=8.8 Hz, 1H), 3.08 (s, 3H). MS m+H] calc'd for $C_{16}H_{15}ClFN_5O_2$, 363.88, 365.83; found 363.88, 365.83.

Example 25

Preparation of 7-amino-6-aminomethyl-5-cyclopentyl-1,3-dimethyl-1H-pyrido[2,3-d]pyrimidine-2,4-dione (Compound 26)

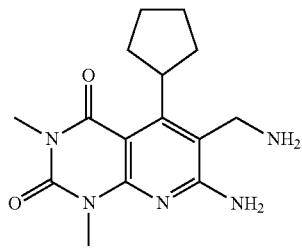

The title compound was prepared using the procedures described in the preparation of Compound 11, with the exception that it was extracted with saturated NaHCO$_3$ and EtOAc, instead of 1N HCl. $^1$H-NMR (400 MHz, d6-DMSO): δ ppm 7.22 (br s, 2H), 3.68 (s, 2H), 3.47 (s, 3H), 3.22 (s, 3H), 1.92 (m, 8H), 1.74 (m, 1H). MS m+H] calc'd for $C_{15}H_{21}N_5O_2$, 304.1, 305.2; found 304.1, 305.2.

Example 26

Preparation of 7-amino-6-aminomethyl-1,3-dimethyl-5-pyridin-3-yl-1H-pyrido[2,3-d]pyrimidine-2,4-dione (Compound 27)

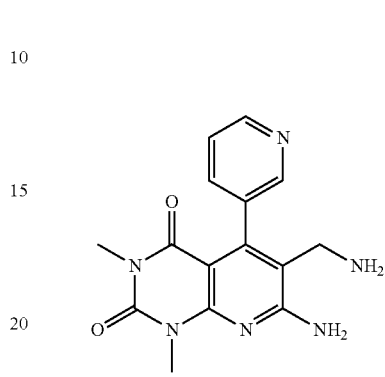

The title compound was prepared using the procedures described in the preparation of Compound 26. $^1$H-NMR (400 MHz, d6-DMSO): δ ppm 8.63 (d, J=5.2, 1H), 8.41 (br s, 1H), 7.77 (br s, 3H), 7.68 (d, J=8.4 Hz, 1H), 7.53 (m, 3H), 3.57 (d, J=5.6, 2H), 3.52 (s, 3H), 3.05 (s, 3H). MS [m+H] calc'd for $C_{15}H_{16}N_6O_2$, 313.2, 314.3; found 313.2, 314.3.

Example 27

Preparation of 7-amino-6-aminomethyl-5-(4,5-dimethyl-thiophen-2-yl)-1,3-dimethyl-1H-pyrido[2,3-d]pyrimidine-2,4-dione (Compound 28)

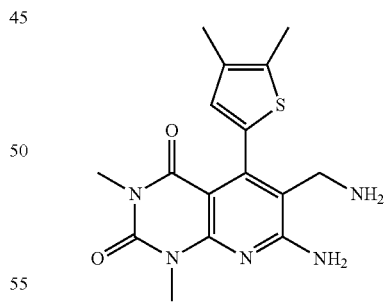

The title compound was prepared using the procedures described in the preparation of Compound 26. $^1$H-NMR (400 MHz, d6-DMSO): δ ppm 7.78 (br s, 3H), 7.41 (br s, 2H), 6.67 (s, 1H), 3.75 (br s, 1H), 3.65 (br s, 1H), 3.51 (s, 3H), 3.12 (s, 3H), 2.34 (s, 3H), 2.12 (s, 3H). MS [m+H] calc'd for $C_{16}H_{19}N_5O_2S$, 346.1, 347.3. found 346.1, 347.3.

Example 28

Preparation of 7-amino-6-aminomethyl-5-(5-fluoro-2-nitro-phenyl)-1,3-dimethyl-1H-pyrido[2,3-d]pyrimidine-2,4-dione (Compound 29)

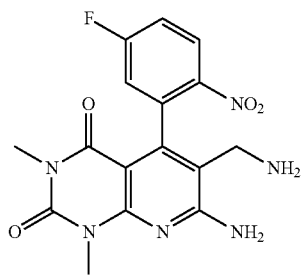

The title compound was prepared using the procedures described in the preparation of Compound 26. $^1$H-NMR (400 MHz, d6-DMSO): δ ppm 8.40 (dd, J1=5.2 Hz, J2=9.2 Hz, 1H), 7.68 (br s, 4H), 7.57 (m, 1H), 7.25 (dd, J1=2.8 Hz, J2=8.8 Hz, 1H), 3.69 (d, J=14.8 Hz, 1H), 3.53 (s, 3H), 3.49 (d, J=13.6 Hz, 1H), 3.04 (s, 3H). MS [m+H] calc'd for $C_{16}H_{15}FN_6O_4$, 375.04, 376.21; found 375.04, 376.21.

Example 29

Preparation of 7-amino-6-aminomethyl-1,3-dimethyl-5-(3-methyl-3H-imidazol-4-yl)-1H-pyrido[2,3-d]pyrimidine-2,4-dione (Compound 30)

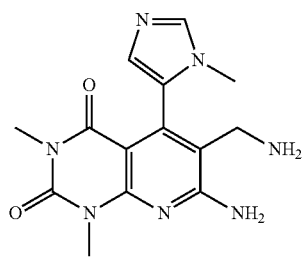

The title compound was prepared using the procedures described in the preparation of Compound 26. $^1$H-NMR (400 MHz, d6-DMSO): δ ppm 9.09 (bs, 1H), 7.92 (bs, 3H), 7.69 (bs, 2H), 7.59 (s, 1H), 3.90 (d, J=15.2 Hz, 1H), 3.51 (s, 4H), 3.41 (s, 3H), 3.11 (s, 3H). MS [m+H] calc'd for $C_{14}H_{17}N_7O_2$, 316.1, 317.3; found 316.1, 317.3.

Example 30

Preparation of 7-amino-6-aminomethyl-5-benzo[b]thiophen-2-yl-1,3-dimethyl-1H-pyrido[2,3-d]pyrimidine-2,4-dione (Compound 31)

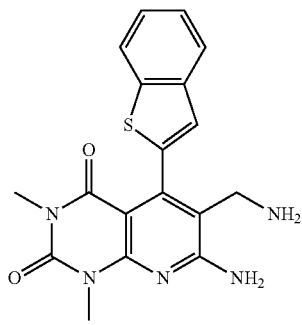

The title compound was prepared using the procedures described in the preparation of Compound 26. $^1$H-NMR (400 MHz, d6-DMSO): δ ppm 8.0 (d, J=8.4 Hz, 1H), 7.85 (m, 4H), 7.53 (br s, 2H), 7.42 (m, 2H), 7.33 (s, 1H), 3.84 (d, J=14.4 Hz, 1H), 3.62 (d, J=14.4 Hz, 1H), 3.53 (s, 3H), 3.09 (s, 3H). MS [m+H] calc'd for $C_{18}H_{17}N_5O_2S$, 368.08, 369.25. found 368.08, 369.25.

Example 31

Preparation of 7-amino-6-aminomethyl-1,3-dimethyl-5-(3-methyl-benzo[b]thiophen-2-yl)-1H-pyrido[2,3-d]pyrimidine-2,4-dione (Compound 32)

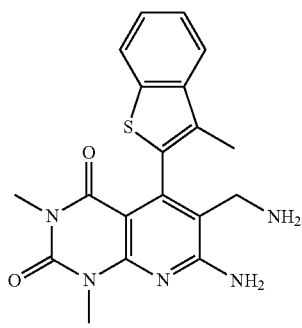

The title compound was prepared using the procedures described in the preparation of Compound 26. $^1$H-NMR (400 MHz, d6-DMSO): δ ppm 7.96 (d, J=8.0 Hz, 1H), 7.82 (br s, 3H), 7.77 (d, J=7.2 Hz, 1H), 7.43 (m, 4H), 3.65 (b, 2H), 3.53 (s, 3H), 3.07 (s, 3H), 2.02 (s, 3H). MS [m+H] calc'd for $C_{19}H_{19}N_5O_2S$, 382.1, 383.2. found 382.1, 383.2.

Example 32

Preparation of 6-(aminomethyl)-5-(2,4-dichlorophenyl)-7-hydroxy-1,3-dimethylpyrido[2,3-d]pyrimidine-2,4(1H,3H)-dione (Compound 33) and 6-(aminomethyl)-7-chloro-5-(2,4-dichlorophenyl)-1,3-dimethylpyrido[2,3-d]pyrimidine-2,4(1H,3H)-dione (Compound 34)

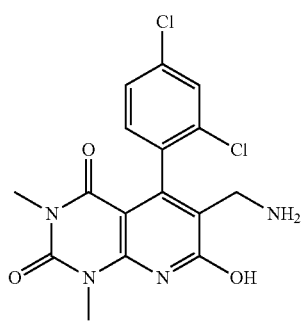

33

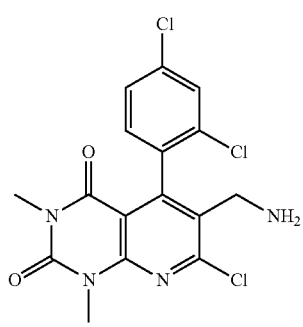

34

To a solution of Compound 1b (Example 1, 200 mg, 1.3 mmol) in a mixture of AcOH and concentrated HCl (2:1, 3 mL) was added a solution of $NaNO_2$ (400 mg) in water (0.5 mL). After 30 minutes, the mixture was concentrated, diluted with water and extracted with DCM 3 times. The organic phase was washed with water and dried over $Na_2SO_4$. The crude residue was treated with 1M $BH_3$-THF (7.8 mL, 7.8 mmol) at rt for 5 min, and then at reflux for 1 h. The mixture was concentrated in vacuo, co-evaporated with MeOH, and purified by LC-MS to give Compound 33 and Compound 34.

Compound 33: $^1$H-NMR (400 MHz, $CDCl_3$—$CD_3OD$ 10:1) δ 7.40 (d, J=2.0 Hz, 1H) 7.24-7.28 (dd, J=1.7 and 8.4 Hz, 1H) 7.05 (d, J=8.1 Hz, 1H) 3.72 (d, J=13.9 Hz, 1H) 3.55 (s, 3H) 3.42 (d, J=13.9 Hz, 1H) 3.16 (s, 3H). [M-H] calc'd for $C_{16}H_{15}Cl_2N_4O_3$, 382; found, 382. [M-$NH_2$] calc'd for $C_{16}H_{12}Cl_2N_3O_3$, 364; found, 364.

Compound 34: $^1$H-NMR (400 MHz, $CDCl_3$—$CD_3OD$ 10:1) δ 7.44 (d, J=1.5 Hz, 1H) 7.31 (dd, J=8.1, 1.5 Hz, 1H) 7.11 (d, J=8.1 Hz, 1H) 3.96 (d, J=13.4 Hz, 1H) 3.62 (s, 3H) 3.26 (d, J=13.4 Hz, 1H) 3.20 (s, 3H).

Example 33

Preparation of 7-amino-6-(aminomethyl)-5-(2-chloro-5-fluorophenyl)-3-methylpyrido[2,3-d]pyrimidine-2,4(1H,3H)-dione (Compound 35)

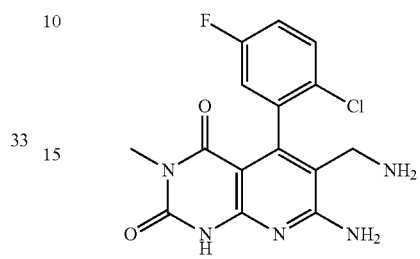

The title compound was synthesized using the procedure described in the synthesis of Compound 1. $^1$H-NMR (400 MHz, $CDCl_3$—$CD_3OD$ 10:1) δ 7.55 (d, J=13.9 Hz, 1H) 7.24 (td, J=8.5, 2.9 Hz, 1H) 7.08 (dd, J=8.6, 3.0 Hz, 1H) 3.91 (d, J=14.9 Hz, 1H) 3.62 (d, J=14.7 Hz, 1H) 3.17 (s, 3H). [M-H] calc'd for $C_{15}H_{16}ClFN_5O_2$, 350; found 350. [M-$NH_2$] calc'd for $C_{15}H_{11}ClFN_4O_2$, 333; found, 333.

Example 34

Preparation of 7-amino-6-(aminomethyl)-5-(2-(aminomethyl)phenyl)-1,3-dimethylpyrido[2,3-d]pyrimidine-2,4(1H,3H)-dione (Compound 36) and 2-(7-amino-6-(aminomethyl)-1,3-dimethyl-2,4-dioxo-1,2,3,4-tetrahydropyrido[2,3-d]pyrimidin-5-yl)benzonitrile (Compound 37) and 7-amino-5-(2-(aminomethyl)phenyl)-1,3-dimethyl-2,4-dioxo-1,2,3,4-tetrahydropyrido[2,3-d]pyrimidine-6-carbonitrile (Compound 38)

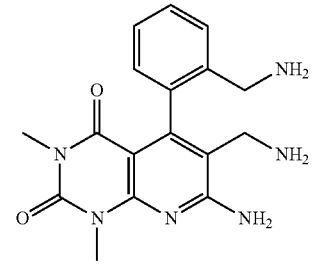

36

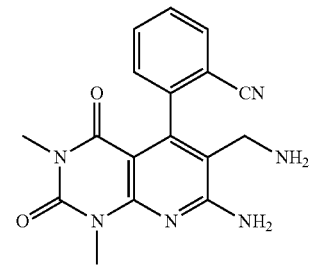

37

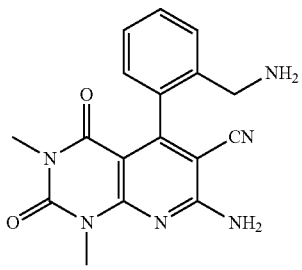

38

Compounds 36, 37 and 38 were synthesized using the procedures described in the synthesis of Compound 1 (Example 1). The three compounds were isolated by LC-MS.

Compound 36: $^1$H-NMR (400 MHz, CDCl$_3$—CD$_3$OD 10:1) δ 7.37-7.44 (m, 2H) 7.33 (td, J=7.1, 2.0 Hz, 1H) 6.82-6.88 (d, J=7.1 Hz, 1H) 3.82 (d, J=14.4 Hz, 2H) 3.73 (d, J=14.4 Hz, 2H) 3.60 (d, J=1.5 Hz, 2H) 3.52 (s, 3H) 3.11 (s, 3H). [M-H] calc'd for C$_{17}$H$_{21}$N$_6$O$_2$, 341; found, 341. [M-NH$_2$] calc'd for C$_{17}$H$_{18}$N$_5$O$_2$, 324; found, 324.

Compound 37: $^1$H-NMR (400 MHz, CDCl$_3$—CD$_3$OD 10:1) δ 7.70 (dd, J=7.4, 1.1 Hz, 1H) 7.62 (td, J=7.7, 1.3 Hz, 1H) 7.47 (td, J=7.8, 1.1 Hz, 1H) 7.21 (d, J=7.3 Hz, 1H) 3.68 (d, J=14.9 Hz, 1H) 3.54 (d, J=14.9 Hz, 1H) 3.53 (s, 3H) 3.12 (s, 3H). [M-H] calc'd for C$_{17}$H$_{17}$N$_6$O$_2$, 336; found, 336. [M-NH$_2$] calc'd for C$_{17}$H$_{14}$N$_5$O$_2$, 320; found, 320.

Compound 38: $^1$H-NMR (400 MHz, CDCl$_3$—CD$_3$OD 10:1) δ 7.46-7.52 (m, 2H) 7.43 (td, J=7.1, 2.1 Hz, 1H) 7.03 (dd, J=7.2, 1.1 Hz, 1H) 3.92 (d, J=13.9 Hz, 1H) 3.75 (d, J=13.9 Hz, 1H) 3.56-3.59 (s, 3H) 3.18 (s, 3H). [M-H] calc'd for C$_{17}$H$_{17}$N$_6$O$_2$, 336; found, 336. [M-NH$_2$] calc'd for C$_{17}$H$_{14}$N$_5$O$_2$, 320; found, 320.

Example 35

Preparation of 6-(aminomethyl)-7-(cyclopropylmethylamino)-5-(2,4-dichlorophenyl)-1,3-dimethylpyrido[2,3-d]pyrimidine-2,4(1H,3H)-dione (Compound 39)

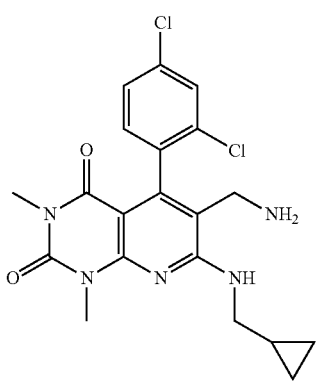

The title compound was synthesized using the procedures described in the synthesis of Compound 4. $^1$H-NMR (400 MHz, CDCl$_3$—CD$_3$OD 10:1) δ 7.48 (d, J=2.0 Hz, 1H) 7.32 (dd, J=8.2, 1.9 Hz, 1H) 7.04 (d, J=8.3 Hz, 1H) 3.75 (d, J=14.6 Hz, 1H) 3.61 (s, 3H) 3.59 d, J=14.6 Hz, 1H) 3.36 (d, J=7.1 Hz, 2H) 3.20 (s, 3H) 1.12-1.22 (m, 1H) 0.45-0.51 (m, 2H) 0.22-0.27 (m, 2H). [M-H] calc'd for C$_{20}$H$_{22}$Cl$_2$N$_5$O$_2$, 434; found, 434. [M-NH$_2$] calc'd for C$_{20}$H$_{19}$Cl$_2$N$_4$O$_2$, 417; found, 417.

Example 36

Preparation of 2-(7-amino-6-(aminomethyl)-1-isobutyl-3-methyl-2,4-dioxo-1,2,3,4-tetrahydropyrido[2,3-d]pyrimidin-5-yl)benzonitrile (Compound 40)

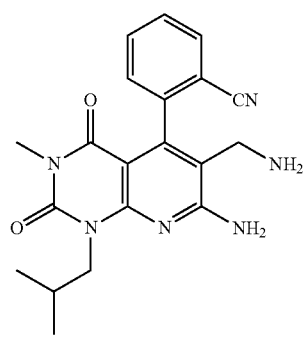

The title compound was synthesized using the procedures described in the preparation of Compound 1. $^1$H-NMR (400 MHz, CDCl$_3$—CD$_3$OD 10:1) δ 7.74 (dd, J=7.8, 1.0 Hz, 1H) 7.67 (td, J=7.7, 1.3 Hz, 1H) 7.52 (td, J=7.7, 1.0 Hz, 1H) 7.23-7.26 (m, 1H) 4.07 (dd, J=7.5, 2.1 Hz, 2H) 3.69 (d, J=15.0 Hz, 1H) 3.60 (d, J=15.0 Hz, 1H) 3.17 (s, 3H) 2.13-2.25 (m, 1H) 0.89 (dd, J=6.8, 2.3 Hz, 6H). [M-H] calc'd for C$_{20}$H$_{23}$N$_6$O$_2$, 379; found, 379. [M-NH$_2$] calc'd for C$_{20}$H$_{20}$N$_5$O$_2$, 362; found, 362.

Example 37

Preparation of 6-(aminomethyl)-5-(2,4-dichlorophenyl)-1,3-dimethylpyrido[2,3-d]pyrimidine-2,4(1H,3H)-dione (Compound 41)

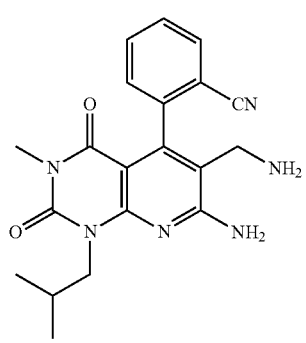

Compound 34 (Example 32, 70 mg, 0.19 mmol) in a mixture of THF (5 mL) and DIPEA (0.2 mL) was stirred with 10% Pd/C (20 mg) under H$_2$ atmosphere for 4 h, and then filtered and concentrated. The residue was purified by LC-MS to give the title compound. $^1$H-NMR (400 MHz, CDCl$_3$—CD$_3$OD 10:1) δ 8.83 (s, 1H) 7.49 (d, J=1.5 Hz, 1H) 7.35 (dd, J=8.2, 1.6 Hz, 1H) 7.10 (d, J=8.1 Hz, 1H) 3.85 (d, J=14.1 Hz, 1H) 3.69 (s, 3H) 3.64 (d, J=14.4 Hz, 1H) 3.26 (s, 3H). [M-H]

calc'd for $C_{16}H_{15}Cl_2N_4O_2$, 365. found, 365. [M-NH$_2$] calc'd for $C_{16}H_{15}Cl_2N_3O_2$, 348; found, 348.

Example 38

Preparation of 7-Amino-6-(aminomethyl)-5-(2-chloro-5-(trifluoromethyl)phenyl)-1,3-dimethylpyrido[2,3-d]pyimidine-2,4(1H,3H)-dione (Compound 42)

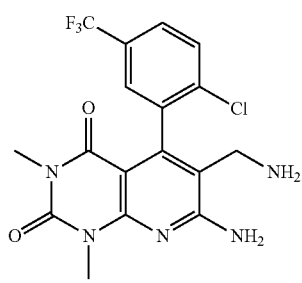

The title compound was prepared using the procedures described in the preparation of Example 11. $^1$H-NMR (400 MHz, d$_6$-DMSO): δ ppm 7.81 (m, 4H), 7.73 (bs, 1H), 7.56 (bs, 2H), 3.82 (d, J=14.4 Hz, 1H), 3.53 (s, 3H), 3.24 (d, J=16.8 Hz, 1H), 3.08 (s, 3H). MS [m+H] calc'd for $C_{17}H_{15}ClF_3N_5O_2$, 414.0, 415.8; found 415.8.

Example 39

Preparation of 7-amino-6-(aminomethyl)-5-(2-chloro-5-fluorophenyl)-1-methylpyrido[2,3-d]pyrimidine-2,4(1H,3H)-dione (Compound 43)

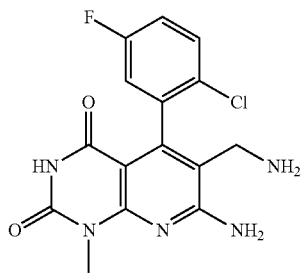

The title compound was prepared using the procedures described in the preparation of Compound 8. $^1$H-NMR (400 MHz, d$_6$-DMSO): δ ppm 11.07 (s, 1H), 7.82 (bs, 3H), 7.57 (dd, J$_1$=5.2, J$_2$=9.2, 1H), 7.51 (bs, 2H), 7.31 (td, J$_1$=8.0, 1H), 7.21 (dd, J$_1$=2.8, J$_2$=8.8, 1H), 3.83 (d, J=22.4, 1H), 3.43 (s, 3H), 3.23 (d, J=20.0, 1H). MS [m+H] calc'd for $C_{15}H_{13}ClFN_5O_2$, 350.1, 352.0; found 350.1, 352.0.

Example 40

Preparation of 7-amino-6-(aminomethyl)-5-(2-bromo-5-fluorophenyl)-1-methylpyrido[2,3-d]pyrimidine-2,4(1H,3H)-dione (Compound 44)

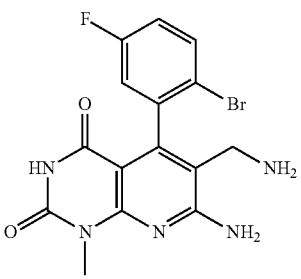

The title compound was prepared using the procedures described in the preparation of Compound 8. $^1$H-NMR (400 MHz, d$_6$-DMSO): δ ppm 11.07 (s, 1H), 7.82 (bs, 3H), 7.70 (dd, J$_1$=5.2, J$_2$=8.8, 1H), 7.50 (bs, 2H), 7.21 (m, 2H), 3.57 (dd, J$_1$=4.8, J$_2$=14.4, 1H), 3.43 (s, 3H), 3.20 (dd, J$_1$=6.0, J$_2$=14.8, 1H). MS [m+H] calc'd for $C_{15}H_{13}BrFN_5O_2$, 395.83, 396.80; found 395.83, 396.80.

Example 41

Preparation of 6-(aminomethyl)-7-(bis(2,2-difluoroethyl)amino)-5-(2-bromo-5-fluorophenyl)-1,3-dimethylpyrido[2,3-d]pyrimidine-2,4(1H,3H)-dione (Compound 45) and 6-(aminomethyl)-5-(2-bromo-5-fluorophenyl)-7-(2,2-difluoroethylamino)-1,3-dimethylpyrido[2,3-d]pyrimidine-2,4(1H,3H)-dione (Compound 46)

45

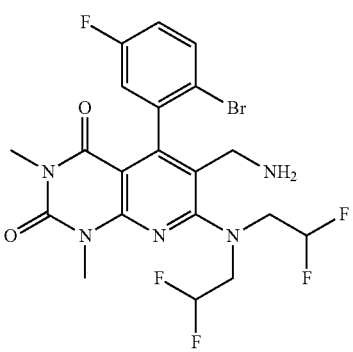

46

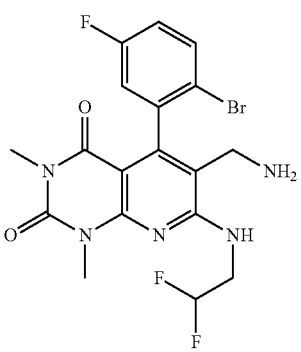

To an amount of 500 mg (1.241 mmole) of Compound 24 (Example 23) was dissolved in 2 ml of anhydrous DMF, was added 134 mg (4.963 mmole) of NaH. The solution was stirred at rt for 10 mins, and then add 2-bromo-1,1-difluoroethane 1.0 g (4.963 mmole), and heated under microwave condition at 120° C. for 4 hrs. The residue was suspended in EtOAc and washed with 10% HCl/H₂O and brine, dried (Na₂SO₄), filtered, then concentrated in vacuo. The resulting mixture was added 1.0 ml of anhydrous THF, cooled to 0° C.-2° C., followed by 4.0 ml (4.0 mmole) of 1M solution of BH₃.THF under nitrogen. It was then added 400 μL of 1N HCl in Dioxane. The mixture was stirred at rt for about 10 min., then heated to 70° C. for 3 hrs. After cooling, to the reaction was added 1N HCl/H₂O until no more bubbling occurred, followed by MeOH, plus a few drops of TFA. The residue was dried in vacuo, purified by HPLC to give the titled compounds.

Compound 45: ¹H NMR (400 MHz, DMSO-d₆) δ ppm 3.13 (s, 3H) 3.35-3.45 (m, 2H) 3.57 (s, 3H) 3.87-4.15 (m, 6H) 7.15 (dd, J=9.09, 2.78 Hz, 1H) 7.30 (td, J=8.27, 3.66 Hz, 1H) 7.79 (dd, J=8.84, 5.31 Hz, 1H) 7.84 (s, 2H). MS [m+H] calc'd for C₂₀H₁₉BrF₅N₅O₂, 536.10, 538.10 and 537.10. found 536.10, 538.10 and 537.10.

Compound 46: ¹H NMR (400 MHz, DMSO-d₆) δ ppm 3.11 (s, 3H) 3.27-3.34 (m, 2H) 3.57 (s, 3H) 3.87-4.03 (m, 3H) 7.22 (dd, J=9.09, 3.03 Hz, 1H) 7.34 (td, J=8.65, 2.91 Hz, 1H) 7.59 (dd, J=8.84, 5.05 Hz, 1H) 7.87 (s, 3H). MS [m+H] calc'd for C₁₈H₁₇ClF₃N₅O₂, 428.0 and 429.9. found 428.0 and 429.9.

Example 42

Preparation 6-(aminomethyl)-5-(2-bromo-5-fluorophenyl)-1,3-dimethyl-7-morpholinopyrido[2,3-d]pyrimidine-2,4(1H,3H)-dione (Compound 47)

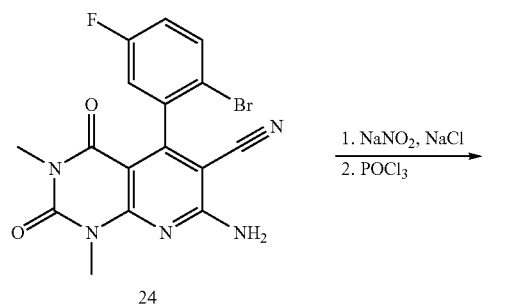

24

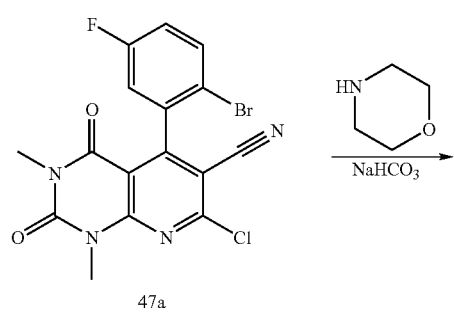

47a

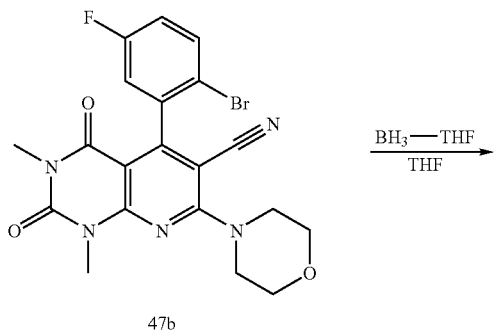

47b

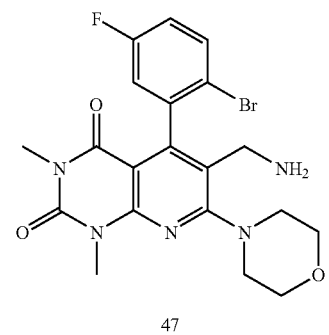

47

An amount of 500 mg (1.241 mmole) of Compound 24 (Example 23) was suspended in 3 mL of AcOH:H₂O/1:3, 363 mg (6.203 mmole) of NaCl, and 428 mg (6.203 mmole) of NaNO₂ which was dissolved in min. amount of H₂O. After stirring at rt overnight, the mixture was extracted with DCM (4×) and saturated NaHCO₃. The organic fractions were collected, dried with Na₂SO₄ and concentrated in vacuo. To the residue was added 4 ml of POCl₃ and 2.6 g (12.41 mmole) of PCl₅. It was heated to 115° C. for 3 hrs and the solvent was evaporated in vacuo. The resulting compound 5-(2-bromo-5-fluorophenyl)-7-chloro-1,3-dimethyl-2,4-dioxo-1,2,3,4-tetrahydropyrido[2,3-d]pyrimidine-6-carbonitrile (47a) was carried onto the next step without future purification. MS [m+H] calc'd for C₁₆H₁₃BrClFN₄O₂, 428.99, and 426.99. found 428.99, and 426.99.

An amount of 50 mg (0.117 mmole) of 47a was dissolved in 500 μL, of MeOH, 1 ml of morpholine and 512 mg (6.203 mmole) of NaHCO₃. The mixture was heated to 80° C. for 1 hr to give 5-(2-Bromo-5-fluoro-phenyl)-1,3-dimethyl-7-morpholin-4-yl-2,4-dioxo-1,2,3,4-tetrahydro-pyrido[2,3-d]pyrimidine-6-carbonitrile (47b).

Crude product 47b was converted to the title compound following the procedure described in the preparation of Compound 11 (Example 10). ¹H NMR (400 MHz, DMSO-d₆) δ ppm 3.13 (s, 3H) 3.36-3.48 (m, 6H) 3.59 (s, 3H) 3.80 (t, J=4.29 Hz, 4H) 7.15 (dd, J=8.8, 2.80 Hz, 1H) 7.30 (td, J=8.72, 3.03 Hz, 1H) 7.76-7.88 (m, 3H). MS [m+H] calc'd for C₂₀H₂₂BrFN₅O₃, 478.0, 479.9, and 481.2. found 478.0, 479.9, and 481.2.

Example 43

Preparation 6-(aminomethyl)-5-(2-bromo-5-fluorophenyl)-1,3-dimethyl-7-((4-methylpiperazin-1-yl)methylamino)pyrido[2,3-d]pyrimidine-2,4(1H,3H)-dione (Compound 48)

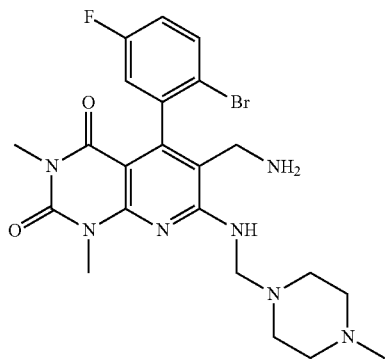

The title compound was prepared using the procedures described in the preparation of Compound 47 (Example 42). $^1$H NMR (400 MHz, MeOD) δ ppm 2.99 (s, 3H) 3.27 (s, 3H) 3.54 (m, 8H) 3.72 (s, 3H) 3.80 (d, J=15.16 Hz, 1H) 4.05 (d, J=15.16 Hz, 1H) 7.07 (d, J=8.34 Hz, 1H) 7.22 (t, J=9.73 Hz, 1H) 7.76 (dd, J=8.84, 5.05 Hz, 1H). MS [m+H] calc'd for $C_{21}H_{24}BrFN_6O_2$, 491.05, 493.00 and 494.17. found 491.05, 493.00 and 494.17.

Example 44

Preparation of 6-(aminomethyl)-5-(2-bromo-5-fluorophenyl)-1,3-dimethyl-7-(pyridine-4-ylmethylamino)pyrido[2,3-d]pyrimidine-2,4(1H,3H)-dione (Compound 49)

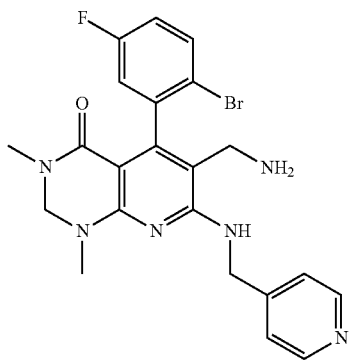

The title compound was prepared using the procedures described in the preparation of Compound 47 (Example 42). $^1$H NMR (400 MHz, DMSO-d$_6$) δ ppm 3.07 (s, 3H) 3.28 (s, 3H) 3.36-3.37 (m, 2H) 4.75-4.87 (m, 2H) 7.21-7.31 (m, 2H) 7.70-7.78 (m, 2H) 7.96 (s, 3H) 8.39 (m, 1H) 8.68 (d, J=5.30 Hz, 2H). MS [m+H] calc'd for $C_{22}H_{20}BrFN_6O_2$, 499.0, 501.0 and 502.1. found 499.0, 501.0 and 502.1.

Example 45

Preparation of 6-(aminomethyl)-5-(2-bromo-5-fluorophenyl)-1,3-dimethyl-7-(cyclopropylamino)-1,3-dimethylpyrido[2,3-d]pyrimidine-2,4(1H,3H)-dione (Compound 50)

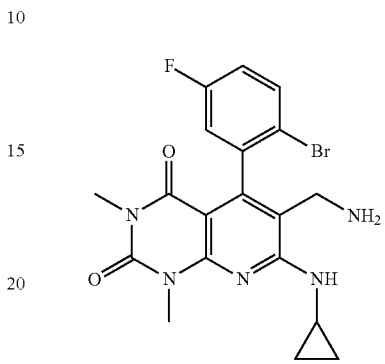

The title compound was prepared using the procedures described in the preparation of Compound 47 (Example 42). $^1$H NMR (400 MHz, DMSO-d$_6$) δ ppm 0.63-0.74 (m, 2H) 0.85 (ddd, J=6.95, 3.66, 3.54 Hz, 2H) 2.93-3.00 (m, J=7.01, 3.44, 3.44, 3.28 Hz, 1H) 3.11 (s, 3H) 3.22 (d, J=14.65 Hz, 1H) 3.61 (s, 3H) 3.91 (d, J=13.89 Hz, 1H) 7.20-7.28 (m, J=9.19, 9.19, 8.91, 3.03 Hz, 2H) 7.71-7.83 (m, 4H). MS [m+H] calc'd for $C_{19}H_{19}BrFN_5O_2$, 448.0, 450.0 and 451.0. found 448.0, 450.0 and 451.0.

Example 46

Preparation of 6-(Aminomethyl)-5-(2,5-dichloro)-1,3-dimethyl-7-morpholinopyrido[2,3-d]pyrimidine-2,4(1H,3H)-dione (Compound 51)

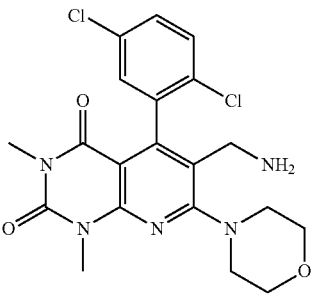

The title compound was made by the procedure described in the preparation of Compound 47 (Example 42). $^1$H NMR (400 MHz, CDCl$_3$:CDOD$_3$ 10:1) δ ppm 7.34 (s, 1H) 7.32 (d, J=2.5 Hz, 1H) 7.10 (d, J=2.3 Hz, 1H) 3.84 (d, J=14.9 Hz, 1H) 3.66 (d, J=14.9 Hz, 1H) 3.59 (s, 3H) 3.37-3.25 (m, 4H), 3.18 (s, 3H). MS [m+H] calc'd for $C_{20}H_{22}Cl_2N_5O_3$, 450.1; Found 450.1.

Example 47

Preparation of 7-amino-6-(aminomethyl)-5-(2,4-dichlorophenyl)-1-methylpyrido[2,3-d]pyrimidine-2,4(1H,3H)-dione (Compound 52)

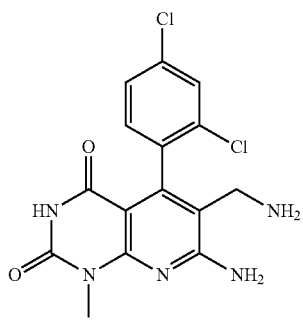

The title compound was prepared using the procedure described in the preparation of Compound 11 (Example 10). $^1$H NMR (400 MHz, CDCl$_3$:CDOD$_3$ 10:1) δ ppm 7.46 (d, J=2.0 Hz, 1H) 7.31 (dd, J=8.1, 2.0 Hz, 1H) 7.03 (d, J=8.3 Hz, 1H) 3.74 (d, J=14.9 Hz, 1H) 3.58 (d, J=14.7 Hz, 1H) 3.50 (s, 3H). MS [m+H] calc'd for C$_{15}$H$_{13}$Cl$_2$N$_5$O$_2$, 366.0; Found 366.0.

Example 48

Preparation of 6-(aminomethyl)-5-(2-bromo-5-fluorophenyl)-7-(diethylamino)-1,3-dimethylpyrido[2,3-d]pyrimidine-2,4(1H,3H)-dione (Compound 53)

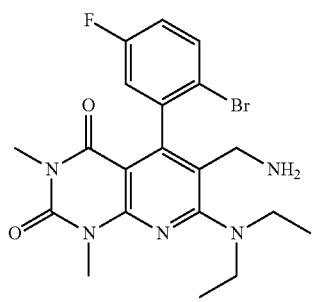

The title compounds were prepared using the procedure described in the syntheses of Compounds 45 and 46 (Example 41). $^1$H NMR (400 MHz, DMSO-d$_6$) δ ppm 1.19 (t, J=7.07 Hz, 6H) 3.11 (s, 3H) 3.44 (d, J=15.23, 1H) 3.54-3.55 (m, 4H) 3.56 (s, 3H) 3.80 (d, J=15.23, 1H) 7.16 (dd, J=9.09, 3.03 Hz, 1H) 7.30 (m, 1H) 7.69 (s, 2H) 7.77 (dd, J=8.72, 5.18 Hz, 1H). MS [m+H] calc'd for C$_{20}$H$_{23}$BrFN$_5$O$_2$, 464.10, 466.10 and 467.10. found 464.10, 466.10 and 467.10.

Example 49

Preparation of 6-(aminomethyl)-5-(2-bromo-5-fluorophenyl)-7-(ethylamino)-1,3-dimethylpyrido[2,3-d]pyrimidine-2,4(1H,3H)-dione (Compound 54)

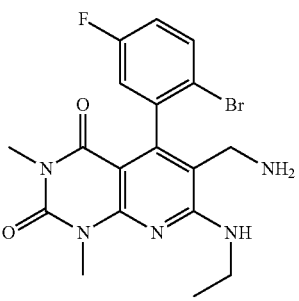

The title compounds were prepared using the procedure described in the syntheses of Compounds 45 and 46 (Example 41). $^1$H NMR (400 MHz, DMSO-d$_6$) δ ppm 1.288 (t, J=6.8, 3H) 2.49 (s, 3H) 3.23 (d, J=12.8, 1H) 3.53 (m, 2H) 3.26 (s, 3H) 3.90 (d, J=12.8, 1H) 7.24 (m, 1H) 7.60 (m, 1H) 7.72 (m, 1H) 7.81 (s, 2H). MS [m+H] calc'd for C$_{18}$H$_{19}$BrFN$_5$O$_2$, 436.1, 437.1 and 438.1. found 436.1, 437.1 and 438.1.

Example 50

Preparation of 6-(aminomethyl)-5-(2-bromo-5-fluorophenyl)-1,3-dimethyl-7-(methylamino)pyrido[2,3-d]pyrimidine-2,4(1H,3H)-dione (Compound 55)

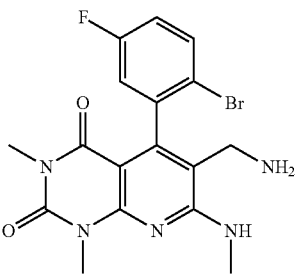

The title compounds were prepared using the procedure described in the syntheses of Compounds 45 and 46 (Example 41). $^1$H NMR (400 MHz, DMSO-d$_6$) δ ppm 3.03 (d, J=3.79 Hz, 3H) 3.10 (s, 3H) 3.25 (d, J=14.65 Hz, 1H) 3.59 (s, 3H) 3.88 (d, J=14.40 Hz, 1H) 7.18-7.28 (m, 2H) 7.67 (s, 2H) 7.73 (dd, J=8.72, 5.18 Hz, 1H). MS [m+H] calc'd for C$_{17}$H$_{17}$BrFN$_5$O$_2$, 422.1, 423.1 and 425.1. found 422.1, 423.1 and 425.1.

Example 51

Preparation of 6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione (Compound 56)

Compound 56 was prepared according to the scheme below:

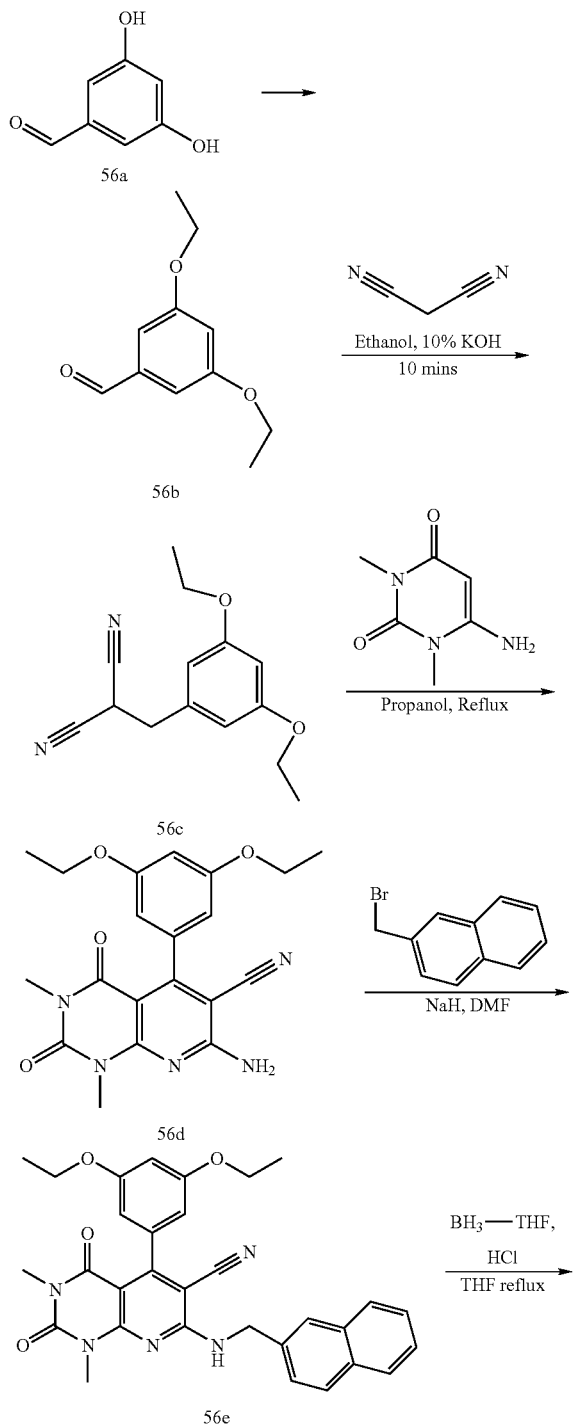

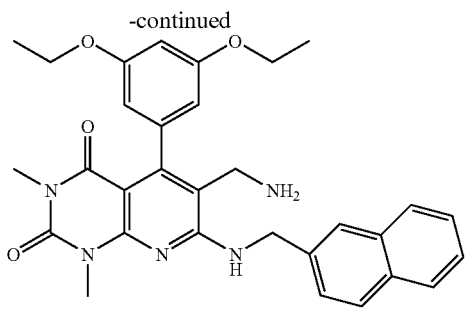

56

A.

An amount of 3,5-dihydroxybenzaldehyde (56a, 500 mg, 3.62 mmol) was dissolved in 10 mL DMF, anhydrous. It was added (2.0 g, 18.1 mmol) of bromoethane and 733 mg (5.34 mmol) of $K_2CO_3$. The reaction mixture was heated to 60° C. for 4-5 hrs. Afterwards, 100 mL of EtoAce was added to the reaction mixture, and the reaction mixture was washed with brine (3×200 mL). The organic layer was dried over $Na_2SO_4$ and evaporated in vacuuo to afford 3,5-diethoxybenzaldehyde (56b) which was carried onto the next step without further purification. MS [m+H] calc'd for $C_{11}H_{14}O_3$, 195.10; found 195.10.

B.

To an amount of 56c (1.0 g, 5.15 mmole) of 3,5-diethoxybenzaldehyde dissolved in 10 mL of propanol, was added malononitrile (375 mg, 5.67 mmole) and 2 drops of sat. KOH. The mixture was stirred at r.t. for 10 mins. Precipitates was filtered to yield 1.0 g of 2-(3,5-diethoxybenzylidene)malononitrile (56d). MS [m+H] calc'd for $C_{14}H_{14}N_2O_2$, 243.11; found 243.11.

C.

An amount of 56c (1.0 g, 4.13 mmole) and 6-amino1,3-dimethyluracil (961 mg, 6.19 mmol) was suspended in 20 mL of propanol. The solution was refluxed at 120° C. overnight. After evaporation in vacuuo, the residue was dissolved in EtoAce (200 mL) and washed 3 times with 1N HCl solution. The organic layer was dried over $Na_2SO_4$ and evaporated in vacuuo. The residue was suspended in ether and solid was filtered to give 7-amino-5-(3,5-diethoxyphenyl)-1,3-dimethyl-2,4-dioxo-1,2,3,4-tetrahydropyrido[2,3-d]pyrimidine-6-carbonitrile (56d, 816 mg). MS [m+H] calc'd $C_{20}H_{21}N_5O_4$, 396.16; found 396.16.

D.

A solution of 56d (100 mg, 0.25 mmol) in DMF (3 mL) was treated with 60% NaH (12 mg, 0.3 mmol). After the mixture was vigorously stirred for 30 min, a solution of 2-(bromomethyl)naphthalene (55 mg, 0.25 mmol) was added. The mixture was stirred at rt for 20 min, and 50° C. for 2 h. After which the solution was suspended in 200 mL of EtoAce and was washed with brine, 3×200 mL. The organic layer was dried over $Na_2SO_4$ and evaporated in vacuuo. The residue was purified by prep HPLC to give 5-(3,5-diethoxyphenyl)-1,3-dimethyl-7-(naphthalene-2-ylmethylamino)-2,4-dioxo-1,2,3,4-tetrahydropyrido[2,3-d]pyrimidine-6-carbonitrile (56e, 87 mg). MS [m+H] calc'd for $C_{31}H_{29}N_5O_4$, 536.22; found 536.22

E.

An amount of 56e (87 mg, 0.163 mmol) was dissolved in 0.5 mL THF. It was added 2 mL (2 mmol) of 1M $BH_3$.THF. The mixture was heated under refluxing condition for 15 min, and then evaporated and co-evaporated with MeOH, further treated with TFA-MeOH (1:4, 4 mL) at 60° C. for 20 min. The mixture was purified by LC-MS to give Compound 56.

1H NMR (400 MHz, MeOD) δ ppm 1.24 (t, J=7.20 Hz, 3H) 1.37 (t, J=6.95 Hz, 3H) 3.18 (s, 3H) 3.51 (s, 3H) 3.91 (s, 2H) 3.96-4.17 (m, 4H) 4.98 (s, 2H) 6.33 (d, J=2.27 Hz, 2H) 6.53 (t, J=2.15 Hz, 1H) 7.39-7.49 (m, 2H) 7.57 (dd, J=8.34, 1.77 Hz, 1H) 7.76-7.92 (m, 4H). MS [m+H] calc'd $C_{31}H_{33}N_5O_4$ 540.3; found 540.3.

Example 52

Preparation of 6-(aminomethyl)-5-(3,5-dimethoxyphenyl)-1,3-dimethyl-7-(naphthalen-2-ylmethylamino)pyrido[2,3-d]pyrimidine-2,4(1H,3H)-dione (Compound 57)

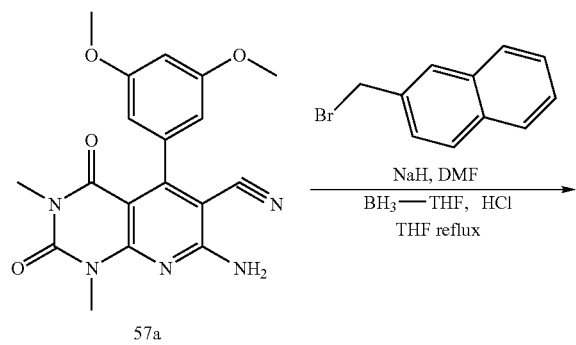

51A was prepared from 3,5-dimethoxybenzaldehyde and 6-amino-1,3-dimethylpyrimidine-2,4(1H,3H)-dione, according to the procedures described in the synthesis of Compound 56. 1H NMR (400 MHz, DMSO-d6) □ ppm 3.06 (s, 3H) 3.44 (s, 3H) 3.73 (s, 6H) 4.87 (s, 2H) 6.34 (s, 2H) 7.48 (br. s., 2H) 7.79-7.93 (m, 6H) 7.64 (br. s., 2H) MS [m+H] MS [m+H] calc'd C29H29N5O4 512.3: found 512.3.

The titled compound 56 was prepared from 57A and 2-(bromomethyl)naphthalene, according to procedures described in the synthesis of Compound 56 (Example 51). $^1$H NMR (400 MHz, DMSO-d$_6$) δ ppm 3.06 (s, 3H) 3.44 (s, 3H) 3.73 (s, 6H) 4.87 (s, 2H) 6.34 (s, 2H) 7.48 (br. s., 2H) 7.79- 7.93 (m, 6H) 7.64 (br. s., 2H) MS [m+H] MS [m+H] calc'd $C_{29}H_{29}N_5O_4$ 512.3: found 512.3

Example 53

Preparation of 3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide (Compound 58)

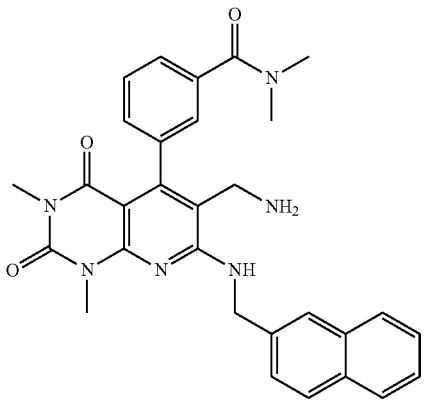

The title compound was prepared from 3-formyl-N-methylbenzamide and 6-amino-1,3-dimethylpyrimidine-2,4(1H, 3H)-dione, according to the procedures described in the synthesis of Compound 56. 1H NMR (400 MHz, DMSO-d$_6$) δ ppm 2.42 (s, 3H) 2.72 (s, 3H) 3.03 (s, 3H) 3.45 (s, 3H) 4.90 (s, 2H) 7.19-7.30 (m, 2H) 7.41-7.54 (m, 3H) 7.54-7.69 (m, 3H) 7.76-7.85 (m, 3H) 7.85-8.00 (m, 3H) MS [m+H] calc'd $C_{30}H_{30}N_6O_3$ 523.3; found 523.3

Example 54

Preparation of 6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione (Compound 59)

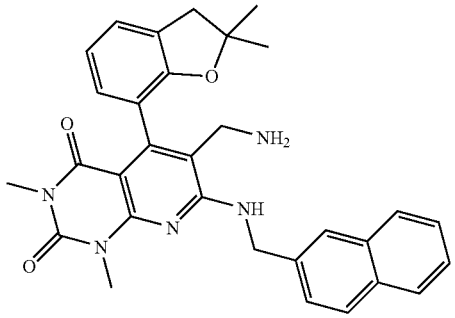

The synthesis of title compounds started from 2,2-dimethyl-2,3-dihydrobenzofuran-7-carbaldehyde and 6-amino-1,3-dimethylpyrimidine-2,4(1H,3H)-dione, according to the procedures described in the synthesis of Compound 56.

1H NMR (400 MHz, MeOD) δ ppm 1.35 (s, 3H) 1.42 (s, 3H) 3.08 (s, 2H) 3.15 (s, 3H) 3.49 (s, 3H) 3.53 (d, J=4.80 Hz, 2H) 4.94 (d, J=6.82 Hz, 2H) 6.80-6.94 (m, 2H) 6.80-6.94 (m,

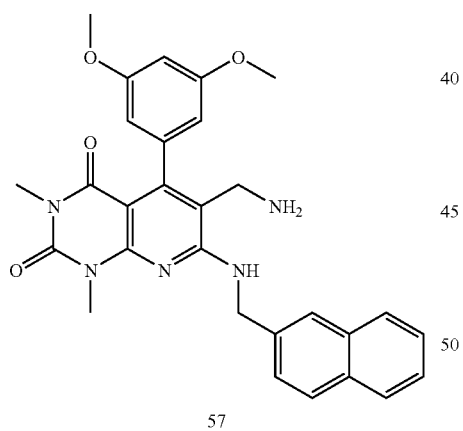

1H) 7.35-7.48 (m, 2H) 7.35-7.48 (m, 1H) 7.78-7.93 (m, 8H) 7.78-7.93 (m, 4H) MS [m+H] calc'd for $C_{31}H_{32}N_5O_3$ 522.5; found 522.5

Example 55

Preparation of 6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione (Compound 60)

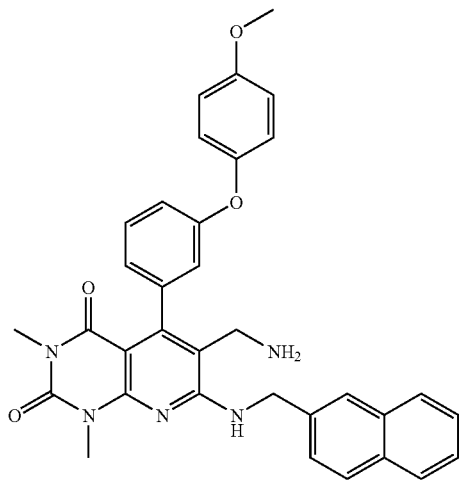

The synthesis of title compounds started from 3-(4-methoxyphenoxy)benzaldehyde and 6-amino-1,3-dimethylpyrimidine-2,4(1H,3H)-dione, according to the procedures described in the synthesis of Compound 56.

1H NMR (400 MHz, MeOD) δ ppm 3.16 (s, 3H) 3.47 (s, 9H) 3.75 (s, 3H) 3.84-3.96 (m, 1H) 3.84-3.96 (m, 2H) 4.95 (s, 3H) 6.81-7.03 (m, 7H) 7.33-7.48 (m, 3H) 7.41 (d, J=6.82 Hz, 7H) 7.48-7.67 (m, 2H) 7.76-7.91 (m, 5H) MS [m+H] MS [m+H] calc'd $C_{34}H_{31}N_5O_4$ 574.4; found 574.4.

Example 56

Preparation of 6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione (Compound 61)

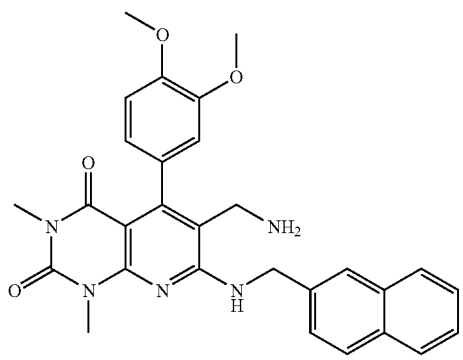

The synthesis of title compounds started from 3,4-dimethoxybenzaldehyde and 6-amino-1,3-dimethylpyrimidine-2,4(1H,3H)-dione, according to the procedures described in the synthesis of Compound 56.

1H NMR (400 MHz, MeOD) δ ppm 3.16 (s, 3H) 3.51 (s, 3H) 3.82 (s, 2H) 3.81 (s, 3H) 3.92 (d, J=9.85 Hz, 2H) 3.89 (s, 3H) 6.71 (dd, J=8.21, 1.89 Hz, 1H) 6.79 (d, J=1.77 Hz, 1H) 7.05 (d, J=8.34 Hz, 1H) 7.58 (d, J=3.79 Hz, 1H) 7.41-7.52 (m, 2H) 7.80-7.87 (m, 3H) 7.89 (s, 1H) MS [m+H] calc'd $C_{29}H_{29}N_5O_4$ 512.3; found 512.3.

Example 57

Preparation of 6-(Aminomethyl)-5-(benzo[d]thiazol-2-yl)-1,3-dimethyl-7-(naphthalen-2 ylmethylamino)pyrido[2,3-d]pyrimidine-2,4(1H,3H)-dione (Compound 62)

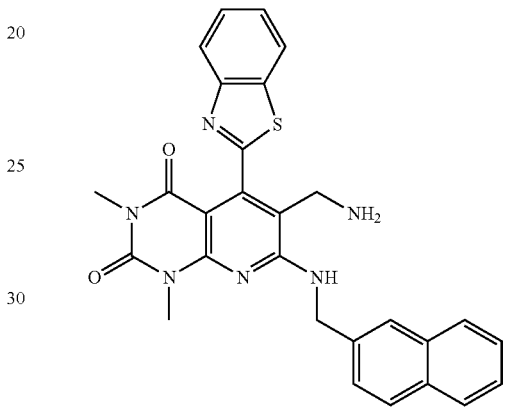

The synthesis of title compounds started from benzo[d]thiazole-2-carbaldehyde and 6-amino-1,3-dimethylpyrimidine-2,4(1H,3H)-dione, according to the procedures described in the synthesis of Compound 56.

1H NMR (400 MHz, MeOD) δ ppm 3.18 (s, 3H) 3.53 (s, 3H) 3.86 (s, 2H) 5.00 (s, 2H) 7.47 (d, J=1.77 Hz, 2H) 7.58 (ddd, J=14.34, 9.41, 4.80 Hz, 2H) 7.82 (dd, J=5.31, 2.27 Hz, 2H) 7.93 (br. s., 2H) 8.00 (d, J=7.83 Hz, 1H) 8.14 (d, J=8.84 Hz, 1H) 8.08 (d, J=8.59 Hz, 1H). MS [m+H] calc'd $C_{29}H_{29}N_5O_4$ 509.2; found 509.2.

Example 58

Preparation of 6-(Aminomethyl)-1,3-dimethyl-7-(naphthalen-2-ylmethylamino)-5-(2-phenoxyphenyl)pyrido[2,3-d]pyrimidine-2,4(1H,3H)-dione (Compound 63)

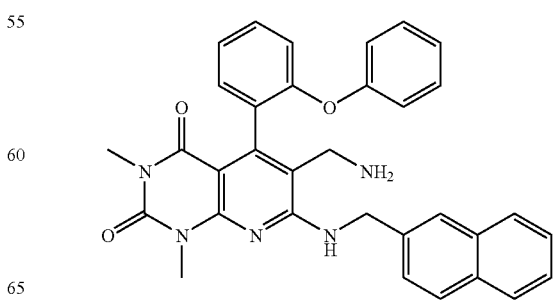

The synthesis of title compounds started from 2-phenoxybenzaldehyde and 6-amino-1,3-dimethylpyrimidine-2,4(1H,3H)-dione, according to the procedures described in the synthesis of Compound 56.

1H NMR (400 MHz, MeOD) δ ppm 3.15 (s, 3H) 3.34 (s, 2H) 3.44 (s, 3H) 4.97 (d, 2H) 6.86 (d, J=9.60 Hz, 2H) 6.94 (t, 1H) 7.04 (d, J=8.59 Hz, 1H) 7.22-7.29 (m, 2H) 7.24 (d, J=2.27 Hz, 2H) 7.40-7.47 (m, 4H) 7.82 (br. s., 4H). MS [m+H] calc'd $C_{33}H_{29}N_5O_3$ 512.3 544.3; found 544.3.

Example 59

Preparation of 6-(aminomethyl)-5-(2,5-diethoxyphenyl)-1,3-dimethyl-7-(naphthalen-2-ylmethyl amino)pyrido[2,3-d]pyrimidine-2,4(1H,3H)-dione (Compound 64)

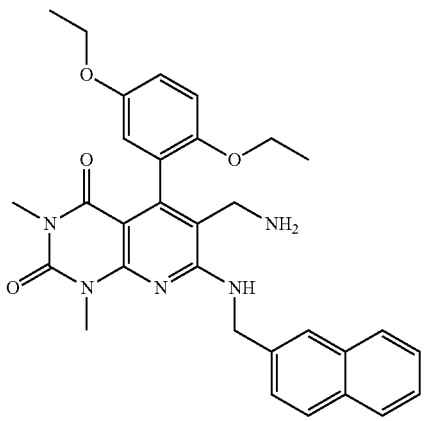

The synthesis of title compounds started from 2,5-diethoxybenzaldehyde and 6-amino-1,3-dimethylpyrimidine-2,4(1H,3H)-dione, according to the procedures described in the synthesis of Compound 56. 1H NMR (400 MHz, MeOD) δ ppm 1.09-1.22 (m, 6H) 3.18 (s, 3H) 3.52 (s, 3H) 3.83-4.08 (m, 6H) 4.98 (d, J=30.57 Hz, 2H) 6.63 (d, J=3.03 Hz, 1H) 6.97 (dd, J=8.84, 3.03 Hz, 1H) 7.05-7.12 (m, 1H) 7.40-7.51 (m, 2H) 7.59 (dd, J=8.72, 1.39 Hz, 1H) 7.78-7.88 (m, 3H) 7.89 (s, 1H). MS [m+H] calc'd $C_{31}H_{33}N_5O_4$ 540.3; found 540.3

Example 60

Preparation of 6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione (Compound 65)

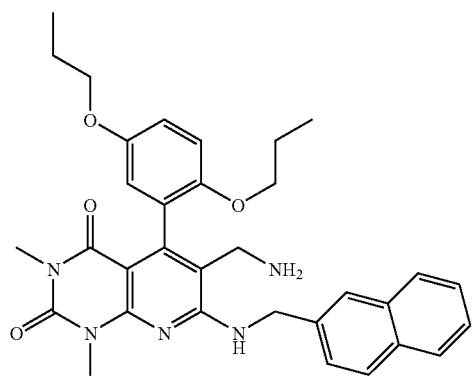

The synthesis of title compounds started from 2,5-dipropyloxybenzaldehyde and 6-amino-1,3-dimethylpyrimidine-2,4(1H,3H)-dione, according to the procedures described in the synthesis of Compound 56. 1H NMR (400 MHz, MeOD) δ ppm 0.73 (t, J=7.33 Hz, 3H) 1.02 (t, J=7.33 Hz, 3H) 1.48-1.59 (m, 2H) 1.70-1.83 (m, 2H) 3.18 (s, 3H) 3.34 (s, 3H) 3.52 (s, 3H) 3.89 (s, 2H) 4.99 (d, J=7.07 Hz, 2H) 6.66 (d, J=3.03 Hz, 1H) 6.98 (dd, J=8.97, 2.91 Hz, 1H) 7.03-7.10 (m, 1H) 7.42-7.50 (m, 2H) 7.57 (d, J=8.59 Hz, 1H) 7.77-7.92 (m, 4H). MS [m+H] calc'd $C_{33}H_{37}N_5O_4$ 568.3; found 567.3.

Example 61

Preparation of 7-Amino-6-(aminomethyl)-5-(4-(aminomethyl)phenyl)-1,3-dimethylpyrido[2,3-d]pyrimidine-2,4(1H,3H)-dione (Compound 66)

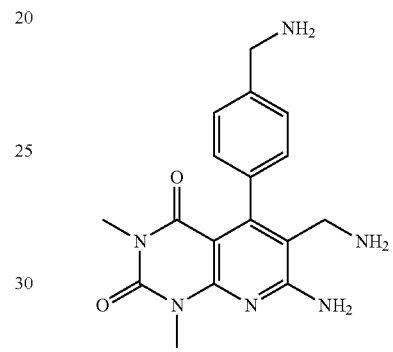

The synthesis of title compounds started from 4-formylbenzonitrile and 6-amino-1,3-dimethylpyrimidine-2,4(1H,3H)-dione, according to the procedures described in the synthesis of Compound 56. 1H NMR (400 MHz, DMSO-$d_6$) δ ppm 3.06 (s, 3H) 3.53 (s, 3H) 3.56 (d, J=5.56 Hz, 2H) 4.12 (d, J=5.56 Hz, 2H) 7.22 (d, J=7.83 Hz, 2H) 7.49 (m, 4H) 7.92 (br. s., 2H) 8.37 (br. s., 2H) MS [m+H] MS [m+H] calc'd $C_{17}H_{20}N_6O_2$ 341.38; found 341.4.

Example 62

Preparation of 6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione (Compound 67)

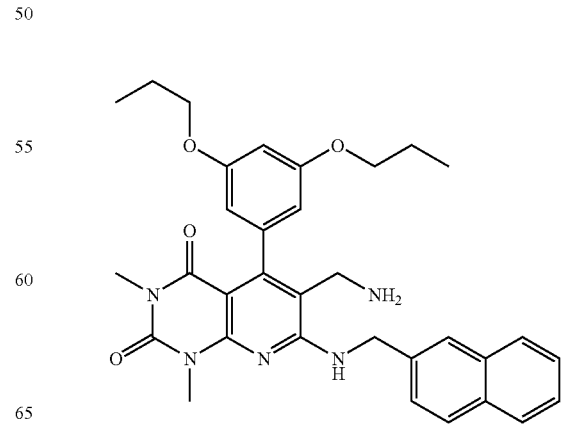

The synthesis of title compounds started from 3,5-dipropyloxybenzaldehyde and 6-amino-1,3-dimethylpyrimidine-2,4(1H,3H)-dione, according to the procedures described in the synthesis of Compound 56. 1H NMR (400 MHz, MeOD) δ ppm 1.03 (t, J=7.45 Hz, 6H) 1.78 (q, J=6.57 Hz, 4H) 3.17 (s, 3H) 3.50 (s, 3H) 3.88-3.97 (m, 6H) 4.97 (s, 2H) 6.34 (d, J=2.27 Hz, 2H) 6.53 (t, J=2.15 Hz, 1H) 7.40-7.49 (m, 2H) 7.57 (dd, J=8.46, 1.64 Hz, 1H) 7.77-7.86 (m, 3H) 7.88 (s, 1H) MS [m+H] calc'd $C_{33}H_{38}N_5O_4$ 568.4; found 568.4.

Example 63

Preparation of N-(4-(6-(aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide (Compound 68) and 6-(aminomethyl)-5-(2-bromo-5-fluorophenyl)-7-(4-(ethylamino)phenylthio)-1,3-dimethylpyrido[2,3-d]pyrimidine-2,4(1H,3H)-dione (Compound 69)

Compounds 68 and 69 were synthesize according to the following scheme

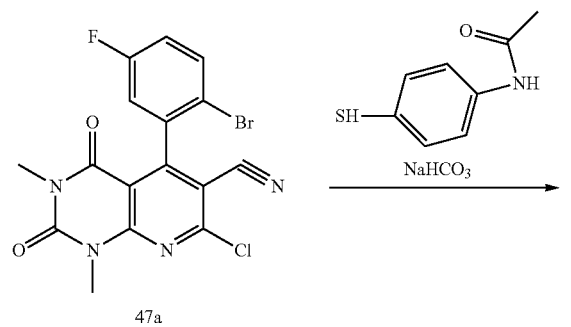

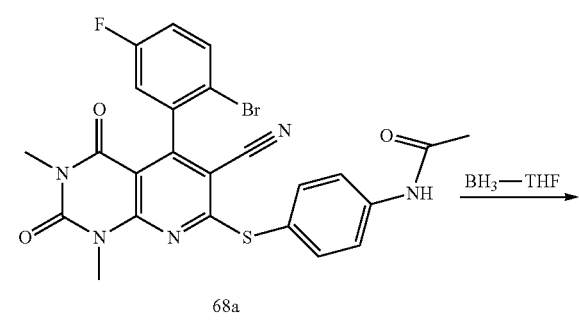

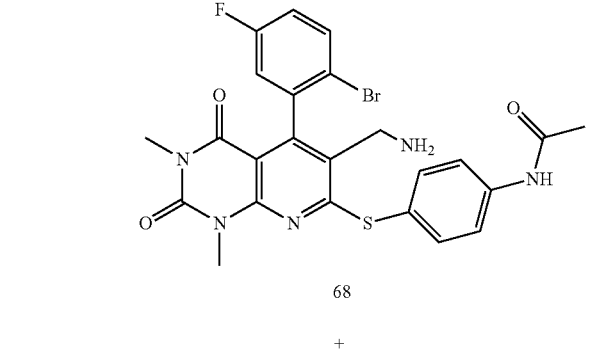

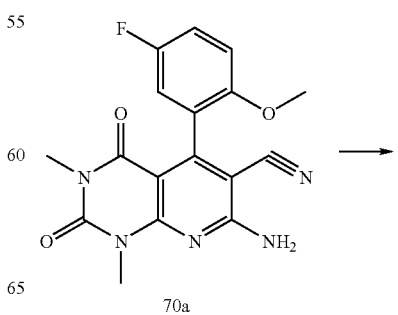

A mixture of 47a (Example 42, 100 mg, 0.24 mmol), N-(4-mercaptophenyl)acetamide (50 mg, 0.3 mmol) and NaHCO$_3$ (100 mg) in dry isopropanol (1 mL) was heated at 100° C. for 30 min to yield a crude product of N-(4-(5-(2-bromo-5-fluorophenyl)-6-cyano-1,3-dimethyl-2,4-dioxo-1,2,3,4-tetrahydropyrido[2,3-d]pyrimidin-57-ylthio)phenyl)acetamide (68a). After workup, 68a was dried and treated with 1M BH$_3$-THF (2 mL) in THF under refluxing condition for 10 min. evaporated and co-evaporated with MeOH. The mixture was treated with 10% TAF in MeOH at 60° C. for 10 min.; the mixture was purified with LC-MS to give Compound 68 and Compound 69.

Compound 68: 1H NMR (400 MHz, CHLOROFORM-d) δ ppm 1.14 (t, J=7.1 Hz, 3H) 3.12 (s, 3H) 3.20 (s, 3H) 3.43 (q, J=7.1 Hz, 2H) 3.70 (d, J=14.7 Hz, 1H) 4.01 (d, J=14.7 Hz, 1H) 7.05 (td, J=8.3, 3.0 Hz, 1H) 6.98 (dd, J=8.3, 3.0 Hz, 1H) 7.49 (d, J=8.6 Hz, 2H) 7.61 (dd, J=8.8, 5.1 Hz, 1H) 7.66 (d, J=8.6 Hz, 2H). MS [m+H] calc'd $C_{24}H_{22}BrFN_5O_3S$ 558. found 558.

Compound 69: 1H NMR (400 MHz, CHLOROFORM-d) δ ppm 1.14 (t, J=7.1 Hz, 3H) 3.12 (s, 3H) 3.20 (s, 3H) 3.43 (q, J=7.1 Hz, 2H) 3.70 (d, J=14.7 Hz, 1H) 4.01 (d, J=14.7 Hz, 1H) 7.05 (td, J=8.3, 3.0 Hz, 1H) 6.98 (dd, J=8.3, 3.0 Hz, 1H) 7.49 (d, J=8.6 Hz, 2H) 7.61 (dd, J=8.8, 5.1 Hz, 1H) 7.66 (d, J=8.6 Hz, 2H). MS [m+H] calc'd $C_{24}H_{22}BrFN_5O_3S$ 558. found 558.

Example 64

Preparation of 6-(aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione (Compound 70)

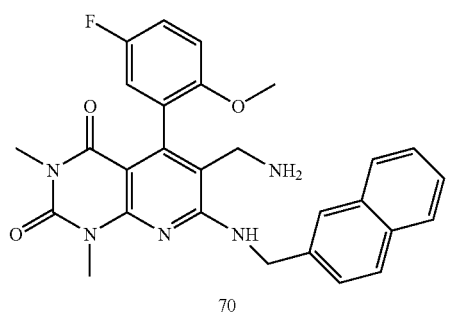

70

7-amino-5-(5-fluoro-2-methoxyphenyl)-1,3-dimethyl-2,4-dioxo-1,2,3,4-tetrahydropyrido[2,3-d]pyrimidine-6-carbonitrile (70a) was prepared by the reaction of 5-fluoro-2-methoxybenzaldehyde and 6-amino-1,3-dimethylpyrimidine-2,4(1H,3H)-dione, according to procedures described in the synthesis of Compound 56. MS [m+H] calc'd $C_{17}H_{15}FN_5O_3$ 356; found 356.

Compound 70 was prepared from 70a and 2-(bromomethyl)naphthalene, according to procedures described in the synthesis of Compound 56. $^1$H NMR (400 MHz, CHLOROFORM-d) δ ppm 3.21 (s, 3H) 3.54 (s, 3H) 3.67 (s, 3H) 4.69 (d, J=14.7 Hz 1H) 4.92 (d, J=14.7 Hz, 1H) 6.64 (dd, J=8.2, 2.9 Hz, 1H) 6.98 dd, J=4.3, 9.1 Hz, 1H) 7.03-7.11 (m, 1H) 7.37-7.42 (m, 1H) 7.44-7.50 (m, 1H) 7.69-7.86 (m, 5H). MS [m+H] calc'd $C_{28}H_{27}FN_5O_3$ 450; found 450.

Example 65

Preparation of 6-(aminomethyl)-5-(5-fluoro-2-methoxyphenyl)-7-(3-methoxybenzylamino)-1,3-dimethylpyrido[2,3-d]pyrimidine-2,4(1H,3H)-dione (Compound 71)

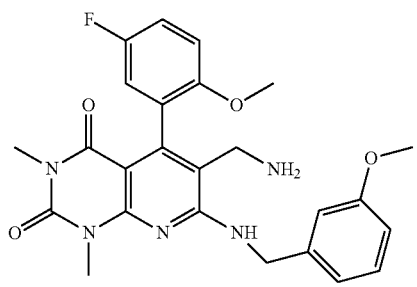

The synthesis of title compounds started from Compound 70a and 1-(bromomethyl)-3-methoxybenzene, according to procedures described in the synthesis of Compound 56. MS [m+H] calc'd $C_{25}H_{27}FN_5O_4$ 480; found 480.

Example 66

Preparation of 7-(4-(1H-pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione (Compound 72)

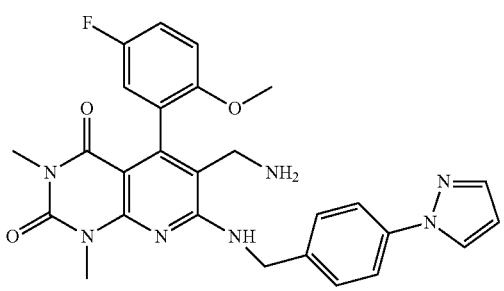

The synthesis of title compounds started from Compound 70a and 1-(4-(bromomethyl)phenyl)-1H-pyrazole, according to procedures described in the synthesis of Compound 56. MS [m+H] calc'd $C_{27}H_{27}FN_7O_3$ 516; found 516.

Example 67

Preparation of 6-(aminomethyl)-5-(5-fluoro-2-methoxyphenyl)-1,3-dimethyl-7-(pentan-3-ylamino)pyrido[2,3-d]pyrimidine-2,4(1H,3H)-dione (Compound 73)

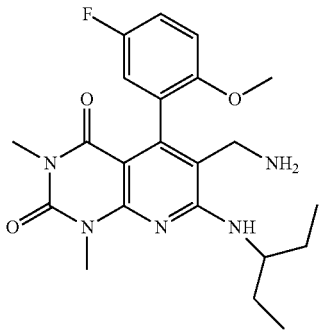

The title compound was prepared from Compound 47a (Example 42, 1 equiv), pentan-3-amine (3 equiv) and NaHCO$_3$ (5 equiv) in isopropanol under micro wave condition at 180° C. for 30 min, and purified by LC-MS. MS [m+H] calc'd $C_{22}H_{29}FN_5O_3$ 430; found 430.

Example 68

Preparation of 6-(aminomethyl)-7-(1,2-diphenylethylamino)-5-(5-fluoro-2-methoxyphenyl)-1,3-dimethylpyrido[2,3-d]pyrimidine-2,4(1H,3H)-dione (Compound 74)

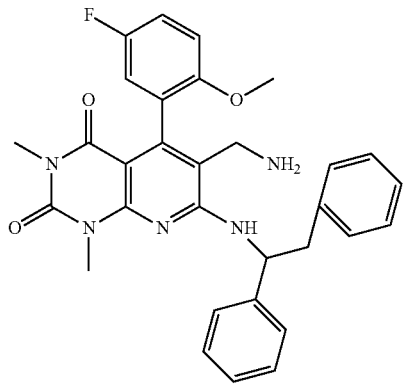

The title compound was prepared from Compound 47a (Example 42) and 1,2-diphenylethanamine, according to procedure described in the synthesis of Compound 47. MS [m+H] calc'd $C_{32}H_{31}FN_5O_3$ 540; found 540.

Example 69

Preparation of 6-(aminomethyl)-5-(5-fluoro-2-methoxyphenyl)-1,3-dimethyl-7-(3-phenylpropylamino) pyrido[2,3-d]pyrimidine-2,4(1H,3H)-dione (Compound 75)

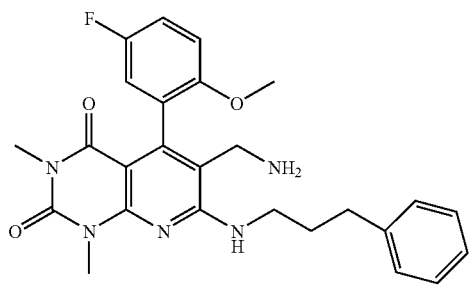

The synthesis of title compounds started from Compound 70a and (3-bromopropyl)benzene, according to procedures described in the synthesis of Compound 70. $^1$H NMR (400 MHz, CHLOROFORM-d) δ ppm 2.41-2.53 (m, 2H) 3.16 (m, 2H) 3.68 (s, 3H) 3.77-3.83 (m, 2H) 3.96 (s, 3H) 4.16 (s, 3H) 4.20 (d, J=14.4 Hz, 1H) 7.71 (d, J=5.6 Hz, 1H) 7.14-7.21 (m, 1H) 7.42-7.48 (dd J=8.8, 4.3 Hz 1H) 7.61-7.65 (m, 3H) 7.69-7.74 (m, 2H). MS [m+H] calc'd $C_{26}H_{29}FN_5O_3$ 478; found 478.

Example 70

Preparation of 7-amino-6-(aminomethyl)-5-(3-isobutoxyphenyl)-1,3-dimethylpyrido[2,3-d]pyrimidine-2,4(1H,3H)-dione (Compound 76)

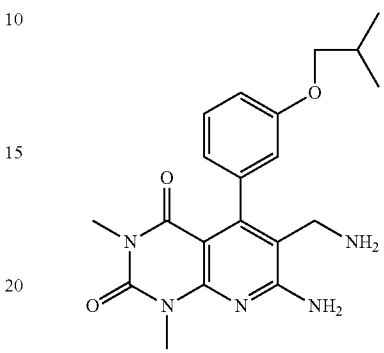

The syntheses of Compound 76 started from 3-isobutoxybenzaldehyde and 6-amino-1,3-dimethylpyrimidine-2,4(1H,3H)-dione, according to procedures described in the synthesis of Compound 56. 1H NMR (400 MHz, CHLOROFORM-d) δ ppm 0.94 (d, J=6.6 Hz, 12H) 1.90-2.07 (m, 1H) 2.57 (s, 3H) 3.19 (s, 3H) 3.56 (s, 3H) 3.66 (d, J=6.3 Hz, 2H) 3.70 (s, 3H) 5.24 (s, 7H) 6.58 (t, 1H) 6.63 (bd, J=8.1 Hz, 1H) 6.90 (dd, J=7.6, 2.5 Hz, 1H) 7.32 (t, J=7.8 Hz, 1H). MS [m+H] calc'd $C_{20}H_{26}FN_5O_3$ 384; found 384

Example 71

Preparation of 6-(aminomethyl)-5-(2-isobutoxyphenyl)-1,3-dimethyl-7-(naphthalen-2-ylmethylamino) pyrido[2,3-d]pyrimidine-2,4(1H,3H)-dione (Compound 77)

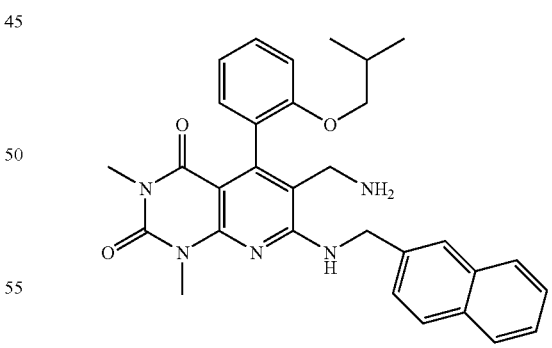

The syntheses of Compound 77 started from 2-isobutoxybenzaldehyde and 6-amino-1,3-dimethylpyrimidine-2,4(1H, 3H)-dione, according to procedures described in the synthesis of Compound 56. 1H NMR (400 MHz, CHLOROFORM-d) δ ppm 0.68, 0.70 (d, J=6.8 Hz, 3H each) 1.72-1.86 (m, 1H) 3.18 (s, 3H) 3.53 (s, 3H) 3.59 (dd, J=9.1, 6.8 Hz, 1H) 3.68-3.79 (m, 2H) 3.87 (d, J=14.4 Hz 1H) 4.80 (d, J=14.9 Hz 1H) 4.93 (d, J=14.7 Hz, 1H) 6.91-6.96 (m, 2H) 7.33 (dd, J=8.8, 2.5

Hz, 1H) 7.37-7.45 (m, 3H) 7.48 (dd, J=8.3, 1.5 Hz, 1H) 7.71-7.83 (m, 4H). MS [m+H] calc'd $C_{31}H_{34}FN_5O_3$ 524; found 524.

Example 72

Preparation of 6-(aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione (Compound 78)

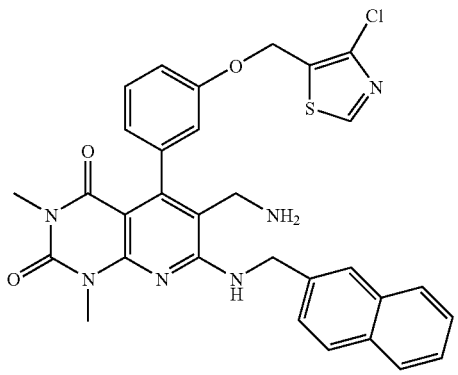

The synthesis of Example 78 started from 3-((4-chlorothiazol-5-yl)methoxy)benzaldehyde and 6-amino-1,3-dimethylpyrimidine-2,4(1H,3H)-dione, according to procedures described in the synthesis of Compound 56. 1H NMR (400 MHz, CHLOROFORM-d) δ ppm 3.18 (s, 3H) 3.34 (m., 2H) 3.53 (s, 3H) 3.75 (d, J=2.02 Hz, 2H) 4.85 (s, 1H) 5.12 (s, 1H) 6.68 (dd, J=2.4, 1.4 Hz, 1H) 6.73 (d, J=7.6 Hz, 2H) 6.97 (dd, J=8.6, 2.8 Hz, 1H) 7.33-7.46 (m, 3H) 7.46-7.53 (m, 1H), 7.73-7.79 (m, 4H). MS [m+H] calc'd $C_{31}H_{28}ClN_6O_3S$ 599. found 599.

Example 73

Preparation of 6-(aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione (Compound 79)

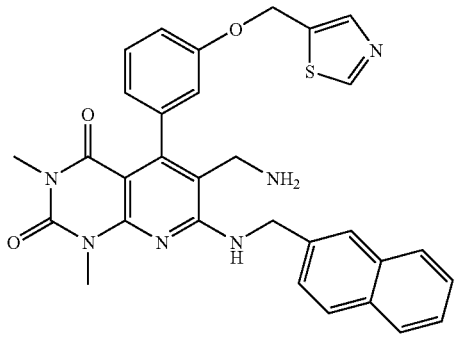

Example 79 was isolated as a side product during the synthesis of Compound 78. 1H NMR (400 MHz, CHLOROFORM-d) δ ppm 2.51 (s, 1H) 3.08 (s, 3H) 3.25 (s, 2H) 3.43 (s, 3H) 3.68 (q, J=14.6 2H) 4.77 (s, 2H) 5.16 (s, 2H) 5.19 (s, 1H) 6.59-6.68 (m, 2H) 6.91 (dd, J=8.2, 1.9 Hz, 1H) 7.26-7.36 (m, 3H) 7.40 (dd, J=8.5, 1.6 Hz, 1H) 7.61-7.72 (m, 4H) 7.76 (br. s., 1H) 8.75 (br. s., 1H). MS [m+H] calc'd $C_{31}H_{29}N_6O_3S$ 565. found 565.

Example 74

Preparation of 6-(aminomethyl)-5-(3-hydroxyphenyl)-1,3-dimethyl-7-(naphthalen-2-ylmethylamino)pyrido[2,3-d]pyrimidine-2,4(1H,3H)-dione (Compound 80)

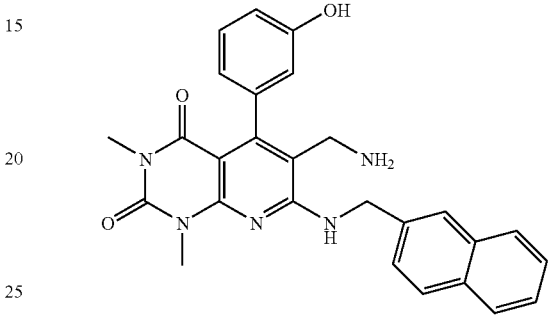

Compound 80 was isolated as a side product during the synthesis of Compound 78. 1H NMR (400 MHz, CHLOROFORM-d) δ ppm 3.12 (s, 3H) 3.47 (m, 3H) 3.65 (d, J=14.4 Hz, 1) 3.77 (d, J=14.4 Hz, 1H) 4.73-4.88 (mABq, J=15.4 Hz, 2H) 6.45-6.51 (m, 2H) 6.79 (m, 1H) 7.20 (t, J=8.4 Hz, 1H) 7.31-7.38 (m, 2H) 7.46 (dd, J=8.5, 1.6 Hz, 1H) 7.67-7.72 (m, 3H) 7.75 (br.s, 1H). MS [m+H] calc'd $C_{27}H_{26}N_5O_3$ 468; found 468.

Example 75

Preparation of 6-(aminomethyl)-7-(bis(naphthalen-2-ylmethyl)amino)-5-(3-hydroxyphenyl)-1,3-dimethylpyrido[2,3-d]pyrimidine-2,4(1H,3H)-dione (Compound 81)

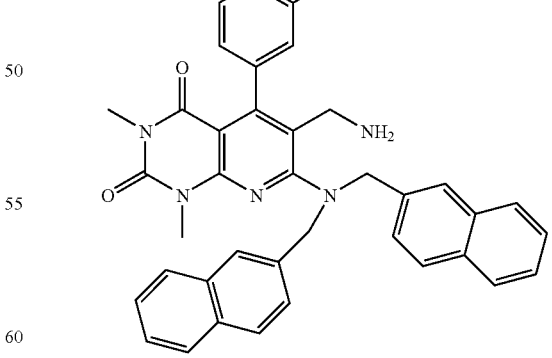

Compound 81 was isolated as a side product during the synthesis of Compound 80. 1H NMR (400 MHz, CHLOROFORM-d) δ ppm 3.22 (s, 3H) 3.34 (br.s, 2H) 3.50 (s, 2H) 3.84 (d, J=14.7 Hz, 1H) 3.99 (d, J=14.7 Hz, 1H) 4.79 (ABq, J=15.7 Hz 4H) 6.50 (d, J=7.6 Hz, 1H) 6.62 (s, 1H) 6.87 (dd, J=8.2, 2.2

Hz, 1H) 7.29 (dd, J=8.6, 1.52 Hz, 2H) 7.42-7.46 (m, 4H) 7.66 (s, 2H) 7.72-7.80 (m, 6H). MS [m+H] calc'd $C_{38}H_{34}N_5O_3$ 565; found 565.

Example 76

Preparation of 6-(aminomethyl)-7-(3-(benzyloxy)benzylamino)-5-(5-fluoro-2-methoxyphenyl)-1,3-dimethylpyrido[2,3-d]pyrimidine-2,4(1H,3H)-dione (Compound 82)

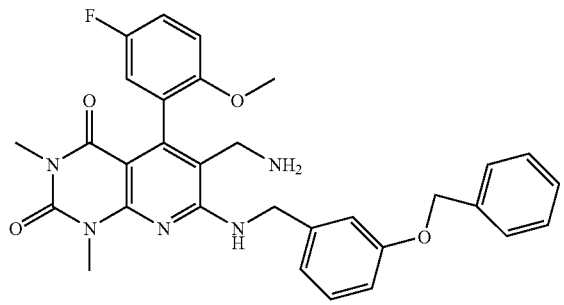

The synthesis of title compounds started from Compound 70a and 1-(benzyloxy)-3-(bromomethyl)benzene, according to procedures described in the synthesis of Compound 70. 1H NMR (400 MHz, CHLOROFORM-d) δ ppm 3.25 (s, 3H) 3.54 (s, 3H) 3.74 (s, 3H) 3.76 (d, J=14.4 Hz, 1H) 3.86 (d, J=14.4 Hz, 1H) 4.73 (q, J=15.2 Hz, 2H) 5.06 (s, 1H) 6.72-6.77 (dd, J=3.1, 16.6 Hz 1H) 6.88 (d, J=8.3 Hz 1H) 7.00-7.07 (m, 3H) 7.11-7.19 (m, 1H) 7.25 (t, J=7.8 Hz, 1H) 7.29-7.33 (m, 1H) 7.33-7.44 (m, 5H). MS [m+H] calc'd $C_{31}H_{31}FN_5O_4$ 556; found 556.

Example 77

Preparation of 6-(aminomethyl)-5-(5-fluoro-2-methoxyphenyl)-7-(3-isobutoxybenzylamino)-1,3-dimethylpyrido[2,3-d]pyrimidine-2,4(1H,3H)-dione (Compound 83)

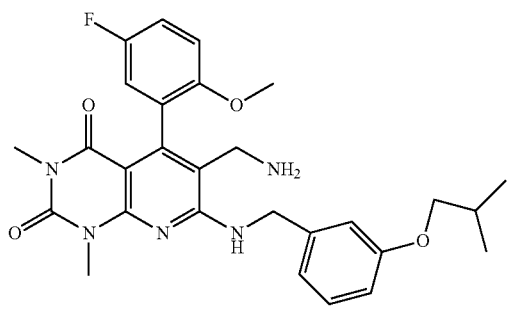

The synthesis of title compounds started from Compound 70a and 1-(bromomethyl)-3-isobutoxybenzene, according to procedures described in the synthesis of Compound 70. 1H NMR (400 MHz, CHLOROFORM-d) δ ppm 0.96 (d, J=6.6 Hz, 6H) 1.95-2.04 (m, 1H) 3.19 (s, 3H) 3.53 (s, 1H) 3.65 (d, J=8.6 Hz, 2H) 3.69 (s, 3H) 3.88 (d, J=14.4 Hz, 1H) 4.55 (d, J=14.9 Hz, 1H) 4.68 (d, J=14.9 Hz, 1H) 6.67 (dd, J=8.3, 3.0 Hz, 1H) 6.73 (dd, J=7.9, 2.1 Hz, 1H) 6.85-6.92 (m, 2H) 6.98 (dd, J=9.1, 4.3 Hz 1H) 7.05-7.12 (m, 1H) 7.14 (t, J=8.0 Hz 1H). MS [m+H] calc'd $C_{28}H_{33}FN_5O_4$ 522. found 522.

Example 78

Preparation of 6-(aminomethyl)-5-(2,4-dichlorophenyl)-7-(2,5-dipropoxybenzylamino)-1,3-dimethylpyrido[2,3-d]pyrimidine-2,4(1H,3H)-dione (Compound 84)

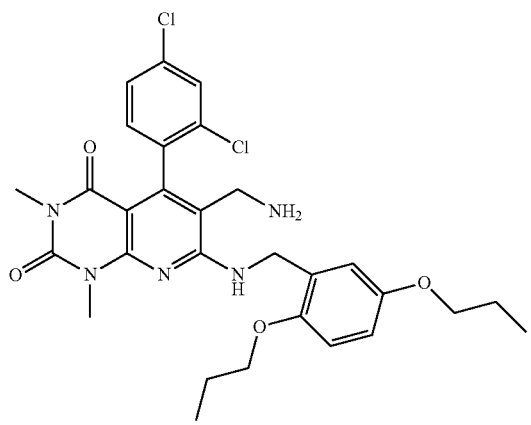

The synthesis of title compounds started from Compound 34 and 2-(bromomethyl)-1,4-dipropoxybenzene, according to procedures described in the synthesis of Compound 56. 1H NMR (400 MHz, CHLOROFORM-d) δ ppm 0.90 (t, J=7.3 Hz, 3H) 0.94 (t, J=7.3 Hz, 3H) 1.59-1.75 (m, 4H) 3.37 (s, 3H) 3.57 (s, 3H) 3.74 (t, J=6.7 Hz 1H) 3.83 (t, J=6.4 Hz 1H) 4.68 (q, J=15.4 Hz 1H) 6.64 (dd, J=8.8, 3.0 Hz, 1H) 6.71 (d, J=8.9 Hz, 1H) 6.77 (d, J=3.0 Hz, 1H) 7.01 (d, J=8.3 Hz, 1H) 7.27 (dd, J=8.3, 2.0 Hz, 1H) 7.42 (d, J=2.0 Hz, 1H). MS [m+H] calc'd $C_{29}H_{34}Cl_2N_5O_4$ 586; found 586.

Example 79

Preparation of 7-(3-(1H-pyrrol-1-yl)benzylamino)-6-(aminomethyl)-5-(3,5-dimethoxyphenyl)-1,3-dimethylpyrido[2,3-d]pyrimidine-2,4(1H,3H)-dione (Compound 85)

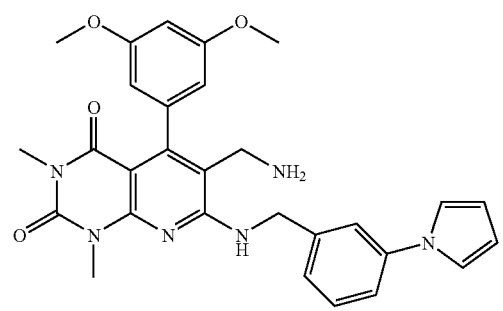

The synthesis of title compounds started from Compound 57a (Example 52) and 1-(3-(bromomethyl)phenyl)-1H-pyrrole, according to procedures described in the synthesis of Compound 56. 1H NMR (400 MHz, CHLOROFORM-d) δ ppm 3.15 (s, 3H) 3.45 (s, 3H) 3.70 (s, 6H) 3.74 (s, 2H) 4.69 (s, 2H) 6.18 (d, J=2.3 Hz, 2H) 6.23 (t, J=2.2 Hz, 2H) 6.43 (t, J=2.2 Hz, 1H) 6.99 (t, J=2.3 Hz, 2H) 7.17-7.22 (m, 2H) 7.26-7.29 (m, 1H) 7.37 (s, 1H). MS [m+H] calc'd $C_{29}H_{31}N_6O_4$ 527; found 527.

Example 80

Preparation of 5-(3,5-dimethoxyphenyl)-6-((ethylamino)methyl)-1,3-dimethyl-7-(naphthalen-2-ylmethylamino)pyrido[2,3-d]pyrimidine-2,4(1H,3H)-dione (Compound 86)

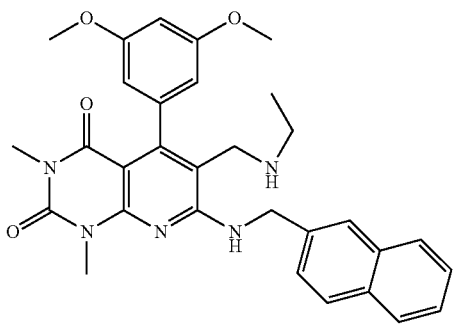

The synthesis of title compounds started from Compound 57a (Example 52) and 2-(bromomethyl)naphthalene, according to procedures described in the synthesis of Compound 56. 1H NMR (400 MHz, CHLOROFORM-d) δ ppm 1.03 (t, J=7.3 Hz, 3H) 2.64 (q, J=7.2 Hz, 2H) 3.15 (s, 3H) 3.48 (s, 2H) 3.72 (s, 6H) 3.81 (s, 2H) 4.78 (s, 2H) 6.21 (d, J=2.0 Hz, 2H) 6.44 (t, J=2.0 Hz, 1H) 7.33-7.40 (m, 2H) 7.44 (d, J=8.8 Hz, 1H) 7.69-7.76 (m, 4H). MS [m+H] calc'd $C_{31}H_{34}N_5O_4$ 540; found 540.

Example 81

Preparation of 6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione (Compound 87)

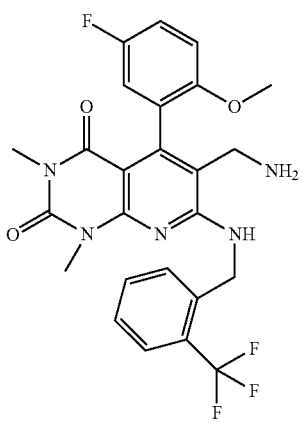

The synthesis of title compounds started from Compound 70a and 1-(bromomethyl)-2-(trifluoromethyl)benzene, according to procedures described in the synthesis of Compound 70. MS [m+H] calc'd $C_{25}H_{24}FN_5O_3$ 518; found 518.

Example 82

Preparation of 6-(Aminomethyl)-5-(5-chloro-2-isobutoxyphenyl)-1,3-dimethyl-7-(naphthalen-2-ylmethylamino)pyrido[2,3-d]pyrimidine-2,4(1H, 3H)-dione (Compound 88)

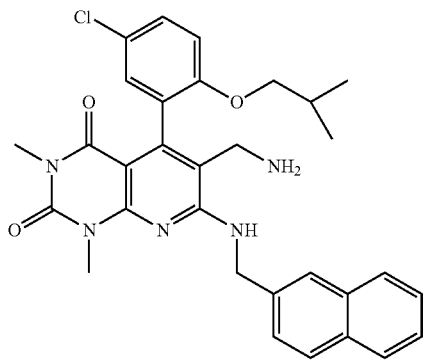

The synthesis of title compounds started from 5-chloro-2-isobutoxybenzaldehyde and 6-amino-1,3-dimethylpyrimidine-2,4(1H,3H)-dione, according to procedures described in the synthesis of Compound 56. $^1$H NMR (400 MHz, CHLOROFORM-d) δ MS [m+H] calc'd $C_{31}H_{33}ClN_5O_3$ 558; found 558.

Example 83

Preparation of 6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4 (1H,3H)-dione (Compound 89)

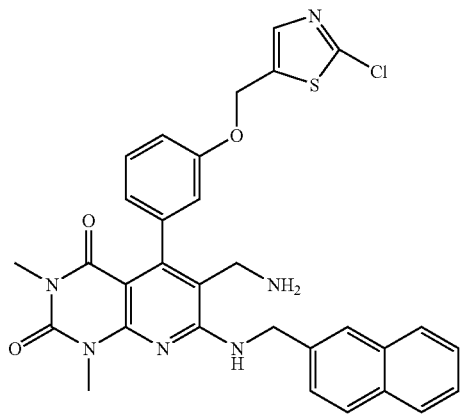

The synthesis of title compounds started from 3-((2-chlorothiazol-5-yl)methoxy)benzaldehyde and 6-amino-1,3-dimethylpyrimidine-2,4(1H,3H)-dione, according to procedures described in the synthesis of Compound 56. 1H NMR (400 MHz, CHLOROFORM-d) δ ppm 3.18 (s, 3H) 3.53 (s, 3H) 3.75 (d, J=2.02 Hz, 2H) 4.85 (brs, 2H) 5.12 (brs, 2H) 6.68 (dd, J=2.40, 1.39 Hz, 1H) 6.73 (d, J=7.58 Hz, 1H) 6.97 (dd, J=8.59, 2.78 Hz, 1H) 7.35-7.44 (m, 3H) 7.46-7.50 (m, 2H) 7.72-7.80 (m, 4H). MS [m+H] calc'd $C_{31}H_{28}ClN_6O_2S$ 560. found 560.

Example 84

Preparation of 6-(Aminomethyl)-5-(3-fluorophenyl)-1,3-dimethyl-7-(naphthalen-2-ylmethylamino)pyrido[2,3-d]pyrimidine-2,4(1H,3H)-dione (Compound 90)

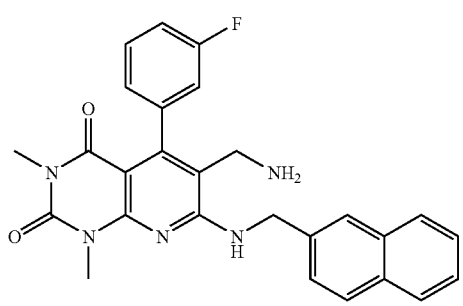

The synthesis of title compounds started from 3-fluorobenzaldehyde and 6-amino-1,3-dimethylpyrimidine-2,4(1H,3H)-dione, according to procedures described in the synthesis of Compound 56. MS [m+H] calc'd $C_{27}H_{25}FN_5O_2$ 470; found 470.

Example 85

Preparation of 6-(Aminomethyl)-5-(2-bromo-5-fluorophenyl)-7-(1,2-diphenylethylamino)-1,3-dimethylpyrido[2,3-d]pyrimidine-2,4(1H,3H)-dione (Compound 91)

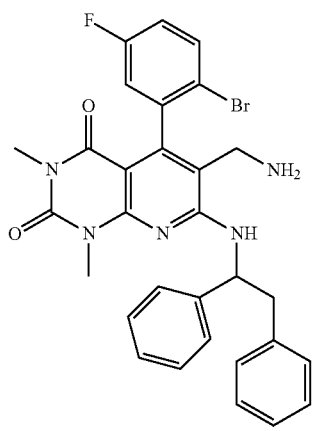

The title compound was prepared from Compound 47a (Example and 1,2-diphenylethanamine, according to procedure described in the synthesis of Compound 47. MS [m+H] calc'd $C_{30}H_{28}BrFN_5O_2$ 588; found 588.

Example 86

Preparation of 5-(3,5-dimethoxyphenyl)-1,3-dimethyl-7-(methyl(naphthalen-2-ylmethyl)amino)-6-((methylamino)methyl)pyrido[2,3-d]pyrimidine-2,4(1H,3H)-dione (Compound 92)

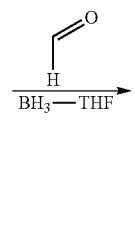

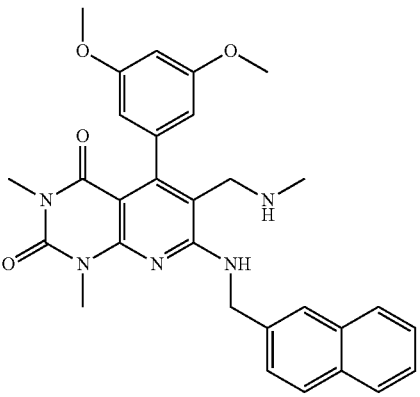

Compound 57 (50 mg, 0.1 mmol) was treated with 30% formaldehyde (20 mg, 0.2 mmol) in toluene with a catalytic amount of TFA, and then concentrated. The crude mixture was treated with $BH_3$-THF at refluxe condition for 10 min, purified bu LC-MS to give title compound 92. 1H NMR (400 MHz, CHLOROFORM-d) δ ppm 2.51 (s, 3H) 3.16 (s, 3H) 3.34 (s, 6H) 3.73 (s, 6H) 4.80 (br. s., 2H) 6.12 (d, J=2.02 Hz, 1H) 6.21 (d, J=2.27 Hz, 1H) 6.45 (t, J=2.15 Hz, 1H) 7.33-7.42 (m, 2H) 7.45 (d, J=8.34 Hz, 1H) 7.68-7.78 (m, 4H). MS [m+H] calc'd $C_{31}H_{34}N_5O_4$ 540; found 540.

Example 87

Preparation of 6-(Aminomethyl)-5-(5-fluoro-2-methoxyphenyl)-1,3-dimethyl-7-(phenethylamino)pyrido[2,3-d]pyrimidine-2,4(1H,3H)-dione (Compound 93)

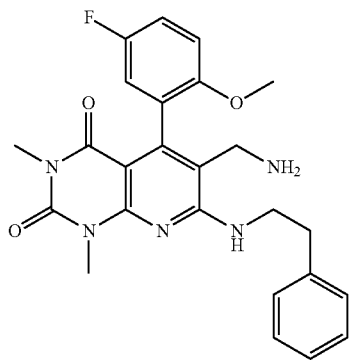

The synthesis of title compounds started from Compound 70a (Example 64) and 1-(bromoethyl)benzene, according to procedures described in the synthesis of Compound 56. $^1$H NMR (400 MHz, CHLOROFORM-d) δ MS [m+H] calc'd $C_{25}H_{27}FN_5O_3$ 464; found 464.

In addition to the examples described above, the following non-limiting group of compounds can be prepared utilizing the above reaction schemes, and variations thereof, with the appropriate selection of substituents.

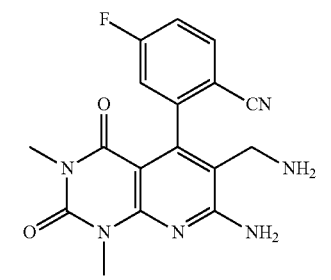

2-(7-amino-6-(aminomethyl)-1,3-dimethyl-2,4-dioxo-1,2,3,4-tetrahydropyrido[2,3-d]pyrimidin-5-yl)-4-fluorobenzonitrile

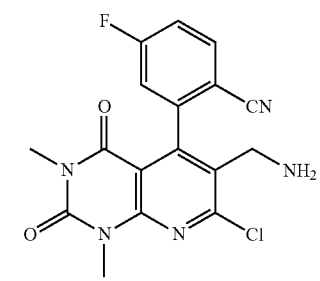

2-(6-(aminomethyl)-7-chloro-1,3-dimethyl-2,4-dioxo-1,2,3,4-tetrahydropyrido[2,3-d]pyrimidin-5-yl)-4-fluorobenzonitrile

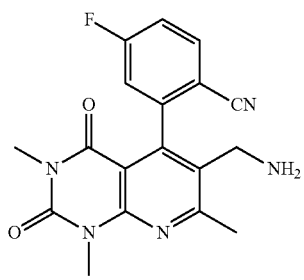

2-(6-(aminomethyl)-1,3,7-trimethyl-2,4-dioxo-1,2,3,4-tetrahydropyrido[2,3-d]pyrimidin-5-yl)-4-fluorobenzonitrile

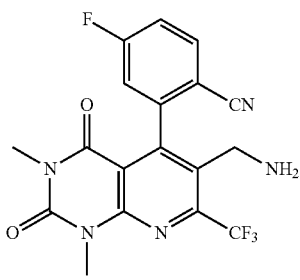

2-(6-(aminomethyl)-1,3-dimethyl-2,4-dioxo-7-(trifluoromethyl)-1,2,3,4-tetrahydropyrido[2,3-d]pyrimidin-5-yl)-4-fluorobenzonitrile

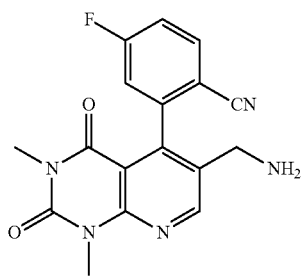

2-(6-(aminomethyl)-1,3-dimethyl-2,4-dioxo-1,2,3,4-tetrahydropyrido[2,3-d]pyrimidin-5-yl)-4-fluorobenzonitrile

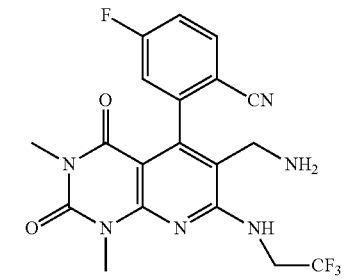

2-(6-(aminomethyl)-1,3-dimethyl-2,4-dioxo-7-(2,2,2-trifluoroethylamino)-1,2,3,4-tetrahydropyrido[2,3-d]pyrimidin-5-yl)-4-fluorobenzonitrile

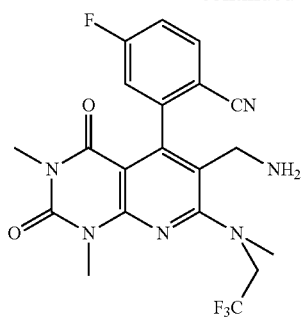

2-(6-(aminomethyl)-1,3-dimethyl-7-
(methyl(2,2,2-trifluoroethyl)amino)-2,4-
dioxo-1,2,3,4-tetrahydropyrido[2,3-
d]pyrimidin-5-yl)-4-fluorobenzonitrile

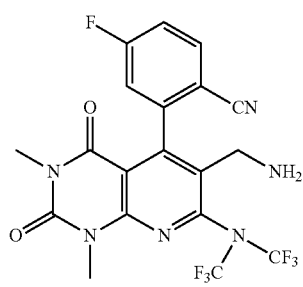

2-(6-(aminomethyl)-7-
(bis(trifluoromethyl)amino)-1,3-dimethyl-
2,4-dioxo-1,2,3,4-tetrahydropyrido[2,3-
d]pyrimidin-5-yl)-4-fluorobenzonitrile

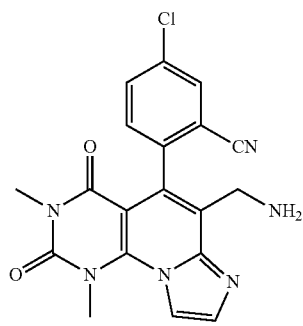

2-(6-(aminomethyl)-1,3-dimethyl-2,4-
dioxo-7,8-imidazo-[1,2-a]-1,2,3,4,7,8-
hexahydropyrido[2,3-d]pyrimidin-5-yl)-5-
chlorobenzonitrile

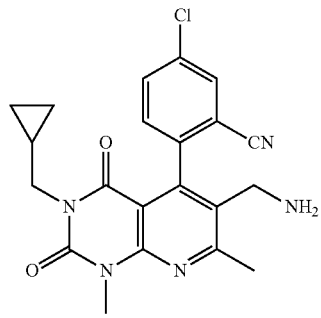

2-(6-(aminomethyl)-3-(cyclopropylmethyl)-
1,7-dimethyl-2,4-dioxo-1,2,3,4-
tetrahydropyrido[2,3-d]pyrimidin-5-yl)-5-
chlorobenzonitrile

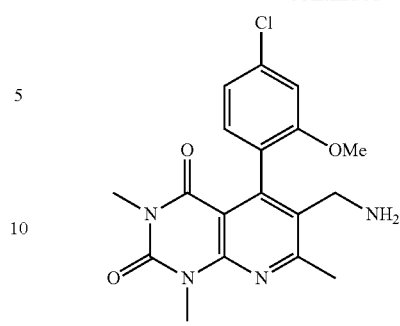

6-(aminomethyl)-5-(4-chloro-2-
methoxyphenyl)-1,3,7-trimethylpyrido[2,3-
d]pyrimidine-2,4(1H,3H)-dione

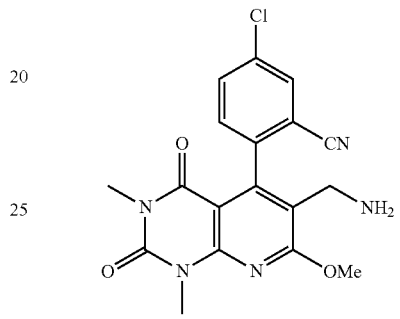

2-(6-(aminomethyl)-7-methoxy-1,3-
dimethyl-2,4-dioxo-1,2,3,4-
tetrahydropyrido[2,3-d]pyrimidin-5-yl)-5-
chlorobenzonitrile

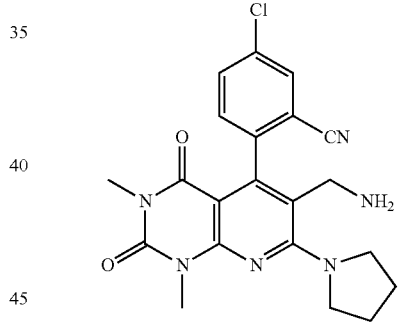

2-(6-(aminomethyl)-1,3-dimethyl-2,4-
dioxo-7-(pyrrolidin-1-yl)-1,2,3,4-
tetrahydropyrido[2,3-d]pyrimidin-5-yl)-5-
chlorobenzonitrile

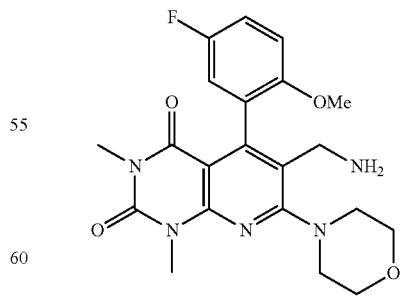

6-(aminomethyl)-5-(5-fluoro-2-
methoxyphenyl)-1,3-dimethyl-7-
morpholinopyrido[2,3-d]pyrimidine-
2,4(1H,3H)-dione

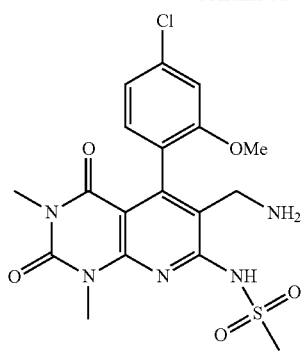

N-(6-(aminomethyl)-5-(4-chloro-2-methoxyphenyl)-1,3-dimethyl-2,4-dioxo-1,2,3,4-tetrahydropyrido[2,3-d]pyrimidin-7-yl)methanesulfonamide

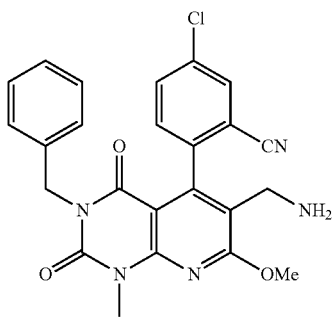

2-(6-(aminomethyl)-3-benzyl-7-methoxy-1-methyl-2,4-dioxo-1,2,3,4-tetrahydropyrido[2,3-d]pyrimidin-5-yl)-5-chlorobenzonitrile

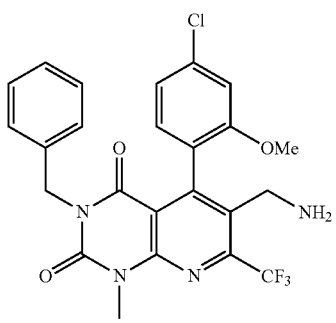

6-(aminomethyl)-3-benzyl-5-(4-chloro-2-methoxyphenyl-1-methyl-7-(trifluoromethyl)pyrido[2,3-d]pyrimidine-2,4(1H,3H)-dione

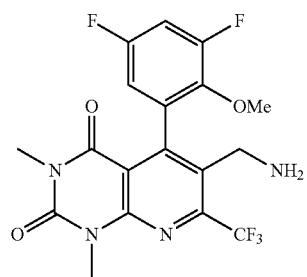

6-(aminomethyl)-5-(3,5-difluoro-2-methoxyphenyl)-1,3-dimethyl-7-(trifluoromethyl)pyrido[2,3-d]pyrimidine-2,4(1H,3H)-dione

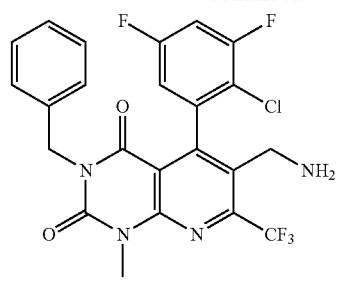

6-(aminomethyl)-3-benzyl-5-(2-chloro-3,5-difluorophenyl-1-methyl-7-(trifluoromethyl)pyrido[2,3-d]pyrimidine-2,4(1H,3H)-dione

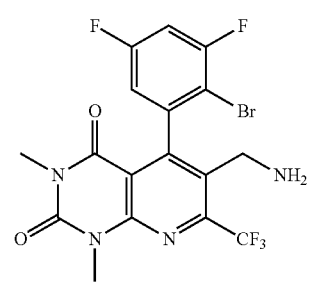

6-(aminomethyl)-5-(2-bromo-3,5-difluorophenyl)-1,3-dimethyl-7-(trifluoromethyl)pyrido[2,3-d]pyrimidine-2,4(1H,3H)-dione

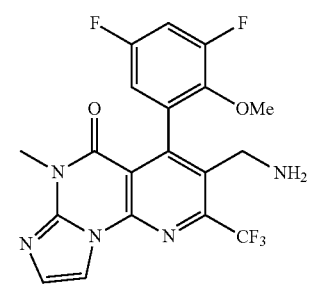

6-(aminomethyl)-5-(3,5-difluoro-2-methoxyphenyl)-1,2-imidazo-[1,2-a]-3-methyl-7-(trifluoromethyl)-2,3-dihydropyrido[2,3-d]pyrimidin-4(1H)-one

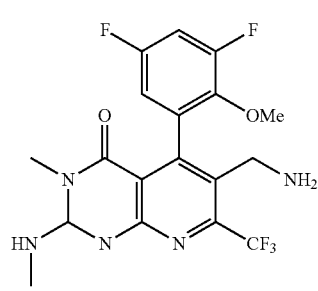

6-(aminomethyl)-5-(3,5-difluoro-2-methoxyphenyl)-3-methyl-2-(methylamino)-7-(trifluoromethyl)pyrido[2,3-d]pyrimidin-4(3H)-one

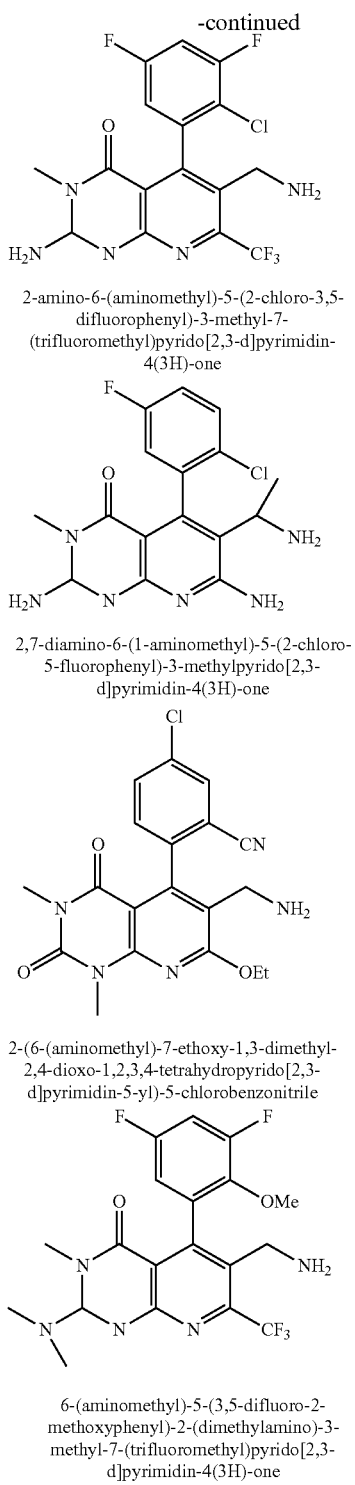

2-amino-6-(aminomethyl)-5-(2-chloro-3,5-
difluorophenyl)-3-methyl-7-
(trifluoromethyl)pyrido[2,3-d]pyrimidin-
4(3H)-one 2,7-diamino-6-(1-aminomethyl)-5-(2-chloro-
5-fluorophenyl)-3-methylpyrido[2,3-
d]pyrimidin-4(3H)-one 2-(6-(aminomethyl)-7-ethoxy-1,3-dimethyl-
2,4-dioxo-1,2,3,4-tetrahydropyrido[2,3-
d]pyrimidin-5-yl)-5-chlorobenzonitrile 6-(aminomethyl)-5-(3,5-difluoro-2-
methoxyphenyl)-2-(dimethylamino)-3-
methyl-7-(trifluoromethyl)pyrido[2,3-
d]pyrimidin-4(3H)-one

Example A

Expression of Preprorenin and Purification of Prorenin

The sequence of human wild-type renin is known in the art; see, Imai, T. et al., Proc. Natl. Acad. Sci. USA 1983, 80, 7105-7409. It is noted that the fragment of the renin protein useful for the assay comprises amino acid residues 67-406 of human renin (active renin). To prepare active renin, a fragment longer than active renin, a preprorenin (e.g., comprising residues 1-406), may be expressed and from which a prorenin (e.g., comprising residues 23-406) may be recovered. The prorenin may later be cleaved to obtain active renin.

Expression of human preprorenin (residues 1-406) can be conducted using a FreeStyle 293 Expression System (Invitrogen Corp.), wherein the plasmid DNA for human prorenin expression (pcDNA3.1(+)/hREN) is used to conduct transient expression in FreeStyle 293-F cells. After transfection of the plasmid DNA, the cells are subjected to shaking at 37° C., 8% CO2 and 125 rpm for 3 days.

The prorenin protein is then accumulated and purified by salting out. Powdered ammonium sulfate is added to the culture medium and dissolved to make a 40% saturation of the salt. The resulting precipitate can be collected by centrifugation and discarded. Ammonium sulfate is added to the remaining solution and dissolved to make an 80% saturation of salt. The resulting precipitate can be collected by, for example, centrifugation. The prorenin protein is recovered by dissolving the precipitate in buffer.

The concentrated liquid is subjected to gel filtration chromatography using, for example, HiLoad 16/60 Superdex 200 pg (Amersham Biosciences, Inc.) equilibrated with 20 mM Tris-hydrochloric acid (pH 8.0) containing 0.15 M sodium chloride, at a flow rate of 1.4 ml/min, to obtain 3.6 mg of purified prorenin (residues 24-406).

Example B

Purification of Active Renin

To 3.6 mg of prorenin (residues 24-406, as prepared in Example A) dissolved in 5.2 ml of 0.1 M Tris-hydrochloric acid (pH 8.0), is added 12 μg of trypsin (Roche Diagnostics Corp.), and the mixture is allowed to react at 28° C. for 55 minutes to carry out activation of renin. After the reaction, 0.4 ml of immobilized trypsin inhibitor (Pierce Biotechnology, Inc.) is added to remove the trypsin used in the activation, by adsorption. The reaction liquid containing the active renin is concentrated using Vivaspin 20 (molecular weight of the fraction 10,000; Vivascience, Inc.), and diluted with 20 mM Tris-hydrochloric acid (pH 8.0). The diluted liquid is fed to a TSKgel DEAE-5 PW column (7.5 mm I.D.×75 mm, Tosoh Corp.) equilibrated with 20 mM Tris-hydrochloric acid (pH 8.0) at a flow rate of 1 ml/min to adsorb the active renin (residues 67-406). The column is washed with the buffer solution used for the equilibration, and then elution is carried out by means of a linear concentration gradient of sodium chloride from 0 M to 0.3 M, to obtain 1.5 mg of purified active renin (residues 67-406).

Example C

Establishment of Renin Expressing Vector

A plasmid DNA to express human renin in HEK293 cells can be prepared as follows. PCR is carried out using human renal cDNA (Clontech Laboratories, Inc., Marathon Ready cDNA) as the template and using two synthetic DNAs (5'-AAGCTTATGGATGGATGGAGA-3' (SEQ ID NO: 1) and 5'-GGATCCTCAGCGGGCCAAGGC-3' (SEQ ID NO: 2)), and the obtained fragment is cloned using TOPO TA Cloning Kit (Invitrogen Corp.). The obtained fragment is subcloned into pcDNA3.1(+) that has been cleaved by HindIII and BamHI, to obtain a plasmid DNA for human preprorenin expression (pcDNA3.1(+)/hREN). The sequences of the two

Example D

Assaying the in vitro Enzymatic Activity of Renin Inhibitors

Solutions of test compounds in varying concentrations ($\leq 2$ mM final concentration) are prepared in dimethyl sulfoxide (DMSO) and then diluted into assay buffer comprising 50 mM Hepes, 1 mM EDTA, 1 mM DTT, 0.1 mg/ml BSA, 0.01% Brij35, pH 7.4. Alternatively, the assay can be performed with a high BSA concentration, wherein the buffer contains an additional 2% BSA.

Recombinant human renin (3 nM final concentration) is added to the dilutions and pre-incubated with the compounds for 10 minutes at 37° C. As described in Examples A-C above, human renin can be obtained by expressing preprorenin (residue 1-406) in mammalian cells, treating the prorenin (residues 24-406) contained in the culture supernatant with trypsin, and isolate the active form (residues 67-406). After pre-incubation, the reaction is initiated with 1 μM of substrate QXL520-γ-Abu-Ile-His-Pro-Phe-His-Leu-Val-Ile-His-Thr-Lys (HiLyteFluo488)-Arg-OH (Anaspec, San Jose, Calif.). The final DMSO in the assay is 5%. The total volume of the reaction mixture is 20 μL, which can be placed on Greiner 384-well small volume plates.

Renin activity may be determined via fluorescence (excitation $\lambda=485$ nm; emission $\lambda=538$ nm), e.g., on a Molecular Devices SPECTROmax GEMINI XPS. The fluorescence intensity is determined upon the addition of substrate and determined again after incubation at 37° C. for one hour. The fluorescence intensity of a blank (no inhibition) using vehicle alone is also determined. Renin activity is linearly proportional to the change in fluorescence observed (final—initial).

The percent inhibition of renin at a given compound concentration is defined as:

$$100\% \times [1-(Fcompound/Fblank)]$$

where Fcompound is the observed fluorescence at a given concentration of test compound and Fblank is the observed fluorescence in the presence of vehicle alone.

The pIC50 value (negative log of the molar concentration of the compound that produces 50% inhibition) of a test compound is calculated by non-linear least squares curve fitting of the equation:

$$\text{Percent Inhibition} = 100\%/(1+(10-pIC50/10 \log [I]))$$

to percent inhibition versus compound concentration. The 50% inhibitory concentration ($IC_{50}$) of a test compound is calculated by raising 10 to the negative $pIC_{50}$ ($10-pIC_{50}$).

Example E

Assaying the in vitro Enzymatic Activity of Inhibitors Against DPP-IV

Solutions of test compounds in varying concentrations (10 mM final concentration) were prepared in dimethyl sulfoxide (DMSO) and then diluted into assay buffer comprising: 20 mM Tris, pH 7.4; 20 mM KCl; and 0.1 mg/mL BSA. Human DPP-IV (0.1 nM final concentration) was added to the dilutions and pre-incubated for 10 minutes at ambient temperature before the reaction was initiated with A-P-7-amido-4-trifluoromethylcoumarin (AP-AFC; 10 μM final concentration). The total volume of the reaction mixture was 10-100 μL depending on assay formats used (384 or 96 well plates). The reaction was followed kinetically (excitation $\lambda=400$ nm; emission $\lambda=505$ nm) for 5-10 minutes or an endpoint was measured after 10 minutes. Inhibition constants ($IC_{50}$) were calculated from the enzyme progress curves using standard mathematical models.

Example F

Assaying the in vitro Enzymatic Activity of Inhibitors Against FAPα

Solutions of test compounds in varying concentrations ($\leq 10$ mM final concentration) were prepared in dimethyl sulfoxide (DMSO) and then diluted into assay buffer comprising: 20 mM Tris, pH 7.4; 20 mM KCl; and 0.1 mg/mL BSA. Human FAPα (2 nM final concentration) was added to the dilutions and pre-incubated for 10 minutes at ambient temperature before the reaction was initiated with A-P-7-amido-4-trifluoromethylcoumarin (AP-AFC; 40 μM final concentration). The total volume of the reaction mixture was 10-100 μL depending on assay formats used (384 or 96 well plates). The reaction was followed kinetically (excitation $\lambda=400$ nm; emission $\lambda=505$ nm) for 5-10 minutes or an endpoint was measured after 10 minutes. Inhibition constants ($IC_{50}$) were calculated from the enzyme progress curves using standard mathematical models.

Example G

Assaying the in vitro Enzymatic Activity of Inhibitors Against PREP

Solutions of test compounds in varying concentrations ($\leq 10$ mM final concentration) were prepared in dimethyl sulfoxide (DMSO) and then diluted into assay buffer comprising: 20 mM Sodium Phosphate, pH 7.4; 0.5 mM EDTA; 0.5 mM DTT; and 0.1 mg/mL BSA. PREP (EC3.4.21.26 from Flavobacterium meningosepticum; 0.2 nM final concentration) was added to the dilutions. The PREP and compound were pre-incubated for 10 minutes at ambient temperature before the reaction was initiated with Z-G-P-AMC (10 μM final concentration). The total volume of the reaction mixture was 10-100 μL depending on assay formats used (384 or 96 well plates). The reaction was followed kinetically (excitation $\lambda=375$ nm; emission $\lambda=460$ nm) for 10 minutes or an endpoint was measured after 10 minutes. Inhibition constants ($IC_{50}$) were calculated from the enzyme progress curves using standard mathematical models.

Example H

Assaying the in vitro Enzymatic Activity of Inhibitors Against Tryptase

Solutions of test compounds in varying concentrations ($\leq 10$ mM final concentration) were prepared in dimethyl sulfoxide (DMSO) and then diluted into assay buffer comprising: 100 mM Hepes, pH 7.4; 0.01% Brij35; and 10% glycerol. Tryptase (rhLung beta; 0.1 nM final concentration) was added to the dilutions and pre-incubated with compound for 10 minutes at ambient temperature. The enzymatic reaction was initiated with 25 μM Z-lys-SBz1 and 400 μM DTNB. The total volume of the reaction mixture was 100 μL in Costar A/2 96 well plates. The reaction was followed colorimetrically (λ=405 nm) for 10 minutes Inhibition constants (IC$_{50}$) were calculated from the enzyme progress curves using standard mathematical models.

Compounds of the invention were tested according to the above-described assays for protease inhibition and observed to exhibit selective DPP-IV inhibitory activity. For example, compounds of the invention were found to inhibit DPP-IV activity at concentrations that are at least 50 fold less than those concentrations required to produce an equiactive inhibition of protease activity for FAPα. The apparent inhibition constants (K$_i$) for compounds of the invention, against DPP-IV, were in the range from about $10^{-9}$M to about $10^{-5}$M.

It will be apparent to those skilled in the art that various modifications and variations can be made to the compounds, compositions, kits, and methods of the present invention without departing from the spirit or scope of the invention. Thus, it is intended that the present invention cover the modifications and variations of this invention provided they come within the scope of the appended claims and their equivalents.

IC$_{50}$ values for selected compounds of the present invention are given in Table 1.

TABLE 1

IC$_{50}$ of Exemplified Compounds Against Renin and DPP-IV

| COMPOUND | Renin IC$_{50}$ (μM) | DPP-IV IC$_{50}$ (μM) |
| --- | --- | --- |
| 56 | >100 | >100 |
| 57 | 1-10 | >100 |
| 58 | 1-10 | ND |
| 59 | 1-10 | 10-100 |
| 60 | 1-10 | 10-100 |
| 61 | 1-10 | 10-100 |
| 62 | >100 | >100 |
| 63 | 1-10 | 1-10 |
| 64 | 1-10 | >100 |

TABLE 1-continued

IC$_{50}$ of Exemplified Compounds Against Renin and DPP-IV

| COMPOUND | Renin IC$_{50}$ (μM) | DPP-IV IC$_{50}$ (μM) |
| --- | --- | --- |
| 65 | 10-100 | >100 |
| 66 | 10-100 | >100 |
| 67 | 10-100 | >100 |
| 68 | 10-100 | <1 |
| 69 | 10-100 | <1 |
| 70 | 1-10 | <1 |
| 71 | 1-10 | ND |
| 72 | 1-10 | <1 |
| 73 | 1-10 | ND |
| 75 | 1-10 | <1 |
| 76 | >100 | 10-100 |
| 77 | 1-10 | >100 |
| 79 | 1-10 | 10-100 |
| 80 | 1-10 | 10-100 |
| 82 | 1-10 | <1 |
| 83 | 1-10 | <1 |
| 84 | >100 | 1-10 |
| 85 | 1-10 | >100 |
| 86 | 10-100 | >100 |
| 87 | 1-10 | <1 |
| 88 | 1-10 | 1-10 |
| 89 | 1-10 | 10-100 |
| 90 | 1-10 | 1-10 |
| 91 | 1-10 | <1 |
| 93 | 10-100 | <1 |

ND = not determined

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound having the formula:

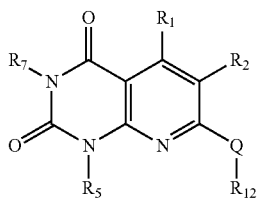

or a pharmaceutically acceptable salt thereof, wherein

Q is selected from the group consisting of —O—, —S—, and —NR$_{13}$—;

R$_1$ is selected from the group consisting of hydrogen, (C$_{1-10}$)alkyl, (C$_{3-12}$)cycloalkyl, (C$_{3-12}$)heterocycloalkyl, aryl(C$_{1-10}$)alkyl, (C$_{1-5}$)heteroarylalkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;

R$_2$ is selected from the group consisting of amino(C$_{1-6}$)alkyl, (C$_{3-12}$)heterocycloalkyl, (C$_{4-12}$)heterobicycloaryl, heteroaryl, and cyano, each substituted or unsubstituted;

R$_5$ and R$_7$ are each independently selected from the group consisting of hydrogen, amino, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, (C$_{3-12}$)cycloalkyl(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted;

R$_{12}$ is selected from the group consisting of (C$_{3-10}$)alkyl, phenyl, phenylalkyl, naphthylalkyl, each substituted or unsubstituted; and R$_{13}$ is selected from the group consisting of hydrogen, (C$_{1-10}$)haloalkyl, amino, thio, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, and imino group, each substituted or unsubstituted.

2. The compound, or pharmaceutically acceptable salt thereof, according to claim 1, wherein R$_5$ and R$_7$ are both methyl.

3. The compound, or pharmaceutically acceptable salt thereof, according to claim 1, wherein R$_2$ is —(CR$_8$R$_9$)$_q$—NR$_{10}$R$_{11}$, where q is 1, 2 or 3;

R$_8$ and R$_9$ are each independently selected from the group consisting of hydrogen, halogen, (C$_{1-10}$)haloalkyl, cyano, nitro, alkyl, cycloalkyl, alkene, alkyne, aryl, and heteroaryl, each substituted or unsubstituted, or where R$_8$ and R$_9$ are taken together to form a substituted or unsubstituted ring; and R$_{10}$ and R$_{11}$ are each independently selected from the group consisting of hydrogen, (C$_{1-10}$)haloalkyl, amino, thio, (C$_{1-10}$)alkyl, (C$_{3-12}$)cycloalkyl, hetero(C$_{1-12}$)cycloalkyl, hydroxyalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, and imino group, each substituted or unsubstituted.

4. The compound, or pharmaceutically acceptable salt thereof, according to claim 3, wherein q is 1.

5. The compound, or pharmaceutically acceptable salt thereof, according to claim 3, wherein R$_8$ and R$_9$ are both hydrogen.

6. The compound, or pharmaceutically acceptable salt thereof, according to claim 3, wherein R$_{10}$ and R$_{11}$ are each independently selected from the group consisting of hydrogen, and substituted or unsubstituted (C$_{1-6}$)alkyl.

7. The compound, or pharmaceutically acceptable salt thereof, according to claim 1, wherein R$_2$ is —CH$_2$NR$_2$.

8. The compound, or pharmaceutically acceptable salt thereof, according to claim 1, wherein Q is —NR$_{13}$—.

9. The compound, or pharmaceutically acceptable salt thereof, according to claim 8, wherein R$_{13}$ is hydrogen.

10. The compound, or pharmaceutically acceptable salt thereof, according to claim 1, wherein R$_{12}$ is selected from the group consisting of phenyl, phenylalkyl, naphthylalkyl, benzyl, and naphthylmethyl, each unsubstituted or substituted.

11. The compound, or pharmaceutically acceptable salt thereof, according to claim 10, wherein each R$_{12}$ is independently unsubstituted or substituted by one or more substituents, where the substituents are independently selected from the group consisting of halo, nitro, cyano, thio, oxy, hydroxy, carbonyloxy, (C$_{1-10}$)alkoxy, (C$_{4-12}$)aryloxy, (C$_{1-10}$)heteroaryl oxy, carbonyl, oxycarbonyl, aminocarbonyl, amino, (C$_{1-10}$)alkylamino, sulfonamido, imino, sulfonyl, sulfinyl, (C$_{1-10}$)alkyl, (C$_{1-10}$)haloalkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, (C$_{3-12}$)heterocycloalkyl(C$_{1-10}$)alkyl, aryl(C$_{1-10}$)alkyl, (C$_{1-10}$)heteroaryl(C$_{1-5}$)alkyl, (C$_{9-12}$)bicycloaryl(C$_{1-5}$)alkyl, (C$_{8-12}$)heterobicycloaryl(C$_{1-5}$)alkyl, (C$_{1-10}$)heteroalkyl, (C$_{3-12}$)cycloalkyl, (C$_{3-12}$)heterocycloalkyl, (C$_{9-12}$)bicycloalkyl, (C$_{3-12}$)heterobicycloalkyl, (C$_{4-12}$)aryl, (C$_{1-10}$)heteroaryl, (C$_{9-12}$)bicycloaryl and (C$_{4-12}$)heterobicycloaryl, each unsubstituted or further substituted.

12. The compound, or pharmaceutically acceptable salt thereof, according to claim 10, wherein the phenyl rings and the naphthyl ring of R$_{12}$ are independently unsubstituted or substituted with one or more substituents selected from the group consisting of —CF$_3$, —OCH$_3$, —OCH$_2$CH(CH$_3$)$_2$, —NH—CH$_2$CH$_3$, —NHC(O)CH$_3$, —OCH$_2$CH$_2$CH$_3$, —C(O)NCH$_2$CH$_2$CH$_3$, benzyoxy,

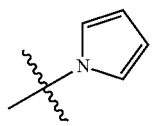

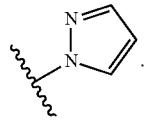
13. The compound, or pharmaceutically acceptable salt thereof, according to claim 3, wherein $R_{12}$ is selected from the group consisting of: —CH(CH$_2$CH$_3$)$_2$,
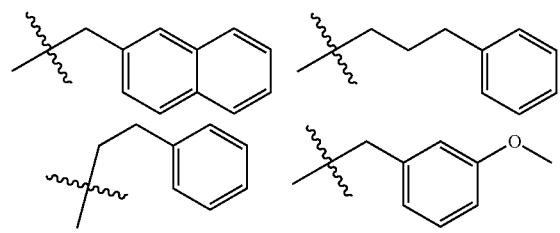
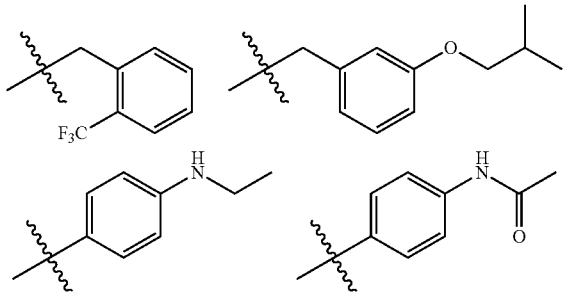
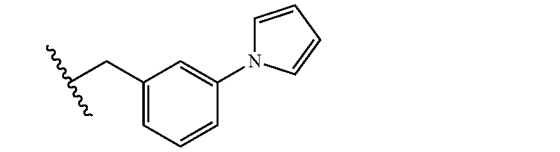
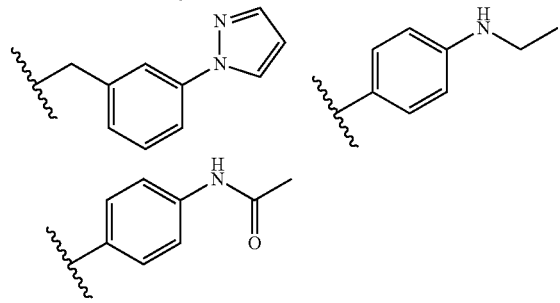
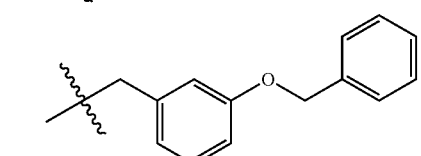
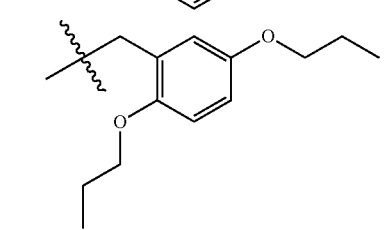
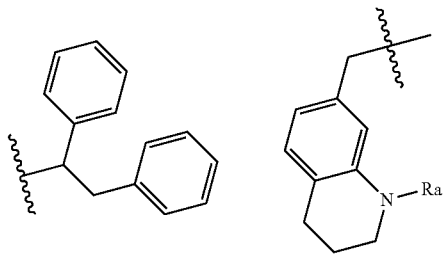
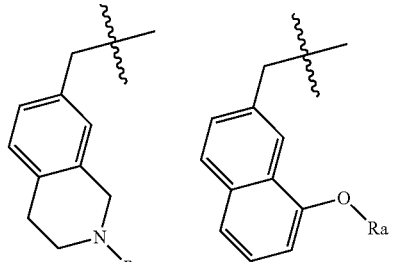
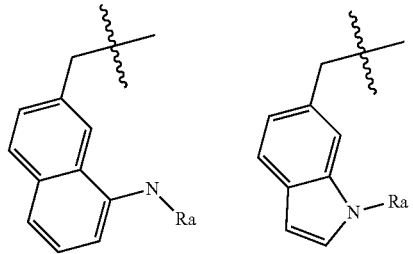
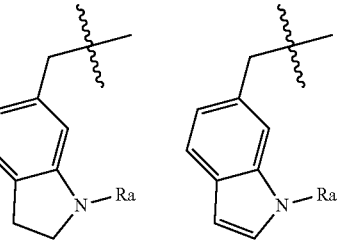
$R_a$ is selected from the group consisting of —(CH$_2$)$_2$OCH$_3$, —(CH$_2$)$_3$OCH$_3$, —(CH$_2$)$_2$NHC(O)CH$_3$, —(CH$_2$)$_3$NHC(O)CH$_3$,
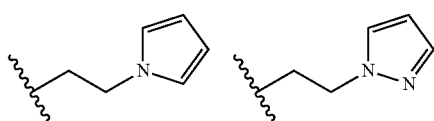
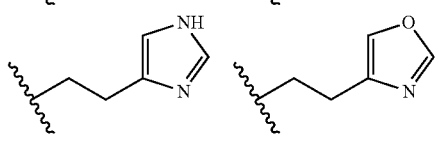

14. The compound, or pharmaceutically acceptable salt thereof, according to claim 1, wherein $R_1$ is

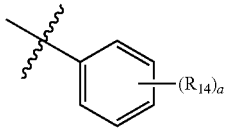

where a is 0, 1, 2, 3, 4, or 5; and $R_{14}$ is selected from the group consisting of hydrogen, halo, $(C_{1-10})$perhaloalkyl, amino, nitro, cyano, thio, sulfonamido, $(C_{1-10})$alkyl, $(C_{3-12})$cycloalkyl, $(C_{3-12})$heterocycloalkyl, aryl$(C_{1-5})$alkyl, heteroaryl$(C_{1-5})$alkyl, $(C_{9-12})$bicycloaryl, $(C_{4-12})$heterobicycloaryl, carbonyl $(C_{1-3})$alkyl, thiocarbonyl$(C_{1-3})$alkyl, sulfonyl$(C_{1-3})$ alkyl, sulfinyl$(C_{1-3})$alkyl, imino$(C_{1-3})$alkyl, aryl, heteroaryl, hydroxy, alkoxy, aryloxy, heteroaryloxy, carbonyl group, imino group, sulfonyl group and sulfinyl group, each substituted or unsubstituted.

15. The compound, or pharmaceutically acceptable salt thereof, according to claim 1, wherein $R_1$ is selected from the group consisting of:

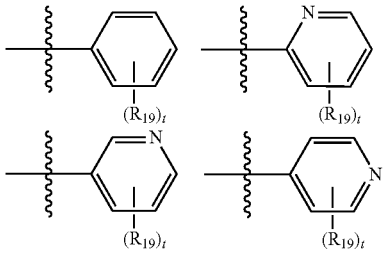

wherein t is 0, 1, 2, 3, 4 or 5; and each $R_{19}$ is independently selected from the group consisting of halo, $(C_{1-10})$perhaloalkyl, $CF_3$, $(C_{1-10})$alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted, or two $R_{19}$ are taken together to form an unsubstituted or substituted ring.

16. The compound, or pharmaceutically acceptable salt thereof, according to claim 1, wherein $R_1$ is selected from the group consisting of:

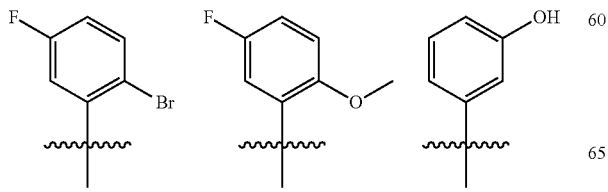

-continued

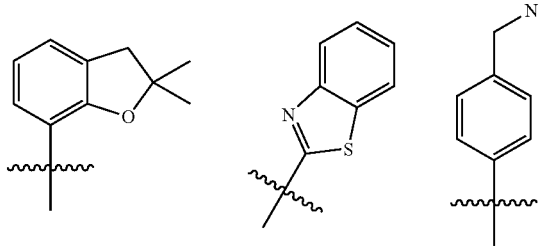

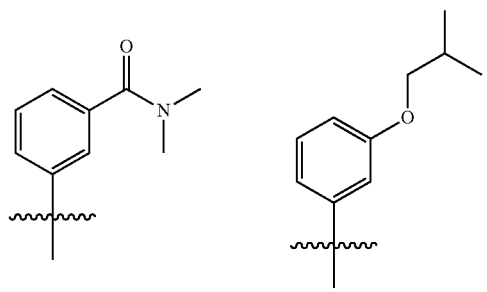

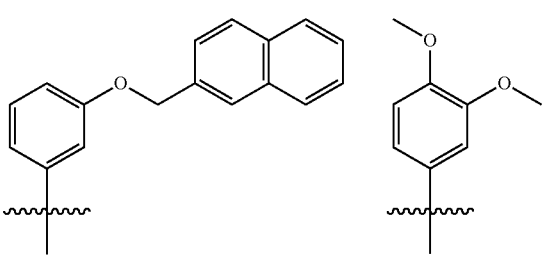

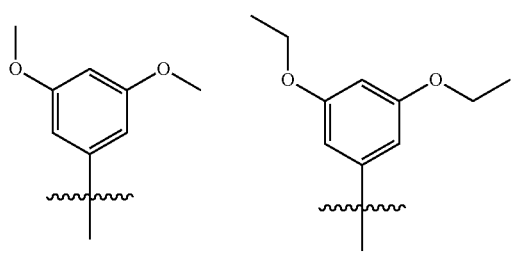

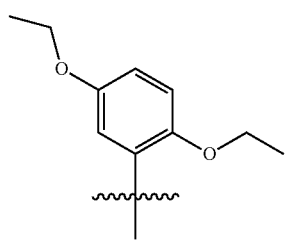

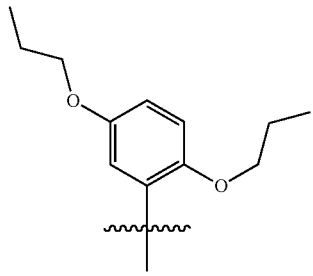

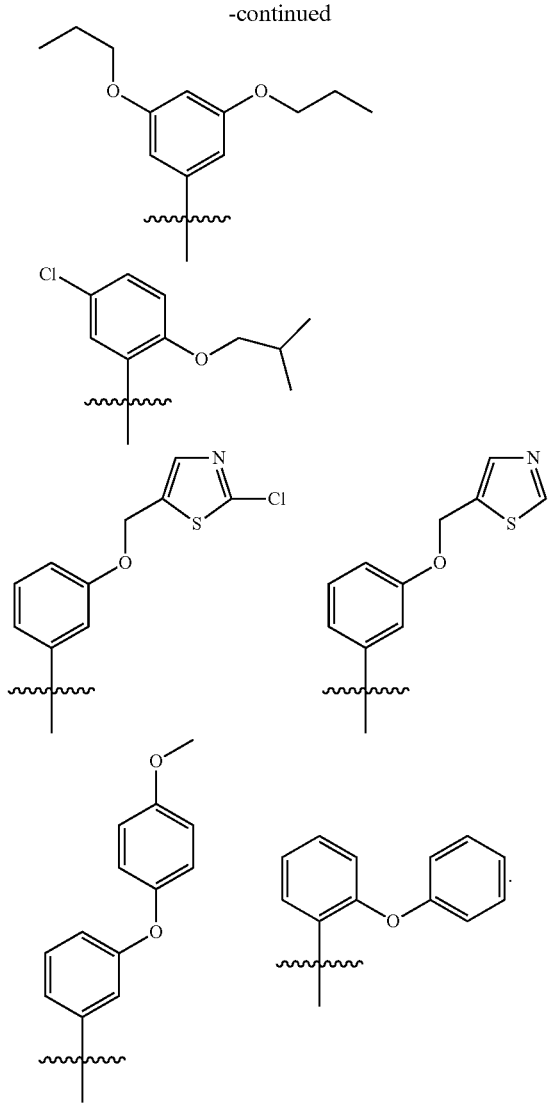

17. The compound, or pharmaceutically acceptable salt thereof, according to claim 1, which is selected from the group consisting of:
6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;
6-(Aminomethyl)-5-(3-hydroxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;
7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;
6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;
6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;
6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;
7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;
6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;
6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;
3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;
6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;
6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;
6-(Aminomethyl)-1,3-dimethyl-7-(naphthalen-2-ylmethylamino)-5-(2-phenoxyphenyl)pyrido[2,3-d]pyrimidine-2,4(1H,3H)-dione;
6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;
6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;
6-(Aminomethyl)-5-(3-fluorophenyl)-1,3-dimethyl-7-(naphthalen-2-ylmethylamino)pyrido[2,3-d]pyrimidine-2,4(1H,3H)-dione;
6-(Aminomethyl)-5-(2-isobutoxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(3-phenylpropylamino)pyrido[2,3-d]pyrimidine-2,4(1H,3H)-dione;
6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione;
6-(Aminomethyl)-5-(2-bromo-5-fluorophenyl)-7-(1,2-diphenylethylamino)-1,3-dimethylpyrido[2,3-d]pyrimidine-2,4(1H,3H)-dione;
6-(Aminomethyl)-5-(5-fluoro-2-methoxyphenyl)-7-(3-methoxybenzylamino)-1,3-dimethylpyrido[2,3-d]pyrimidine-2,4(1H,3H)-dione;
6-(Aminomethyl)-5-(5-fluoro-2-methoxyphenyl)-7-(3-isobutoxybenzylamino)-1,3-dimethylpyrido[2,3-d]pyrimidine-2,4(1H,3H)-dione;
5-(3,5-Dimethoxyphenyl)-6-((methylamino)methyl)-1,3-dimethyl-7-(naphthalen-2-ylmethylamino)pyrido[2,3-d]pyrimidine-2,4(1H,3H)-dione;
6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione;
6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione;
6-(Aminomethyl)-5-(5-fluoro-2-methoxyphenyl)-1,3-dimethyl-7-(phenethylamino)pyrido[2,3-d]pyrimidine-2,4(1H,3H)-dione;
6-(Aminomethyl)-5-(2-bromo-5-fluorophenyl)-7-(4-(ethylamino)phenylthio)-1,3-dimethylpyrido[2,3-d]pyrimidine-2,4(1H,3H)-dione;
N-(4-(6-(Aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide;

6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione;

5-(3,5-Dimethoxyphenyl)-6-((ethylamino)methyl)-1,3-dimethyl-7-(naphthalen-2-ylmethylamino)pyrido[2,3-d]pyrimidine-2,4(1H,3H)-dione;

6-(aminomethyl)-5-(2,4-dichlorophenyl)-7-(2,5-dipropoxybenzylamino)-1,3-dimethylpyrido[2,3-d]pyrimidine-2,4(1H,3H)-dione;

6-(Aminomethyl)-5-(benzo[d]thiazol-2-yl)-1,3-dimethyl-7-(naphthalen-2-ylmethylamino)pyrido[2,3-d]pyrimidine-2,4(1H,3H)-dione;

6-(aminomethyl)-7-(1,2-diphenylethylamino)-5-(5-fluoro-2-methoxyphenyl)-1,3-dimethylpyrido[2,3-d]pyrimidine-2,4(1H,3H)-dione;

6-(aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(aminomethyl)-7-(bis(naphthalen-2-ylmethyl)amino)-5-(3-hydroxyphenyl)-1,3-dimethylpyrido[2,3-d]pyrimidine-2,4(1H,3H)-dione; and pharmaceutically acceptable salts of the aforementioned compounds.

18. A pharmaceutical composition comprising, as an active ingredient, a compound, or a pharmaceutically acceptable salt thereof, as defined in claim 1.

19. A method of treating cardiovascular disease in a patient in need of treatment, comprising:

administering to a patient a therapeutically effective amount of a compound having the formula

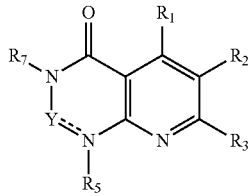

or a pharmaceutically acceptable salt thereof, wherein:

Y is selected from the group consisting of —C(O)—, —C(S)—, —S(O)—, —S(O)$_2$—, —C(R$_6$)(R$_{6'}$)—, and —C(NR$_6$R$_{6'}$)—;

R$_1$ is selected from the group consisting of (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;

R$_2$ is selected from the group consisting of amino(C$_{1-6}$)alkyl, (C$_{3-12}$)heterocycloalkyl, (C$_{4-12}$)heterobicycloaryl, heteroaryl, and cyano, each substituted or unsubstituted;

R$_3$ is selected from the group consisting of hydrogen, hydroxyl, halo, (C$_{1-10}$)perhaloalkyl, amino, nitro, cyano, thio, oxy, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, imino(C$_{1-3}$)alkyl, (C$_{1-10}$)alkylamino, amino(C$_{1-10}$)alkyl, aryl, heteroaryl, hydroxy, alkoxy, aryloxy, heteroaryloxy, carbonyl group, imino group, sulfonyl group and sulfinyl group, each substituted or unsubstituted; or R$_2$ and R$_3$ are taken together to form a ring;

R$_5$ and R$_7$ are each independently selected from the group consisting of hydrogen, (C$_{1-10}$)haloalkyl, amino, nitro, thio, sulfonamido, (C$_{1-10}$)alkyl, (C$_{3-12}$)cycloalkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, (C$_{3-12}$)cycloalkyl(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, carbonyl group, imino group, sulfonyl group and sulfinyl group, each substituted or unsubstituted, or R$_5$ is absent when the nitrogen atom on which R$_5$ is drawn forms part of a double bond; and R$_6$ and R$_{6'}$ are each independently selected from the group consisting of hydrogen, nitro, sulfonamido, (C$_{1-10}$)alkyl, (C$_{1-10}$)azaalkyl, (C$_{1-10}$)oxaalkyl, (C$_{1-10}$)oxoalkyl, hydroxy(C$_{1-10}$alkyl, (C$_{3-12}$)cycloalkyl, (C$_{1-12}$)heterocycloalkyl, aryl(C$_{1-10}$)alkyl, (C$_{1-5}$)heteroarylalkyl, (C$_{9-12}$)bicycloaryl, (C$_{4-12}$)heterobicycloaryl, (C$_{3-12}$)cycloalkyl(C$_{1-10}$)alkyl, (C$_{3-12}$)heterocycloalkyl(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, oxy group, carbonyl group, amino group, imino group, thio group, sulfonyl group and sulfinyl group, each substituted or unsubstituted, or R$_5$ and R$_6$ are taken together to form a ring, or R$_{6'}$ is absent when the carbon or nitrogen atom on which R$_{6'}$ is drawn forms part of a double bond, or when Y is CR$_6$R$_{6'}$, R$_6$ and R$_{6'}$ is taken together to form an oxo or a thioxo group;

wherein the cardiovascular disease is selected from hypertension, congestive heart failure, and myocardial infarction.

20. The method according to claim 19, wherein the compound has the formula

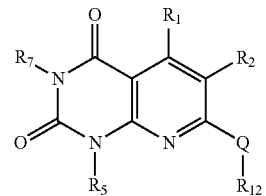

or is a pharmaceutically acceptable salt thereof, and

R$_1$, R$_2$, R$_5$, and R$_7$ are as defined in claim 19;

Q is selected from the group consisting of —O—, —S—, and —NR$_{13}$—;

R$_{12}$ is selected from the group consisting of (C$_{3-10}$)alkyl, phenyl, phenylalkyl, naphthylalkyl, each substituted or unsubstituted; and R$_{13}$ is selected from the group consisting of hydrogen, (C$_{1-10}$)haloalkyl, amino, thio, (C$_{1-10}$)alkyl, (C$_{3-12}$)heterocycloalkyl, aryl(C$_{1-10}$)alkyl, heteroaryl(C$_{1-5}$)alkyl, (C$_{9-12}$)bicycloaryl, (C$_{4-12}$)heterobicycloaryl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, hydroxy, alkoxy, aryloxy, heteroaryloxy, and imino group, each substituted or unsubstituted.

21. The method according to claim 19, wherein the compound, or pharmaceutically acceptable salt thereof, is selected from the group consisting of:

7-Amino-6-aminomethyl-5-(2,4-dichloro-phenyl)-1,3-dimethyl-1H-pyrido[2,3-d]pyrimidine-2,4-dione;
7-Amino-6-aminomethyl-5-(2-bromo-4-fluoro-phenyl)-1,3-dimethyl-1H-pyrido[2,3-d]pyrimidine-2,4-dione;
7-Amino-6-aminomethyl-5-(2-bromo-phenyl)-1,3-dimethyl-1H-pyrido[2,3-d]pyrimidine-2,4-dione;
6-Aminomethyl-5-(2,4-dichloro-phenyl)-7-ethylamino-1,3-dimethyl-1H-pyrido[2,3-d]pyrimidine-2,4-dione;
6-Aminomethyl-5-(2,4-dichloro-phenyl)-1,3-dimethyl-7-methylamino-1H-pyrido[2,3-d]pyrimidine-2,4-dione;
6-Aminomethyl-5-(2,4-dichloro-phenyl)-7-dimethylamino-1,3-dimethyl-1H-pyrido[2,3-d]pyrimidine-2,4-dione;
7-Hydroxy-5-(2-bromo-5-fluoro-phenyl)-1,3-dimethyl-2,4-dioxo-1,2,3,4-tetrahydropyrido[2,3-d]pyrimidine-6-carbonitrile;
6-Aminomethyl-5-(2-bromo-5-fluoro-phenyl)-7-hydroxy-1,3-dimethyl-1H-pyrido[2,3-d]pyrimidine-2,4-dione;
7-Amino-5-(2,5-dichloro-phenyl)-1,3-dimethyl-2,4-dioxo-1,2,3,4-tetrahydropyrido[2,3-d]pyrimidine-6-carbonitrile;
7-Amino-6-aminomethyl-5-(2,5-dichloro-phenyl)-1,3-dimethyl-1H-pyrido[2,3-d]pyrimidine-2,4-dione;
7-Amino-6-aminomethyl-5-(2-bromo-5-fluoro-phenyl)-1,3-dimethyl-1H-pyrido[2,3-d]pyrimidine-2,4-dione;
7-Amino-6-aminomethyl-1,3-dimethyl-5-(3-methyl-thiophen-2-yl)-1H-pyrido[2,3-d]pyrimidine-2,4-dione;
7-Amino-6-aminomethyl-5-(2-chloro-phenyl)-1,3-dimethyl-1H-pyrido[2,3-d]pyrimidine-2,4-dione;
7-Amino-6-aminomethyl-5-(4-fluoro-phenyl)-1,3-dimethyl-1H-pyrido[2,3-d]pyrimidine-2,4-dione;
7-Amino-6-aminomethyl-5-(5-chloro-thiophen-2-yl)-1,3-dimethyl-1H-pyrido[2,3-d]pyrimidine-2,4-dione;
7-Amino-6-aminomethyl-5-(4-bromo-phenyl)-1,3-dimethyl-1H-pyrido[2,3-d]pyrimidine-2,4-dione;
7-Amino-6-aminomethyl-5-(2,3-dichloro-phenyl)-1,3-dimethyl-1H-pyrido[2,3-d]pyrimidine-2,4-dione;
7-Amino-6-aminomethyl-5-(2-chloro-6-fluoro-phenyl)-1,3-dimethyl-1H-pyrido[2,3-d]pyrimidine-2,4-dione;
7-Amino-6-aminomethyl-5-(3-methoxy-phenyl)-1,3-dimethyl-1H-pyrido[2,3-d]pyrimidine-2,4-dione;
7-Amino-6-aminomethyl-5-(2-methoxy-phenyl)-1,3-dimethyl-1H-pyrido[2,3-d]pyrimidine-2,4-dione;
7-Amino-6-aminomethyl-5-(2-chloro-3,6-difluoro-phenyl)-1,3-dimethyl-1H-pyrido[2,3-d]pyrimidine-2,4-dione;
7-Amino-6-aminomethyl-5-phenyl-1,3-dimethyl-1H-pyrido[2,3-d]pyrimidine-2,4-dione;
7-Amino-6-aminomethyl-5-(3-bromo-thiophen-2-yl)-1,3-dimethyl-1H-pyrido[2,3-d]pyrimidine-2,4-dione;
7-Amino-6-aminomethyl-5-(2-chloro-5-fluoro-phenyl)-1,3-dimethyl-1H-pyrido[2,3-d]pyrimidine-2,4-dione;
7-Amino-6-aminomethyl-5-(2-bromo-5-fluoro-phenyl)-1,3-dimethyl-1H-pyrido[2,3-d]pyrimidine-2,4-dione;
7-Amino-6-aminomethyl-5-(2-chloro-4-fluoro-phenyl)-1,3-dimethyl-1H-pyrido[2,3-d]pyrimidine-2,4-dione;
7-Amino-6-aminomethyl-5-cyclopentyl-1,3-dimethyl-1H-pyrido[2,3-d]pyrimidine-2,4-dione;
7-Amino-6-aminomethyl-1,3-dimethyl-5-pyridin-3-yl-1H-pyrido[2,3-d]pyrimidine-2,4-dione;
7-Amino-6-aminomethyl-5-(4,5-dimethyl-thiophen-2-yl)-1,3-dimethyl-1H-pyrido[2,3-d]pyrimidine-2,4-dione;
7-Amino-6-aminomethyl-5-(5-fluoro-2-nitro-phenyl)-1,3-dimethyl-1H-pyrido[2,3-d]pyrimidine-2,4-dione;
7-Amino-6-aminomethyl-1,3-dimethyl-5-(3-methyl-3H-imidazol-4-yl)-1H-pyrido[2,3-d]pyrimidine-2,4-dione;
7-Amino-6-aminomethyl-5-benzo[b]thiophen-2-yl-1,3-dimethyl-1H-pyrido[2,3-d]pyrimidine-2,4-dione;
7-Amino-6-aminomethyl-1,3-dimethyl-5-(3-methyl-benzo[b]thiophen-2-yl)-1H-pyrido[2,3-d]pyrimidine-2,4-dione;
6-(Aminomethyl)-5-(2,4-dichlorophenyl)-7-hydroxy-1,3-dimethylpyrido[2,3-d]pyrimidine-2,4(1H,3H)-dione;
6-(Aminomethyl)-7-chloro-5-(2,4-dichlorophenyl)-1,3-dimethylpyrido[2,3-d]pyrimidine-2,4(1H,3H)-dione;
7-Amino-6-(aminomethyl)-5-(2-chloro-5-fluorophenyl)-3-methylpyrido[2,3-d]pyrimidine-2,4(1H,3H)-dione;
7-Amino-6-(aminomethyl)-5-(2-(aminomethyl)phenyl)-1,3-dimethylpyrido[2,3-d]pyrimidine-2,4(1H,3H)-dione;
2-(7-Amino-6-(aminomethyl)-1,3-dimethyl-2,4-dioxo-1,2,3,4-tetrahydropyrido[2,3-d]pyrimidin-5-yl)benzonitrile;
7-Amino-5-(2-(aminomethyl)phenyl)-1,3-dimethyl-2,4-dioxo-1,2,3,4-tetrahydropyrido[2,3-d]pyrimidine-6-carbonitrile;
6-(Aminomethyl)-7-(cyclopropylmethylamino)-5-(2,4-dichlorophenyl)-1,3-dimethylpyrido[2,3-d]pyrimidine-2,4(1H,3H)-dione;
2-(7-Amino-6-(aminomethyl)-1-isobutyl-3-methyl-2,4-dioxo-1,2,3,4-tetrahydropyrido[2,3-d]pyrimidin-5-yl)benzonitrile;
6-(Aminomethyl)-5-(2,4-dichlorophenyl)-1,3-dimethylpyrido[2,3-d]pyrimidine-2,4(1H,3H)-dione;
7-Amino-6-(aminomethyl)-5-(2-chloro-5-(trifluoromethyl)phenyl)-1,3-dimethylpyrido[2,3-d]pyrimidine-2,4(1H,3H)-dione;
7-Amino-6-(aminomethyl)-5-(2-chloro-5-fluorophenyl)-1-methylpyrido[2,3-d]pyrimidine-2,4(1H,3H)-dione;
7-Amino-6-(aminomethyl)-5-(2-bromo-5-fluorophenyl)-1-methylpyrido[2,3-d]pyrimidine-2,4(1H,3H)-dione;
2-(7-Amino-6-(aminomethyl)-1,3-dimethyl-2,4-dioxo-1,2,3,4-tetrahydropyrido[2,3-d]pyrimidin-5-yl)-4-fluorobenzonitrile;
2-(6-(Aminomethyl)-7-chloro-1,3-dimethyl-2,4-dioxo-1,2,3,4-tetrahydropyrido[2,3-d]pyrimidin-5-yl)-4-fluorobenzonitrile;
2-(6-(Aminomethyl)-1,3,7-trimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7-(trifluoromethyl)-1,2,3,4-tetrahydropyrido[2,3-d]pyrimidin-5-yl)-4-fluorobenzonitrile;
2-(6-(Aminomethyl)-1,3-dimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7-(2,2,2-trifluoroethylamino)-1,2,3,4-tetrahydropyrido[2,3-d]pyrimidin-5-yl)-4-fluorobenzonitrile;
2-(6-(Aminomethyl)-1,3-dimethyl-7-(methyl(2,2,2-trifluoroethyl)amino)-2,4-dioxo-1,2,3,4-tetrahydropyrido[2,3-d]pyrimidin-5-yl)-4-fluorobenzonitrile; 2-(6-(Aminomethyl)-7-(bis(trifluoromethyl)amino)-1,3-dimethyl-2,4-dioxo-1,2,3,4-tetrahydropyrido[2,3-d]pyrimidin-5-yl)-4-fluorobenzonitrile;
2-(6-(Aminomethyl)-1,3-dimethyl-2,4-dioxo-7,8-imidazo-[1,2-a]-1,2,3,4,7,8-hexahydropyrido[2,3-d]pyrimidin-5-yl)-5-chlorobenzonitrile;
2-(6-(Aminomethyl)-3-(cyclopropylmethyl)-1,7-dimethyl-2,4-dioxo-1,2,3,4-tetrahydropyrido[2,3-d]pyrimidin-5-yl)-5-chlorobenzonitrile;

6-(Aminomethyl)-5-(4-chloro-2-methoxyphenyl)-1,3,7-trimethylpyrido[2,3-d]pyrimidine-2,4(1H,3H)-dione;

2-(6-(Aminomethyl)-7-methoxy-1,3-dimethyl-2,4-dioxo-1,2,3,4-tetrahydropyrido[2,3-d]pyrimidin-5-yl)-5-chlorobenzonitrile;

2-(6-(Aminomethyl)-1,3-dimethyl-2,4-dioxo-7-(pyrrolidin-1-yl)-1,2,3,4-tetrahydropyrido[2,3-d]pyrimidin-5-yl)-5-chlorobenzonitrile;

6-(Aminomethyl)-5-(5-fluoro-2-methoxyphenyl)-1,3-dimethyl-7-morpholinopyrido[2,3-d]pyrimidine-2,4(1H,3H)-dione;

N-(6-(Aminomethyl)-5-(4-chloro-2-methoxyphenyl)-1,3-dimethyl-2,4-dioxo-1,2,3,4-tetrahydropyrido[2,3-d]pyrimidin-7-yl)methanesulfonamido;

2-(6-(Aminomethyl)-3-benzyl-7-methoxy-1-methyl-2,4-dioxo-1,2,3,4-tetrahydropyrido[2,3-d]pyrimidin-5-yl)-5-chlorobenzonitrile;

6-(Aminomethyl)-3-benzyl-5-(4-chloro-2-methoxyphenyl)-1-methyl-7-(trifluoromethyl)pyrido[2,3-d]pyrimidine-2,4(1H,3H)-dione;

6-(Aminomethyl)-5-(3,5-difluoro-2-methoxyphenyl)-1,3-dimethyl-7-(trifluoromethyl)pyrido[2,3-d]pyrimidine-2,4(1H,3H)-dione;

6-(Aminomethyl)-3-benzyl-5-(2-chloro-3,5-difluorophenyl)-1-methyl-7-(trifluoromethyl)pyrido[2,3-d]pyrimidine-2,4(1H,3H)-dione;

6-(Aminomethyl)-5-(2-bromo-3,5-difluorophenyl)-1,3-dimethyl-7-(trifluoromethyl)pyrido[2,3-d]pyrimidine-2,4(1H,3H)-dione;

6-(Aminomethyl)-5-(3,5-difluoro-2-methoxyphenyl)-1,2-imidazo-[1,2-a]-3-methyl-7-(trifluoromethyl)-2,3-dihydropyrido[2,3-d]pyrimidin-4(1H)-one;

6-(Aminomethyl)-5-(3,5-difluoro-2-methoxyphenyl)-3-methyl-2-(methylamino)-7-(trifluoromethyl)pyrido[2,3-d]pyrimidin-4(3H)-one;

2-Amino-6-(aminomethyl)-5-(2-chloro-3,5-difluorophenyl)-3-methyl-7-(trifluoromethyl)pyrido[2,3-d]pyrimidin-4(3H)-one;

2,7-Diamino-6-(1-aminoethyl)-5-(2-chloro-5-fluorophenyl)-3-methylpyrido[2,3-d]pyrimidin-4(3H)-one;

2-(6-(Aminomethyl)-7-ethoxy-1,3-dimethyl-2,4-dioxo-1,2,3,4-tetrahydropyrido[2,3-d]pyrimidin-5-yl)-5-chlorobenzonitrile;

6-(Aminomethyl)-5-(3,5-difluoro-2-methoxyphenyl)-2-(dimethylamino)-3-methyl-7-(trifluoromethyl)pyrido[2,3-d]pyrimidin-4(3H)-one;

6-(Aminomethyl)-7-(bis(2,2-difluoroethyl)amino)-5-(2-bromo-5-fluorophenyl)-1,3-dimethylpyrido[2,3-d]pyrimidine-2,4(1H,3H)-dione;

6-(Aminomethyl)-5-(2-bromo-5-fluorophenyl)-7-(2,2-difluoroethylamino)-1,3-dimethylpyrido[2,3-d]pyrimidine-2,4(1H,3H)-dione;

5-(2-Bromo-5-fluorophenyl)-7-chloro-1,3-dimethyl-2,4-dioxo-1,2,3,4-tetrahydropyrido[2,3-d]pyrimidine-6-carbonitrile;

5-(2-Bromo-5-fluoro-phenyl)-1,3-dimethyl-7-morpholin-4-yl-2,4-dioxo-1,2,3,4-tetrahydro-pyrido[2,3-d]pyrimidine-6-carbonitrile;

6-(Aminomethyl)-5-(2-bromo-5-fluorophenyl)-1,3-dimethyl-7-morpholinopyrido[2,3-d]pyrimidine-2,4(1H,3H)-dione;

6-(Aminomethyl)-5-(2-bromo-5-fluorophenyl)-1,3-dimethyl-7-(4-methylpiperazin-1-yl)pyrido[2,3-d]pyrimidine-2,4(1H,3H)-dione;

6-(Aminomethyl)-5-(2-bromo-5-fluorophenyl)-1,3-dimethyl-7-(pyridine-4-ylmethylamino)pyrido[2,3-d]pyrimidine-2,4(1H,3H)-dione;

6-(Aminomethyl)-5-(2-bromo-5-fluorophenyl)-1,3-dimethyl-7-(cyclopropylamino)-1,3-dimethylpyrido[2,3-d]pyrimidine-2,4(1H,3H)-dione;

6-(Aminomethyl)-5-(2,5-dichloro)-1,3-dimethyl-7-morpholinopyrido[2,3-d]pyrimidine-2,4(1H,3H)-dione;

7-Amino-6-(aminomethyl)-5-(2,4-dichlorophenyl)-1-methylpyrido[2,3-d]pyrimidine-2,4(1H,3H)-dione;

6-(Aminomethyl)-5-(2-bromo-5-fluorophenyl)-7-(diethylamino)-1,3-dimethylpyrido[2,3-d]pyrimidine-2,4(1H,3H)-dione;

6-(Aminomethyl)-5-(2-bromo-5-fluorophenyl)-7-(ethylamino)-1,3-dimethylpyrido[2,3-d]pyrimidine-2,4(1H,3H)-dione;

6-(Aminomethyl)-5-(2-bromo-5-fluorophenyl)-1,3-dimethyl-7-(methylamino)pyrido[2,3-d]pyrimidine-2,4(1H,3H)-dione;

6-(Aminomethyl)-5-(3,5-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(3-hydroxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(naphthalen-2-ylmethylamino)pyrido[2,3-d]pyrimidine-2,4(1H,3H)-dione;

7-(3-(1H-Pyrrol-1-yl)benzylamino)-6-(aminomethyl)-5-(3,5-dimethoxyphenyl)-1,3-dimethylpyrido[2,3-d]pyrimidine-2,4(1H,3H)-dione;

6-(Aminomethyl)-5-(3-(4-methoxyphenoxy)phenyl)-1,3-dimethyl-7-(naphthalen-2-ylmethylamino)pyrido[2,3-d]pyrimidine-2,4(1H,3H)-dione;

6-(Aminomethyl)-5-(2,5-diethoxyphenyl)-1,3-dimethyl-7-(naphthalen-2-ylmethylamino)pyrido[2,3-d]pyrimidine-2,4(1H,3H)-dione;

6-(Aminomethyl)-1,3-dimethyl-7-(naphthalen-2-ylmethylamino)-5-(3-(thiazol-5-ylmethoxy)phenyl)pyrido[2,3-d]pyrimidine-2,4(1H,3H)-dione;

7-(4-(1H-Pyrazol-1-yl)benzylamino)-6-(aminomethyl)-5-(5-fluoro-2-methoxyphenyl)-1,3-dimethylpyrido[2,3-d]pyrimidine-2,4(1H,3H)-dione;

6-(Aminomethyl)-5-(2,2-dimethyl-2,3-dihydrobenzofuran-7-yl)-1,3-dimethyl-7-(naphthalen-2-ylmethylamino)pyrido[2,3-d]pyrimidine-2,4(1H,3H)-dione;

6-(Aminomethyl)-7-(3-(benzyloxy)benzylamino)-5-(5-fluoro-2-methoxyphenyl)-1,3-dimethylpyrido[2,3-d]pyrimidine-2,4(1H,3H)-dione;

3-(6-(Aminomethyl)-1,3-dimethyl-7-(naphthalen-2-ylmethylamino)-2,4-dioxo-1,2,3,4-tetrahydropyrido[2,3-d]pyrimidin-5-yl)-N,N-dimethylbenzamide;

6-(Aminomethyl)-5-(5-fluoro-2-methoxyphenyl)-1,3-dimethyl-7-(pentan-3-ylamino)pyrido[2,3-d]pyrimidine-2,4(1H,3H)-dione;

6-(Aminomethyl)-5-(5-fluoro-2-methoxyphenyl)-1,3-dimethyl-7-(2-(trifluoromethyl)benzylamino)pyrido[2,3-d]pyrimidine-2,4(1H,3H)-dione;

6-(Aminomethyl)-1,3-dimethyl-7-(naphthalen-2-ylmethylamino)-5-(2-phenoxyphenyl)pyrido[2,3-d]pyrimidine-2,4(1H,3H)-dione;

6-(Aminomethyl)-5-(5-chloro-2-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(3-((2-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(Aminomethyl)-5-(3-fluorophenyl)-1,3-dimethyl-7-(naphthalen-2-ylmethylamino)pyrido[2,3-d]pyrimidine-2,4(1H,3H)-dione;

6-(Aminomethyl)-5-(2-isobutoxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(3-phenylpropylamino)pyrido[2,3-d]pyrimidine-2,4(1H,3H)-dione;

6-(Aminomethyl)-5-(3,4-dimethoxyphenyl)-1,3-dimethyl-7-(naphthalen-2-ylmethylamino)pyrido[2,3-d]pyrimidine-2,4(1H,3H)-dione;

6-(Aminomethyl)-5-(2-bromo-5-fluorophenyl)-7-(1,2-diphenylethylamino)-1,3-dimethylpyrido[2,3-d]pyrimidine-2,4(1H,3H)-dione;

6-(Aminomethyl)-5-(5-fluoro-2-methoxyphenyl)-7-(3-methoxybenzylamino)-1,3-dimethylpyrido[2,3-d]pyrimidine-2,4(1H,3H)-dione;

6-(Aminomethyl)-5-(5-fluoro-2-methoxyphenyl)-7-(3-isobutoxybenzylamino)-1,3-dimethylpyrido[2,3-d]pyrimidine-2,4(1H,3H)-dione;

5-(3,5-Dimethoxyphenyl)-6-((methylamino)methyl)-1,3-dimethyl-7-(naphthalen-2-ylmethylamino)pyrido[2,3-d]pyrimidine-2,4(1H,3H)-dione;

6-(Aminomethyl)-5-(2,5-dipropoxyphenyl)-1,3-dimethyl-7-(naphthalen-2-ylmethylamino)pyrido[2,3-d]pyrimidine-2,4(1H,3H)-dione;

6-(Aminomethyl)-5-(3,5-diethoxyphenyl)-1,3-dimethyl-7-(naphthalen-2-ylmethylamino)pyrido[2,3-d]pyrimidine-2,4(1H,3H)-dione;

6-(Aminomethyl)-5-(5-fluoro-2-methoxyphenyl)-1,3-dimethyl-7-(phenethylamino)pyrido[2,3-d]pyrimidine-2,4(1H,3H)-dione;

6-(Aminomethyl)-5-(2-bromo-5-fluorophenyl)-7-(4-(ethylamino)phenylthio)-1,3-dimethylpyrido[2,3-d]pyrimidine-2,4(1H,3H)-dione;

N-(4-(6-(Aminomethyl)-5-(2-bromo-5-fluorophenyl)-1,3-dimethyl-2,4-dioxo-1,2,3,4-tetrahydropyrido[2,3-d]pyrimidin-7-ylthio)phenyl)acetamide;

6-(Aminomethyl)-5-(3,5-dipropoxyphenyl)-1,3-dimethyl-7-(naphthalen-2-ylmethylamino)pyrido[2,3-d]pyrimidine-2,4(1H,3H)-dione;

5-(3,5-Dimethoxyphenyl)-6-((ethylamino)methyl)-1,3-dimethyl-7-(naphthalen-2-ylmethylamino)pyrido[2,3-d]pyrimidine-2,4(1H,3H)-dione;

6-(Aminomethyl)-5-(2,4-dichlorophenyl)-7-(2,5-dipropoxybenzylamino)-1-methylpyrido[2,3-d]pyrimidine-2,4(1H,3H)-dione;

7-Amino-6-(aminomethyl)-5-(3-isobutoxyphenyl)-1,3-dimethylpyrido[2,3-d]pyrimidine-2,4(1H,3H)-dione;

7-Amino-6-(aminomethyl)-1,3-dimethylpyrido[2,3-d]pyrimidine-2,4(1H,3H)-dione;

7-Amino-6-(Aminomethyl)-5-(4-(aminomethyl)phenyl)-1,3-dimethylpyrido[2,3-d]pyrimidine-2,4(1H,3H)-dione;

6-(Aminomethyl)-5-(benzo[d]thiazol-2-yl)-1,3-dimethyl-7-(naphthalen-2-ylmethylamino)pyrido[2,3-d]pyrimidine-2,4(1H,3H)-dione;

6-(aminomethyl)-7-(1,2-diphenylethylamino)-5-(5-fluoro-2-methoxyphenyl)-1,3-dimethylpyrido[2,3-d]pyrimidine-2,4(1H,3H)-dione;

6-(aminomethyl)-5-(3-((4-chlorothiazol-5-yl)methoxy)phenyl)-1,3-dimethyl-7-(naphthalen-2-ylmethylamino)pyrido[2,3-d]pyrimidine-2,4(1H,3H)-dione;

6-(aminomethyl)-7-(bis(naphthalen-2-ylmethyl)amino)-5-(3-hydroxyphenyl)-1,3-dimethylpyrido[2,3-d]pyrimidine-2,4(1H,3H)-dione; and pharmaceutically acceptable salts of the aforementioned compounds.

\* \* \* \* \*